US012780915B2

(12) United States Patent
Liu et al.

(10) Patent No.: US 12,780,915 B2
(45) Date of Patent: Nov. 3, 2026

(54) ANTI-CD47 ANTIBODY AND USE THEREOF

(71) Applicant: Bio-Thera Solutions, Ltd., Guangzhou (CN)

(72) Inventors: Xianqin Liu, Guangzhou (CN); Jingyi Shen, Guangzhou (CN); Weijia Tang, Guangzhou (CN); Jin-Chen Yu, Guangzhou (CN); Shengfeng Li, Guangzhou (CN)

(73) Assignee: BIO-THERA SOLUTIONS, LTD., Guangzhou (CN)

( * ) Notice: Subject to any disclaimer, the term of this patent is extended or adjusted under 35 U.S.C. 154(b) by 826 days.

(21) Appl. No.: 18/018,804

(22) PCT Filed: Jul. 30, 2021

(86) PCT No.: PCT/CN2021/109446

§ 371 (c)(1),
(2) Date: Jan. 30, 2023

(87) PCT Pub. No.: WO2022/022662

PCT Pub. Date: Feb. 3, 2022

(65) Prior Publication Data

US 2023/0303711 A1 Sep. 28, 2023

(30) Foreign Application Priority Data

Jul. 31, 2020 (CN) ......................... 202010761404.8

(51) Int. Cl.
*C07K 16/28* (2006.01)
*A61P 35/00* (2006.01)
*C12N 15/63* (2006.01)

(52) U.S. Cl.
CPC .......... *C07K 16/2803* (2013.01); *A61P 35/00* (2018.01); *C07K 16/2896* (2013.01); *C12N 15/63* (2013.01); *C07K 2317/52* (2013.01); *C07K 2317/56* (2013.01); *C07K 2317/565* (2013.01); *C07K 2317/622* (2013.01)

(58) Field of Classification Search
CPC ............ C07K 16/2803; C07K 16/2896; C07K 2317/56; C07K 2317/565; C07K 2317/33; C07K 2317/52; C07K 2317/73; C07K 2317/76; C07K 2317/92; C07K 2317/622; A61P 35/00; A61P 31/00; C12N 15/63; A61K 2039/505
See application file for complete search history.

(56) References Cited

U.S. PATENT DOCUMENTS

| | | | |
|---|---|---|---|
| 7,973,140 B2 | 7/2011 | Green et al. | |
| 2006/0246071 A1 | 11/2006 | Green et al. | |
| 2016/0257751 A1 | 9/2016 | Swanson et al. | |
| 2018/0250395 A1 | 9/2018 | Pietsch et al. | |
| 2019/0292258 A1* | 9/2019 | Lippincott | C07K 16/2803 |
| 2024/0067728 A1 | 2/2024 | Chen et al. | |

FOREIGN PATENT DOCUMENTS

| | | | | |
|---|---|---|---|---|
| AU | 2015374301 A1 | 7/2017 | | |
| AU | 2016324316 A1 | 4/2018 | | |
| CA | 3089512 A1 | 8/2019 | | |
| CN | 104271757 A | 1/2015 | | |
| CN | 105101997 A | 11/2015 | | |
| JP | 2018510147 A | 4/2018 | | |
| WO | WO-2015063339 A1 * | 5/2015 | | C07K 16/2887 |
| WO | 2019042285 A1 | 3/2019 | | |
| WO | 2019108733 A2 | 6/2019 | | |
| WO | WO-2021032174 A1 * | 2/2021 | | C07K 16/28 |
| WO | 2022095970 A1 | 5/2022 | | |

OTHER PUBLICATIONS

Gershoni (Biodrugs (2007) 21(3): 145-156) (Year: 2007).*
Sela-Culang (Frontiers in Immunology (2013) 4: 302) (Year: 2013).*
Almagro (Frontiers in Immunology (2018) 8: 1751) (Year: 2018).*
U.S. Appl. No. 18/035,591. Bispecific Antibody and Use Thereof, filed 2023. Published 2023 in U.S. Appl. No. 18/035,591 A1. (Year: 2023).*
U.S. Appl. No. 18/681,485. Use of ANTI-PD-L1/CD47 Bispecific Antibody in Treatment of Diseases, filed 2024. Published 2025 in U.S. Appl. No. 18/681,485 A1. (Year: 2024).*
Ni (The Protein Journal (2024) 43: 683-696) (Year: 2024).*
Extended European Search Report issued on Jan. 10, 2025, in EP Application No. 21850447.0.
Chothia et al., Canonical Structures for the Hypervariable Regions of Immunoglobulins, J. Mol. Biol. 196:901-17 (1987).
Chothia et al., Conformations of immunoglobulin hypervariable regions, Nature 342:877-883 (Dec. 21/28, 1989).
Cote et al., Generation of human monoclonal antibodies reactive with cellular antigens, Proc. Natl. Acad. Sci. 80:2026-2030 (Apr. 1983).
Davies et al., Antibody-Antigen Complexes, Annu. Rev. Biochem 59:439-73 (1990).
Gorman et al., The Rous sarcoma virus long terminal repeat is a strong promoter when introduced into a variety of eukaryotic cells by DNA-mediated transfection, Proc. Natl. Acad. Sci. 79:6777-6781 (Nov. 1982).
Grosschedl et al., Cell-Type Specificity of Immunoglobulin Gene Expression is Regulated by at Least Three DNA Sequence Elements, Cell, 41:885-892 (Jul. 1985).
Hacker et al., Recombinant DNA Technology for Production of Protein Therapeutics in Cultured Mammalian Cells, Reference Module in Life Sciences (Jan. 2017).
Johansen et al., Dual Regulation of SIRPa Phosphorylation by Integrins and CD47, J. Biol. Chem. 282(33):24219-24230 (Aug. 17, 2007).

(Continued)

*Primary Examiner* — Julie Wu
*Assistant Examiner* — Elizabeth A Shupe
(74) *Attorney, Agent, or Firm* — Panitch Schwarze Belisario & Nadel LLP

(57) ABSTRACT

CD47 antibodies and use thereof are disclosed, particularly to monoclonal antibodies that recognize CD47, and more particularly to CD47 antibodies that do not cause significant levels of hemagglutination, red blood cell reduction and platelet reduction, and to a method for preparing these antibodies and use of these monoclonal antibodies in the manufacture of medicaments for treating cancer or infection.

13 Claims, 11 Drawing Sheets

Specification includes a Sequence Listing.

(56) References Cited

OTHER PUBLICATIONS

Kozbor et al., The production of monoclonal antibodies from human lymphocytes, Immunology Today 4(3):72-80 (1983).
Köhler et al., Continuous cultures of fused cells secreting antibody of predefined specificity, Nature 256:495-497 (Aug. 7, 1975).
Liu et al., Chimeric mouse-human IgGi antibody that can mediate lysis of cancer cells, Proc. Natl. Acad. Sci. 84:3439-3443 (May 1987).
Liu et al., Production of a Mouse-Human Chimeric Monoclonal Antibody to CD20 with Potent Fc-Dependent Biologic Activity, The Journal of Immunology 139(10):3521-3526 (Nov. 15, 1987).
Malmqvist, Biospecific interaction analysis using biosensor technology, Nature 361:186-187 (Jan. 14, 1993).
Matozaki et al., Functions and molecular mechanisms of the CD47-SIRPa signalling pathway, Trends in Cell Biology 19(2) 72-80 (Jan. 12, 2009).
Morrison et al., Success in specification, Nature 368:812-813 (Apr. 28, 1994).
Okayama et al., A cDNA cloning vector that permits expression of cDNA inserts in mammalian cells, Mol. Cell. Biol. 3(2):280-289 (1983).
Thornton et al., Prediction of progress at last, Nature 354:105-106 (Nov. 14, 1991).
Willingham et al., Reply to Soto-Pantoja et al. and Zhao et al.: Targeting CD47 on human solid tumors, PNAS 109(42) 1-2 (Aug. 24, 2012).
Winter et al., Humanized antibodies, Immunology Today 14(6): 243-246 (1993).
International Search Report issued Sep. 29, 21 in PCT/CN2021/109446.
Ohshima, N. et al., "GenBank Database" GenBank Accession No. BAU69745.1, Apr. 1, 2016 Features, Origin in part.
Lantto, J., et al. "GenBank Database" GenBank Accession No. ADU57829.1, Jul. 25, 2016, Features, Origin in part.
Notice of Reasons for Refusal issued in counterpart Japanese Patent Application 2023-506542 issued on Jul. 14, 2025.
Partial Supplementary European Search Report issued on Oct. 18, 2024, in EP Application No. 21850447.0.

* cited by examiner

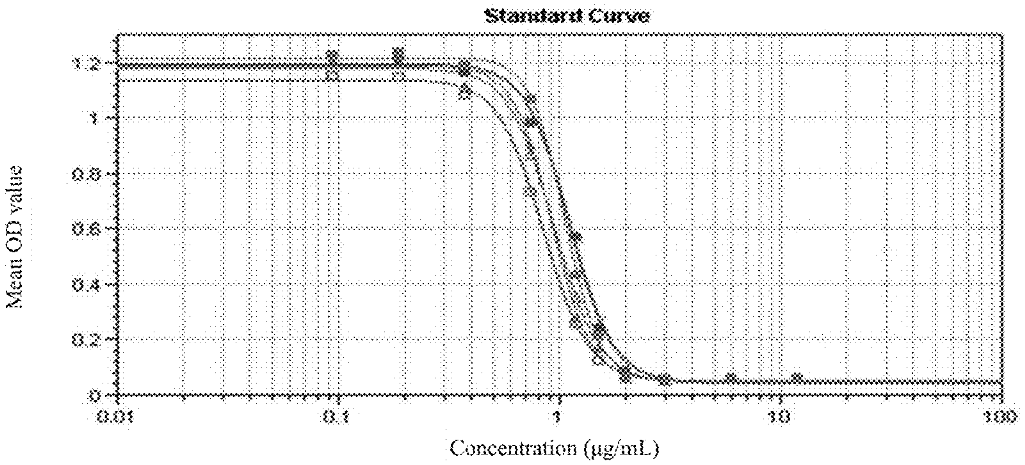

| y = ( (A - D)/(1 + (x/C)^B ) ) + D: | A | B | C | D | R^2 |
|---|---|---|---|---|---|
| Plot#1 (3: Concentration vs Values) | 1.14 | 4.223 | 0.844 | 0.047 | 0.999 |
| Plot#2 (3-3: Concentration vs Values) | 1.18 | 4.249 | 0.939 | 0.046 | 0.998 |
| Plot#3 (3-6: Concentration vs Values) | 1.165 | 4.415 | 1.122 | 0.046 | 0.999 |
| Plot#4 (6: Concentration vs Values) | 1.197 | 4.391 | 1.102 | 0.042 | 0.996 |
| Plot#5 (10: Concentration vs Values) | 1.219 | 5.498 | 1.056 | 0.05 | 0.999 |
| Plot#6 (11: Concentration vs Values) | 1.19 | 4.971 | 0.921 | 0.053 | 0.998 |

FIG. 3B

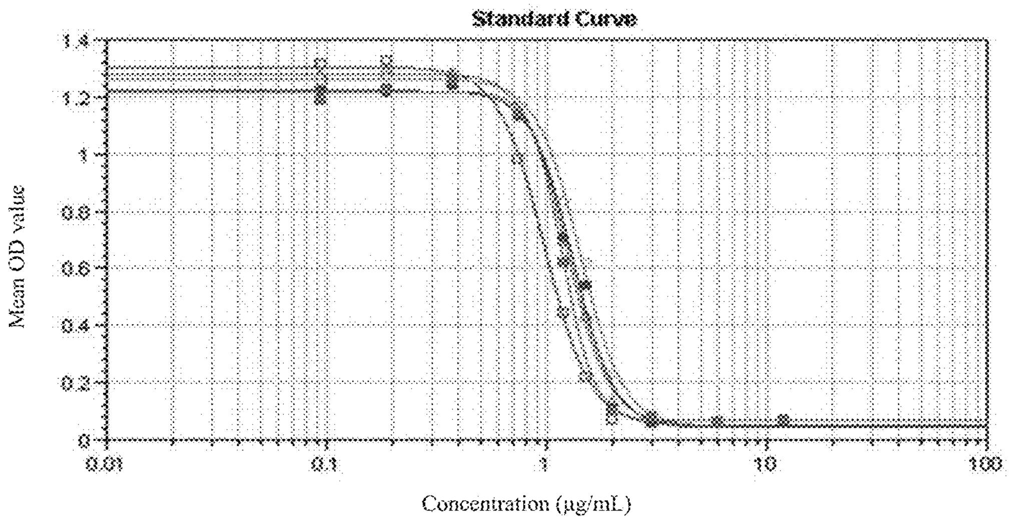

| y = ( (A - D)/(1 + (x/C)^B ) ) + D: | A | B | C | D | R^2 |
|---|---|---|---|---|---|
| Plot#1 (16: Concentration vs Values) | 1.305 | 4.159 | 0.975 | 0.048 | 0.999 |
| Plot#2 (18: Concentration vs Values) | 1.284 | 4.51 | 1.232 | 0.05 | 0.999 |
| Plot#3 (24: Concentration vs Values) | 1.263 | 4.376 | 1.412 | 0.046 | 0.998 |
| Plot#4 (25: Concentration vs Values) | 1.222 | 4.576 | 1.31 | 0.041 | 0.993 |
| Plot#5 (L12: Concentration vs Values) | 1.222 | 6.014 | 1.182 | 0.064 | 0.999 |

FIG. 3C

| y = ( (A - D)/(1 + (x/C)^B ) ) + D: | A | B | C | D | R^2 |
|---|---|---|---|---|---|
| □ Plot#1 (L1: Concentration vs Values) | 1.261 | 4.189 | 0.967 | 0.046 | 0.993 |
| △ Plot#2 (L5: Concentration vs Values) | 1.264 | 3.7 | 1.021 | 0.036 | 0.982 |
| ◇ Plot#3 (L24: Concentration vs Values) | 1.273 | 4.656 | 1.088 | 0.049 | 0.996 |
| ● Plot#4 (L26: Concentration vs Values) | 1.339 | 4.593 | 1.016 | 0.063 | 0.995 |
| ▩ Plot#5 (17: Concentration vs Values) | 1.27 | 2.572 | 0.795 | 0.129 | 0.997 |
| ▲ Plot#6 (IgG: Concentration vs Values) | 1.343 | 0.558 | 13389.93 | 8.036 | 0.903 |

| y = ( (A - D)/(1 + (x/C)^B ) ) + D: | A | B | C | D | R^2 |
|---|---|---|---|---|---|
| ○ Plot#1 (6Y-G1: Concentration vs MeanValue) | 1.261 | 3.998 | 0.913 | 0.057 | 0.998 |
| △ Plot#3 (IgG: Concentration vs MeanValue) | 1.192 | 1.144 | 5.757 | 1.394 | 0.967 |
| □ Plot#2 (6Y-G4: Concentration vs MeanValue) | 1.263 | 3.651 | 0.763 | 0.054 | 0.996 |

ANTI-CD47 ANTIBODY AND USE THEREOF

CROSS-REFERENCE TO RELATED APPLICATIONS

This application is a Section 371 of International Application No. PCT/CN2021/109446, filed Jul. 30, 2021, which was published in the Chinese language on Feb. 3, 2022 under International Publication No. WO 2022/022662 A1, which claims priority under 35 U.S.C. § 119 (b) to Chinese Application No. 202010761404.8, filed Jul. 31, 2020, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "689755_8US_Sequence_Listing", creation date of Jan. 30, 2023, and having a size of 63,819 bytes. The sequence listing submitted via EFS-Web is part of the specification and is herein incorporated by reference in its entirety.

TECHNICAL FIELD

The present invention relates to the technical field of bio-immunology, particularly to a fully human anti-CD47 IgG antibody, and more particularly to CD47 antibodies that do not cause significant hemagglutination of human red blood cells, hemoglobin reduction, anemia and/or platelet reduction, methods for preparing these antibodies and use of these monoclonal antibodies in the manufacture of medicaments.

BACKGROUND

CD47, also known as integrin-associated protein (IAP), is a transmembrane glycoprotein that is extensively expressed on the cell surface and belongs to the immunoglobulin superfamily (Johansen and Brown, *J. Biol. Chem.* 2007). CD47 binds to its ligand signal regulatory protein α (SIRPα), thereby inhibiting macrophages' phagocytosis (Matozaki T, et al., *Trends Cell Biol.* 2009). Studies have confirmed that CD47 is overexpressed in many malignancies, such as acute myeloid leukemia (AML), B-cell and T-cell acute leukemia and non-Hodgkin lymphoma, and evades immune surveillance by sending "don't eat me" signals to macrophages, and high expression of CD47 is associated with poor clinical prognosis (Willingham et al. *Proc Natl Acad Sci USA.* 2012).

U.S. patent application 2009/0191202 discloses that professor Weissman's team from Stanford University conducted an experiment with a xenograft animal model of orthotopic immunodeficient mice and found that the administration of anti-CD47 monoclonal antibodies could inhibit the growth and metastasis of large tumors and cure small tumors. U.S. patent application 2016/0251435 discloses the use of anti-CD47 monoclonal antibodies in the treatment of tumors. The patent application WO2013056352 describes the use of humanized anti-human SIRPα full-length monoclonal antibodies and antibody fragments derived therefrom in the treatment of hematological tumors, particularly leukemia. Blocking the CD47-SIRPα signaling pathway can promote the phagocytosis of tumor cells by macrophages, providing a new means for tumor immunotherapy.

SUMMARY

The present invention provides antibodies that recognize and bind to CD47. In some embodiments, the antibodies disclosed herein are capable of recognizing and binding to human CD47. The antibodies disclosed herein can prevent CD47 from interacting with SIRPα without causing significant hemagglutination of red blood cells. The antibodies provided herein are collectively referred to as "CD47 antibodies".

In some embodiments, the CD47 antibodies disclosed herein exhibit a variety of desirable properties, such as, according to non-limiting embodiments, specifically recognizing human or macaque CD47, effectively blocking the interaction between CD47 and its ligand SIRPα without causing significant hemagglutination of red blood cells, and having effective antitumor activity.

In some embodiments, the present invention provides an antibody or an antigen-binding fragment that specifically binds to human integrin-associated protein (CD47) and that comprises 1, 2, 3, 4, 5 or 6 of the below described VH CDR1, VH CDR2, VH CDR3, VL CDR1, VL CDR2 and VL CDR3, wherein:

(a) VH CDR1 comprising an amino acid sequence set forth in SEQ ID NO: 14, or a variant of SEQ ID NO: 14 having 1-3 amino acid substitutions shown in Table 1 in the sequence SEQ ID NO: 14;
(b) VH CDR2 comprising an amino acid sequence set forth in SEQ ID NO: 17, or a variant of SEQ ID NO: 17 having 1-3 amino acid substitutions shown in Table 1 in the sequence SEQ ID NO: 17;
(c) VH CDR3 comprising an amino acid sequence set forth in SEQ ID NO: 23, or a variant of SEQ ID NO: 23 having 1-3 amino acid substitutions shown in Table 1 in the sequence SEQ ID NO: 23;
(d) VL CDR1 comprising any one of amino acid sequences set forth in SEQ ID NOs: 30-31;
(e) VL CDR2 comprising any one of amino acid sequences set forth in SEQ ID NOs: 32-33; and
(f) VL CDR3 comprising any one of amino acid sequences set forth in SEQ ID NOs: 34-35.

In some embodiments, the present invention provides an antibody or an antigen-binding fragment that specifically binds to human integrin-associated protein (CD47) and that comprises 1, 2, 3, 4, 5 or 6 of the below described VH CDR1, VH CDR2, VH CDR3, VL CDR1, VL CDR2 and VL CDR3, wherein:

(a) VH CDR1 comprising any one of amino acid sequences set forth in SEQ ID NOs: 14-16;
(b) VH CDR2 comprising any one of amino acid sequences set forth in SEQ ID NOs: 17-22;
(c) VH CDR3 comprising any one of amino acid sequences set forth in SEQ ID NOs: 23-29;
(d) VL CDR1 comprising any one of amino acid sequences set forth in SEQ ID NOs: 30-31;
(e) VL CDR2 comprising any one of amino acid sequences set forth in SEQ ID NOs: 32-33; and
(f) VL CDR3 comprising any one of amino acid sequences set forth in SEQ ID NOs: 34-35.

In some embodiments, the present invention provides an antibody or an antigen-binding fragment that specifically binds to human integrin-associated protein (CD47) and that comprises 1, 2, 3, 4, 5 or 6 of the following sequences:

(a) VH CDR1 set forth in SEQ ID NO: 14, or a variant of SEQ ID NO: 14 having 1-3 amino acid substitutions shown in Table 1 in the sequence SEQ ID NO: 14;

(b) VH CDR2 set forth in SEQ ID NO: 17, or a variant of SEQ ID NO: 17 having 1-3 amino acid substitutions shown in Table 1 in the sequence SEQ ID NO: 17;

(c) VH CDR3 set forth in SEQ ID NO: 23, or a variant of SEQ ID NO: 23 having 1-3 amino acid substitutions shown in Table 1 in the sequence SEQ ID NO: 23;

(d) any one of VL CDR1s set forth in SEQ ID NOs: 30-31;

(e) any one of VL CDR2s set forth in SEQ ID NOs: 32-33; and (f) any one of VL CDR3s set forth in SEQ ID NOs: 34-35.

In some embodiments, the present invention provides an antibody or an antigen-binding fragment that specifically binds to human integrin-associated protein (CD47) and that comprises:

(a) any one of VH CDR1s set forth in SEQ ID NOs: 14-16;

(b) any one of VH CDR2s set forth in SEQ ID NOs: 17-22;

(c) any one of VH CDR3s set forth in SEQ ID NOs: 23-29;

(d) any one of VL CDR1s set forth in SEQ ID NOs: 30-31;

(e) any one of VL CDR2s set forth in SEQ ID NOs: 32-33; and (f) any one of VL CDR3s set forth in SEQ ID NOs: 34-35.

In some embodiments, the antibody or the antigen-binding fragment comprises a heavy chain variable region VH, which comprises an amino acid sequence selected from any one of SEQ ID NOs: 11, 36-44, 50 and 56, or an amino acid sequence having at least 90% sequence identity to an amino acid sequence of any one of SEQ ID NOs: 11, 36-44, 50 and 56.

In some embodiments, the antibody or the antigen-binding fragment comprises a light chain variable region VL, which comprises an amino acid sequence selected from any one of SEQ ID NOs: 12-13, 45-49, 51-55 and 65, or an amino acid sequence having at least 90% sequence identity to an amino acid sequence of any one of SEQ ID NOs: 12-13, 45-49, 51-55 and 65.

In some embodiments, the present invention provides an antibody or an antigen-binding fragment that specifically binds to human integrin-associated protein (CD47) and that comprises VH CDR1 set forth in SEQ ID NO: 14, VH CDR2 set forth in SEQ ID NO: 17, VH CDR3 set forth in SEQ ID NO: 23, VL CDR1 set forth in SEQ ID NO: 30, VL CDR2 set forth in SEQ ID NO: 32, and VL CDR3 set forth in SEQ ID NO: 34.

In some embodiments, the antibody or the antigen-binding fragment comprises a heavy chain variable region VH, which comprises one or more amino acid residue mutations according to Kabat numbering selected from the group consisting of:

(a) R81K, and (b) R82aS.

In some embodiments, the antibody or the antigen-binding fragment comprises a heavy chain variable region VH, which comprises an amino acid sequence selected from any one of SEQ ID NOs: 11 and 50, or an amino acid sequence having at least 90% sequence identity to an amino acid sequence of any one of SEQ ID NOs: 11 and 50.

In some embodiments, the antibody or the antigen-binding fragment comprises a light chain variable region VL, which comprises an amino acid sequence selected from any one of SEQ ID NOs: 13, 45-49, 51-55 and 65, or an amino acid sequence having at least 90% sequence identity to an amino acid sequence of any one of SEQ ID NOs: 13, 45-49, 51-55 and 65.

In some embodiments, the antibody or the antigen-binding fragment comprises a heavy chain variable region VH and a light chain variable region VL; the VH comprises an amino acid sequence selected from SEQ ID NOs: 11 and 50, and the VL comprises an amino acid sequence selected from SEQ ID NOs: 13 and 65.

In some embodiments, the CD47 antibody disclosed herein specifically recognizes and binds to human or macaque CD47; the antibody comprises a heavy chain variable region of an amino acid sequence selected from any one of SEQ ID NOs: 11, 36-44 and 50 and/or a light chain variable region of an amino acid sequence selected from any one of SEQ ID NOs: 12, 13, 45-49, 51-55 and 65.

In some embodiments, the antibody or the antigen-binding fragment comprises a heavy chain H and a light chain L; the heavy chain H comprises an amino acid sequence selected from any one of SEQ ID NOs: 60 and 62-63, and the light chain L comprises an amino acid sequence selected from any one of SEQ ID NOs: 61 and 64.

In some embodiments, the CD47 antibody disclosed herein block at least 40%, at least 45%, at least 50%, at least 55%, at least 60%, at least 65%, at least 70%, at least 75%, at least 80%, at least 85%, at least 95%, or at least 99% of the interaction between CD47 and SIRPα occurred in the absence of the CD47 antibody.

In some embodiments, the antibody comprises a heavy chain constant region and/or a light chain constant region; the heavy chain constant region comprises an amino acid sequence selected from SEQ ID NOs: 3 and 4, and the light chain constant region comprises an amino acid sequence selected from SEQ ID NO: 5.

```
IgG1 heavy chain constant region sequence (SEQ ID NO: 3):
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

IgG4 heavy chain constant region sequence (SEQ ID NO: 4):
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK
```

-continued

```
Light chain constant region sequence (SEQ ID NO:
5)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

In some embodiments, the CD47 antibodies disclosed herein do not cause significant cell agglutination; for example, the CD47 antibodies disclosed herein do not cause significant hemagglutination of red blood cells. In some embodiments, if the level of agglutination occurred in the presence of the CD47 antibodies disclosed herein decreases by at least 5%, at least 10%, at least 20%, at least 30%, at least 40%, at least 50%, at least 60%, at least 70%, at least 80%, at least 90% or at least 99% compared to the level of agglutination occurred in the presence of the existing CD47 antibody Hu5F9-G4, the CD47 antibodies disclosed herein are shown not to cause significant agglutination. In some embodiments, the CD47 antibodies disclosed herein do not cause significant cell agglutination when at an antibody concentration between 400 pM and 800 nM.

In some embodiments, the antibodies disclosed herein are also significantly effective in tumor models compared to known antibodies in the art. For example, the ability of macrophages to phagocytose tumor cells is increased by at least 5%, at least 10%, at least 20%, at least 30%, at least 40%, at least 50%, at least 60%, at least 70%, at least 80%, at least 90% or at least 99% in the presence of the CD47 antibodies disclosed herein.

In some embodiments, the antibody or the antigen-binding fragment is of an IgG isotype selected from the group consisting of IgG1 isotype, IgG2 isotype, IgG3 isotype and IgG4 isotype. In some embodiments, the antibody or the antigen-binding fragment is of an IgG isotype selected from IgG4P and IgG4PE. IgG4P refers to the mutation of the Ser228 site of the hinge region of IgG4 into Pro to prevent chain exchange. IgG4PE refers to the mutation of the Ser228 site of the hinge region of IgG4 into Pro to prevent chain exchange and the mutation of Leu235 of the constant region into Glu to alter the interaction with an Fc receptor.

In some embodiments, the antibody is chimeric, humanized or fully human. In some embodiments, the antibody binds to human CD47.

In some embodiments, the CD47 antibody or antigen-binding fragment is an isolated CD47 antibody or antigen-binding fragment.

In some embodiments, the CD47 antibody or antigen-binding fragment disclosed herein is a monoclonal antibody or fragment thereof.

In some embodiments, the CD47 antibodies or antigen-binding fragments disclosed herein can be used in the manufacture of medicaments for treating cancer or infection. In some embodiments, the CD47 antibodies or antigen-binding fragments disclosed herein can be used in the manufacture of medicaments for treating solid tumors or hematological tumors. In some embodiments, the CD47 antibodies or antigen-binding fragments disclosed herein can be used in the manufacture of medicaments for treating non-Hodgkin lymphoma (NHL), acute lymphocytic leukemia (ALL), acute myelogenous leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, breast cancer, ovarian cancer, lung cancer, prostate cancer, melanoma, colorectal cancer, head and neck cancer, bladder cancer, esophageal cancer, liver cancer and renal cancer. In some embodiments, the CD47 antibodies or antigen-binding fragments disclosed herein can be used in the manufacture of medicaments for treating diffuse large B-cell lymphoma or follicular lymphoma.

In some embodiments, the CD47 antibodies disclosed herein can be used to treat, delay the progression of, avoid relapses of, or alleviate the symptoms of cancer or other neoplastic conditions. For example, the CD47 antibodies disclosed herein can be used to treat hematological malignancies and/or tumors, e.g., hematological malignancies and/or tumors. For example, the CD47 antibodies disclosed herein can be used to treat $CD47^{+}$ tumors. By way of non-limiting example, the CD47 antibodies disclosed herein can be used to treat non-Hodgkin lymphoma (NHL), acute lymphocytic leukemia (ALL), acute myelogenous leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, etc. Solid tumors include, for example, breast cancer, ovarian cancer, lung cancer, prostate cancer, melanoma, colorectal cancer, head and neck cancer, bladder cancer, esophageal cancer, liver cancer and renal cancer. For example, the CD47 antibodies disclosed herein can be used to treat diffuse large B cell lymphoma or follicular lymphoma.

As used herein, "hematological cancer" includes leukemia, lymphoma, myeloma, etc. "Leukemia" refers to hematologic cancer that produces too many white blood cells that are not effective against infection, which crowd out other components that constitute the blood, such as platelets and red blood cells. Cases of leukemia can be acute or chronic. By ways of non-limiting example, leukemia can include acute lymphocytic leukemia (ALL), acute myelogenous leukemia (AML), chronic lymphocytic leukemia (CLL), chronic myelogenous leukemia (CML), myeloproliferative diseases/tumors (MPDs) and myelodysplastic syndrome. "Lymphoma" can include Hodgkin lymphoma, indolent and aggressive non-Hodgkin lymphoma, Burkitt lymphoma, follicular lymphoma (small cell and large cell), etc. Myeloma can include multiple myeloma (MM), giant cell myeloma, heavy chain myeloma and light chain or Bence-Jones myeloma.

Exemplary monoclonal antibodies of the present invention include, for example, the antibodies disclosed herein. Exemplary antibodies include ones having a heavy chain variable region of an amino acid sequence selected from any one of SEQ ID NOs: 11, 36-44, 50 and 56 and a light chain variable region of an amino acid sequence selected from any one of SEQ ID NOs: 12, 13, 45-49, 51-55 and 65. The antibodies also include ones having a heavy chain variable region having at least 90%, 91%, 92%, 93%, 94%, 95%, 96%, 97%, 98%, 99% or higher identity to at least one of the sequences SEQ ID NOs: 11, 36-44, 50 and 56 and a light chain variable region having at least 90%, 91%, 92%, 93%, 94%, 95%, 96%, 97%, 98%, 99% or higher identity to at least one of the sequences SEQ ID NOs: 12, 13, 45-49, 51-55 and 65. These antibodies exhibit specificity for human CD47 and can prevent CD47 from interacting with SIRPα without causing significant hemagglutination of red blood cells.

In some embodiments, the present invention also provides a biomaterial, which is (1) a polynucleotide encoding the antibody or the antigen-binding fragment disclosed herein; or (2) an expression vector comprising a polynucleotide encoding the antibody or the antigen-binding fragment disclosed herein; or (3) a cell comprising one or more polynucleotides encoding the antibody or the antigen-binding fragment disclosed herein.

The pharmaceutical compositions disclosed herein can comprise the antibodies disclosed herein and pharmaceutically acceptable carriers. These pharmaceutical compositions can be contained in a kit, such as a diagnostic kit.

The present invention also provides a method for alleviating the symptoms of cancer or other neoplastic conditions by administering to a subject in need one or more monoclonal antibodies that bind to CD47 or immunologically active fragments thereof; the antibodies will not cause significant hemagglutination of red blood cells after administration. The antibody should be administered at a dose sufficient to alleviate the symptoms of cancer or other neoplastic conditions in the subject. In some embodiments, the subject is a human. In some embodiments, the antibodies or the immunologically active fragments thereof prevent CD47 from interacting with SIRPα.

In some embodiments, the CD47 antibodies disclosed herein are used in combination with one or more other agents. Suitable other agents include existing drugs and/or surgical therapies for particular applications (such as cancer). For example, the CD47 antibodies used in combination with one or more other chemotherapeutic or antitumor agents. Alternatively, the other chemotherapeutic agent is radiotherapy. In some embodiments, the chemotherapeutic agent is an apoptosis inducer. In some embodiments, the chemotherapeutic agent induces an asymmetry loss of cross plasma membrane phospholipid, e.g., causing cell surface exposure of phosphatidylserine (PS). In some embodiments, the chemotherapeutic agent induces endoplasmic reticulum (ER) stress. In some embodiments, the chemotherapeutic agent is a proteasome inhibitor. In some embodiments, the chemotherapeutic agent induces the translocation of ER proteins to the cell surface. In some embodiments, the chemotherapeutic agent induces the translocation and cell surface exposure of calreticulin.

In some embodiments, the anti-CD47 antibody and the other agent are formulated into a single therapeutic composition, and the anti-CD47 antibody and the other agent are administered simultaneously. Alternatively, the anti-CD47 antibody and the other agent are separated from each other, for example, are each formulated into a separate therapeutic composition, and the anti-CD47 antibody and the other agent are administered simultaneously, or the anti-CD47 antibody and the other agent are administered at different times during a treatment regimen. For example, the CD47 antibody is administered prior to the administration of the other agent, the CD47 antibody is administered subsequent to the administration of the other agent, or the CD47 antibody and the other agent are administered in an alternating manner. In the present invention, the anti-CD47 antibody and the other agent are administered in single doses or in multiple doses.

In some embodiments, provided is the use of the antibody or the antigen-binding fragment, the composition and the biomaterial disclosed herein in the manufacture of medicaments for treating cancer or infection.

It will be understood by those skilled in the art that the antibodies disclosed herein can be widely used. For example, the antibodies disclosed herein can be used as therapeutic agents, reagents in diagnostic kits or diagnostic tools, or reagents in competitive experiments to produce therapeutic agents.

BRIEF DESCRIPTION OF THE DRAWINGS

FIG. 3 is a set of graphs, and FIGS. 3A-3E show the ability of CD47 antibodies to block the binding of SIRPα to CD47 antigen, as assessed by a competitive ELISA.

FIG. 4 is a set of graphs, FIG. 4A shows that Antibody 11 causes significant hemagglutination; FIG. 4B shows that Antibody L12 does not cause hemagglutination; FIG. 4C shows Antibody L12-6 does not cause hemagglutination; FIG. 4D shows that Antibody 17 and Hu5F9-G4 cause significant hemagglutination and that AB6.12-G1 and SIRPα do not cause hemagglutination; FIG. 4E shows that Antibody 6Y-G4 does not cause hemagglutination.

FIG. 5 is a set of graphs.

FIG. 6 is a set of graphs.

FIG. 7 is a set of graphs, FIGS. 7A-7B show that Antibody 6Y-G1 causes a reduction in the hemoglobin and red blood cell levels, which begin to gradually recover approximately 2 weeks later; the extent of reaction is similar to that caused by Antibody AB6.12-G1 or Hu5F9-G4. FIG. 7C shows that the number of platelets fluctuates every time Antibody 6Y-G1 is administered, and recovers after the administration ends; FIG. 7D shows that every time Antibody 6Y-G1 is administered, the reticulocytes count increases, and the increase was greater than those caused to the treatment groups of antibodies AB6.12-G1 and Hu5F9-G4.

DETAILED DESCRIPTION

The present invention provides antibodies that specifically bind to CD47. In some embodiments, the antibodies disclosed herein are capable of specifically binding to human CD47. These antibodies are collectively referred to herein as anti-CD47 antibodies. Unless otherwise stated herein, the amino acid residues in the variable regions and constant regions of antibodies are numbered according to the Kabat scheme (Kabat et al., 1991, EU indexes in Sequences of Proteins of Immunological Interest).

Some properties of the antibodies disclosed herein include: a) specifically binding to CD47 (e.g., human CD47 and macaque CD47); b) blocking the interaction between CD47 and SIRPα; c) not having significant hemagglutination activity; d) being capable of promoting the phagocytosis of tumor cells by macrophages; and/or e) showing effective antitumor activity in mouse models of human cancer.

Thus, the antibodies disclosed herein play an important role in the treatment of a variety of cancers.

Many existing CD47 antibodies block SIRPα; however, the existing antibodies that block SIRPα can cause an unwanted side effect—hemagglutination. Other existing antibodies (such as 2D3) do not cause hemagglutination; however, these antibodies do not block SIRPα either, rendering them ineffective in the promotion of phagocytosis. Therefore, cell agglutination is a major limitation on the uses of the existing full-length IgG antibodies to therapeutically target CD47. Therefore, there is an urgent need for CD47 antibodies that are capable of blocking SIRPα without causing cell aggregation.

The CD47 antibodies disclosed herein avoid unwanted hemagglutination, thereby increasing the effectiveness of therapeutic targeting CD47, and maintain the ability to block the interaction between CD47 and SIRPα, thereby promoting phagocytosis of CD47-expressing cells. In some embodiments, the CD47 antibodies disclosed herein (e.g., Antibody L12 and Antibody L12-6) do not agglutinate cells at significant levels. For example, the CD47 antibodies disclosed herein do not agglutinate RBCs at significant levels.

Figure 6A:
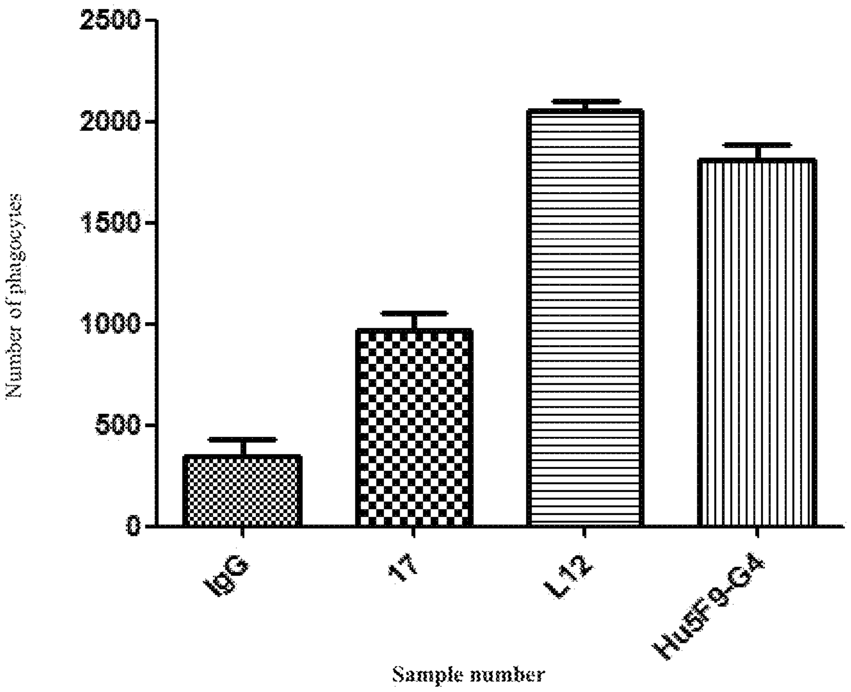
FIGS. 6A-6B show the ability of CD47 antibodies to promote phagocytosis of Raji by RAW264.7, as assessed by flow cytometry.
Figure 6B:
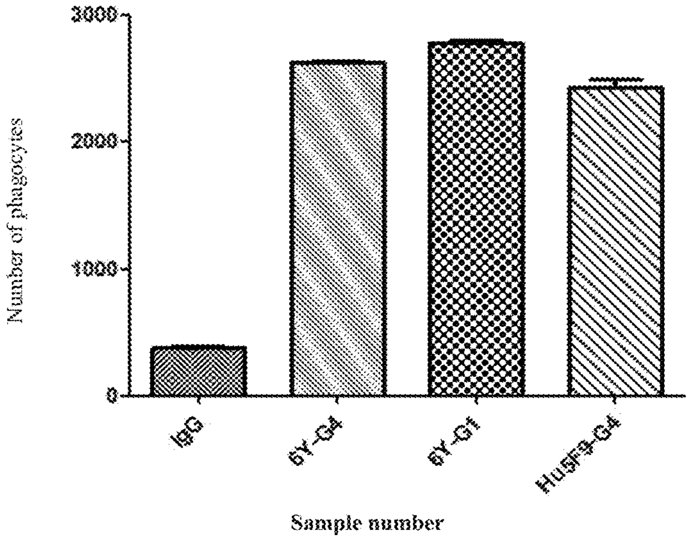
Figure 7A:
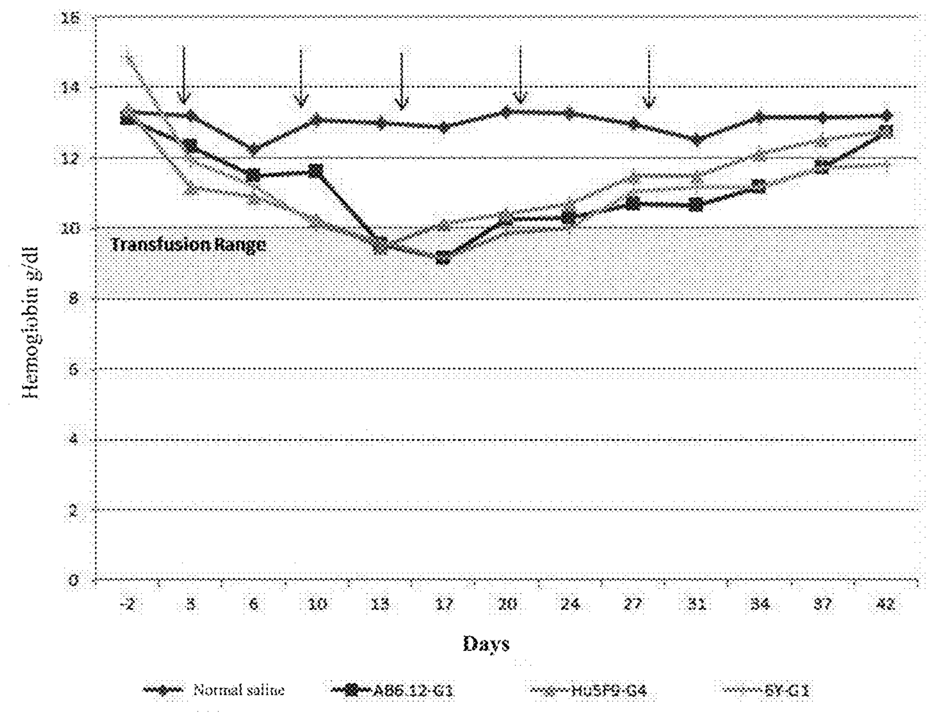
FIGS. 7A-7D show an analysis of the effects of Antibody 6Y-G1 on red blood cells and platelets in cynomolgus monkeys.
Figure 7B:
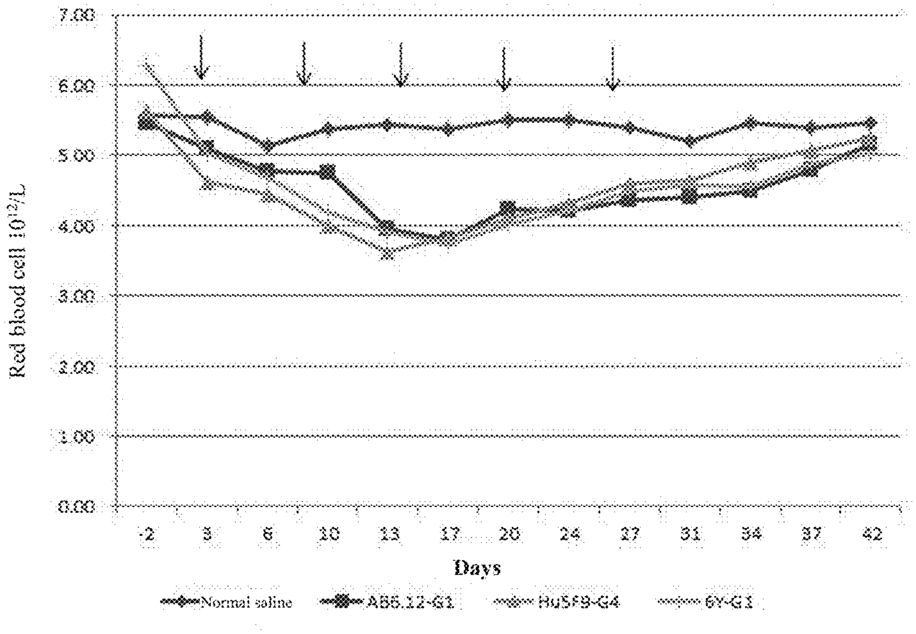
Figure 7C:
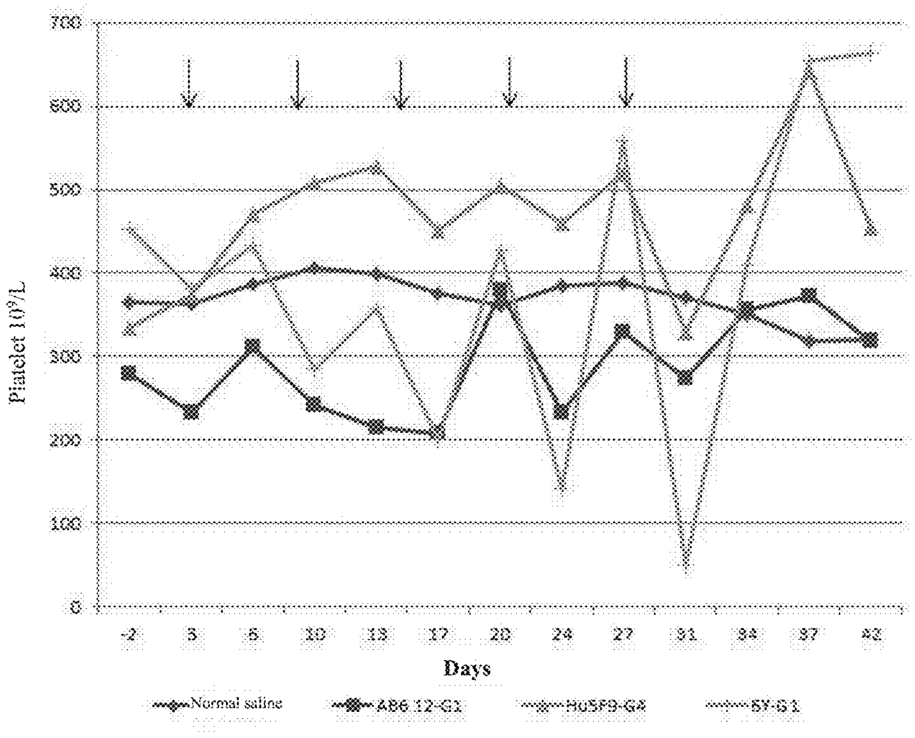
Figure 7D:
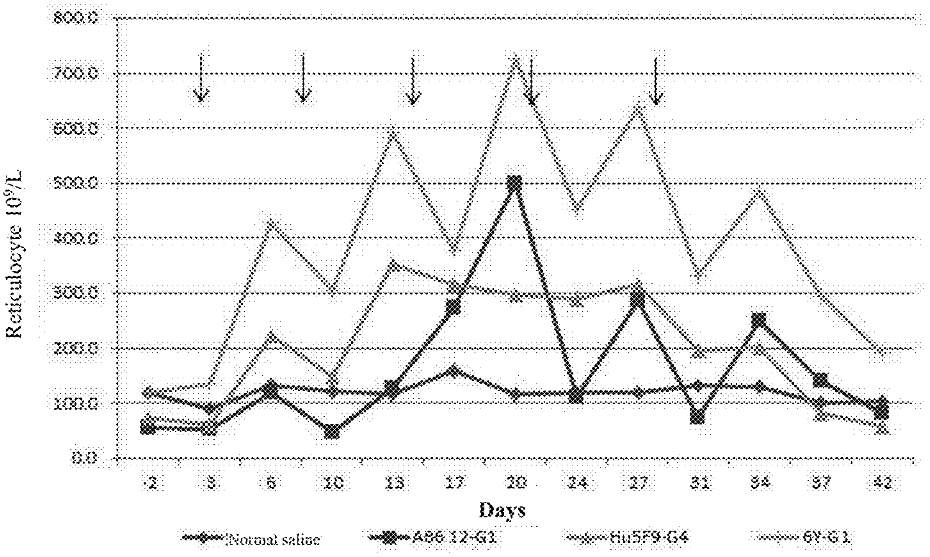
Figure 9:
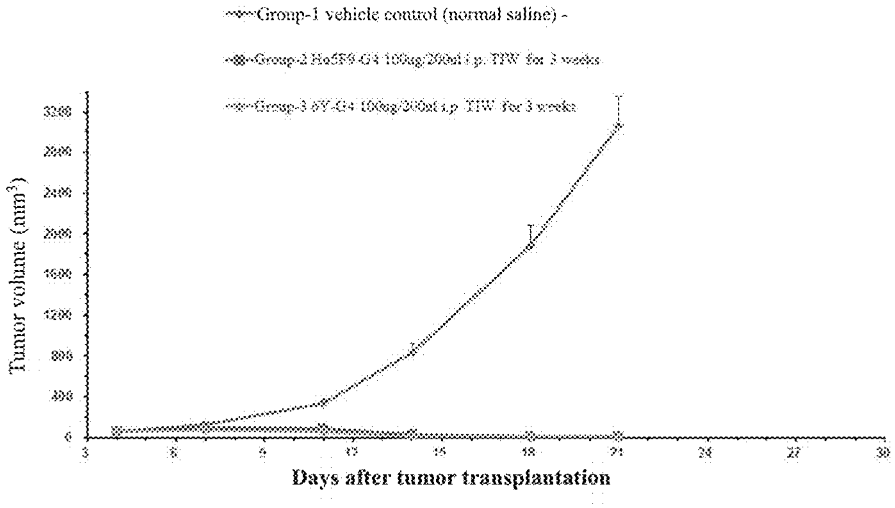
FIG. 9 shows an analysis of the antitumor effect of Antibody 6Y-G4 in the Raji tumor model; the mice were treated at an antibody dose of 100 μg, three times a week.

The CD47 antibodies disclosed herein bind to human CD47 and block its interaction with SIRPα (FIGS. 3A-3E). These antibodies do not cause significant hemagglutination of human red blood cells (FIGS. 4A-4E). These antibodies are capable of promoting the phagocytosis of tumor cells by macrophages (FIGS. 6A-6B). In addition, these CD47 antibodies exhibit effective antitumor activity in a mouse model of human Raji lymphoma (FIG. 9). Thus, the CD47 antibodies disclosed herein overcome one major limitation on therapeutic targeting of CD47. Thus, the CD47 antibodies disclosed herein are of great importance in the treatment of a number of cancers.

The antibody disclosed herein binds to the CD47 epitope with an equilibrium dissociation constant (KD) of less than or equal to 1 μM, e.g., less than or equal to 100 nM, such as less than or equal to 10 nM, or less than or equal to 1 nM. For example, the CD47 antibodies provided herein exhibit KD values of less than 1 nM.

The CD47 antibodies disclosed herein serve to modulate, block, inhibit, reduce, antagonize, neutralize or interfere with the functional activity of the widely distributed CD47. Functional activities of CD47 include, for example, signaling via the interaction with SIRPα, modulating (e.g., increasing) intracellular calcium ion concentration upon cell adhesion to the extracellular matrix, interacting with the C-terminal cell binding domain of thrombospondin, interacting with fibrinogen, and interacting with various integrins. For example, the CD47 antibodies completely or partially inhibit the functional activity of CD47 by partially or completely modulating, blocking, inhibiting, reducing, antagonizing, neutralizing or interfering with the binding of CD47 to SIRPα.

Definitions

Unless otherwise defined, scientific and technical terms used in the present invention have the meanings that are commonly understood by those skilled in the art. Generally, the nomenclature and techniques used in cell culture, molecular biology and protein purification described herein are well known and commonly used in the art. Standard techniques are used for recombinant DNA, oligonucleotide synthesis and cell culture and transformation (e.g., electroporation and lipofection). Enzymatic reactions and purification techniques are performed according to the manufacturer's instructions, or methods commonly used in the art or described herein. The aforementioned techniques and methods are generally used as described in various comprehensive and specific documents that are well known in the art and that are cited and discussed in this specification. See, e.g., Sambrook et al., Molecular Cloning: A Laboratory Manual (the $2^{nd}$ edition, Cold Spring Harbor Laboratory Press, Cold Spring Harbor, N.Y. (1989)).

As used in this disclosure, unless otherwise stated, the following terms shall be understood to have the following meanings: The terms "red blood cell" and "erythrocyte" are synonymous and are used interchangeably.

The term "agglutination" refers to clumping of cells, while the term "hemagglutination" refers to clumping of a particular type of cells (i.e., red blood cells). Therefore, hemagglutination is one type of agglutination. In the hemagglutination assay described herein, red blood cells form in a given well a form that can be a "button", a "halo" or an intermediate between the two. The term "in a line" means that masses of red blood cells flow in a line upon tilting the 96-well plate 45°. The term "significant hemagglutination activity" refers to the presence of any halo form in the well upon addition of the antibodies described herein.

The term "antibody" as used herein refers to immunoglobulin (Ig) molecules and immunologically active portions of immunoglobulin molecules, i.e., molecules that contain an antigen-binding site that specifically binds to (immunoreacts with) an antigen. By "specifically bind" or "immunoreact" or "directed against" is meant that the antibody reacts with one or more antigenic determinants of the target antigen and does not react with other polypeptides, or binds to other polypeptides with very low affinity ($KD>10^{-6}$ g/mL). Antibodies include, but are not limited to, monoclonal antibodies, chimeric antibodies, dAbs (domain antibodies), single-chain antibodies, Fab, Fab- and F(ab')2 fragments, Fv and Fab expression libraries.

The basic antibody structural unit is known to comprise a tetramer. Each tetramer (or "full-length antibody") is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from each other by the nature of the heavy chain present in the molecule. Certain classes also have subclasses, such as IgG1, IgG2, and others. Furthermore, in humans, the light chain may be a κ chain or a λ chain.

As used herein, the term "monoclonal antibody" (mAb) refers to a population of antibody molecules that contain only one molecular species of the antibody molecules consisting of a unique light chain gene product and a unique heavy chain gene product. In particular, the complementarity-determining regions (CDRs) of the monoclonal antibody are identical in all the molecules of the population. MAbs contain an antigen-binding site capable of immunoreacting with a particular epitope of an antigen.

The term "single-chain antibody" (scFv) refers to an antibody in which its heavy chain variable region (VH) and light chain variable region (VL) are linked by a linker of 15-20 amino acids.

The term "antigen-binding site" or "binding portion" refers to the portion of an immunoglobulin molecule that is involved in antigen binding. The antigen-binding site is formed from amino acid residues of the N-terminal variable ("V") region of the heavy ("H") chain and the light ("L") chain. Three highly differentiated branches (referred to as "hypervariable regions") in the heavy chain variable region (VH) and light chain variable region (VL) are located between more conserved branches (referred to as "framework regions" or "FRs"). Thus, the term "FR" refers to amino acid sequences that naturally occur between or adjacent to hypervariable regions in immunoglobulins. In an antibody molecule, the three hypervariable regions of a light chain and the three hypervariable regions of a heavy chain are arranged relative to each other in three-dimensional space to form an antigen-binding surface. The antigen-binding surface is complementary to the three-dimensional surface of the bound antigen, and the three hypervariable regions of each of the heavy chains and light chains are referred to as "complementarity-determining regions" or "CDRs". The alignment of amino acids to each domain can be in accordance with the definitions of Kabat Sequences of Proteins of Immunological Interest (National Institutes of Health (1987 and 1991)) or Chothia and Lesk's articles (J. Mol. Biol. 196:901-917 (1987); Chothia et al., Nature 342: 878-883 (1989)).

The term "epitope" as used herein includes any protein determining region that can specifically bind to an immunoglobulin or a fragment thereof or a T cell receptor. The epitope determinant generally consists of chemically active surface groups of molecules (such as amino acids or sugar side chains), and usually has specific three-dimensional structural properties and specific charge properties.

As used herein, the term "specific binding" refers to the type of non-covalent interactions that occur between an immunoglobulin molecule and an antigen for which the immunoglobulin is specific. The strength or affinity of an immunological binding interaction can be expressed in terms of the equilibrium dissociation constant (KD) of the interaction, where a smaller KD represents a greater affinity. The immunological binding properties of the selected polypeptides may be quantified using methods well known in the art. One such method requires the measurement of the rates of antigen-binding site/antigen complex formation and dissociation, where those rates depend on the concentration of the complex partners, the affinity of the interaction and geometric parameters that affect the rates equally in both directions. Thus, both "association rate constant" ($k_{on}$) and "dissociation rate constant" ($k_{off}$) can be determined by calculating the concentration and the actual association and dissociation rates. (see *Nature* 361:186-87 (1993)). The ratio $k_{off}/k_{on}$ can eliminate all the parameters that are independent of the affinity and is equal to the equilibrium dissociation constant KD. (generally see Davies et al. (1990) *Annual Rev Biochem* 59:439-473). Specific binding can be measured by radiolig and binding assays, surface plasmon resonance (SPR), flow cytometry binding assay, or similar assays known to those skilled in the art. When the equilibrium dissociation constant (KD)≤1 μM (e.g., less than or equal to 100 nM, less than or equal to 10 nM, or less than or equal to 1 nM), the antibodies disclosed herein specifically bind to CD47.

An "isolated" antibody is one that is isolated and/or recovered from a component of its natural environment. Contaminant components of its natural environment are substances that would interfere with diagnostic or therapeutic uses of the antibody, and can include enzymes, hormones, and other proteinaceous or non-proteinaceous solutes. In some embodiments, the antibody is purified to the following extent: (1) the percentage, by weight, of the antibody is greater than 95%, e.g., greater than 99%, as measured by the Lowry method; (2) at least 15 residues of the N-terminal or internal amino acid sequence can be obtained by using a spinning cup sequenator; or (3) the antibody is homogeneous, as determined by reducing or non-reducing SDS-PAGE with Coomassie blue or silver staining. Isolated antibodies include antibodies in situ within recombinant cells. Typically, an isolated antibody will be prepared through at least one or more purification steps. In some embodiments, the purity of the isolated antibody is at least about 50%, about 60%, about 70%, about 80%, about 90%, about 95%, about 99%, or within the range between any two of these values (inclusive), or any values therein.

The term "polypeptide" is used herein as a generic term to refer to native proteins, fragments or analogs of a polypeptide sequence. Thus, native protein fragments and analogs are members of the polypeptide genus.

The term "sequence identity" or "sequence homology" means that two polynucleotides or amino acid sequences are identical (i.e., are identical on a nucleotide-by-nucleotide or residue-by-residue basis) over the comparison window. The term "percentage of sequence identity" is calculated by comparing two optimally aligned sequences over the comparison window, determining the number of positions at which the identical nucleic acid base (e.g., A, T, C, G, U or I) or amino acid residue occurs in both sequences to yield the number of matched positions, dividing the number of matched positions by the total number of positions in the comparison window (i.e., the window size), and then multiplying the result by 100 to yield the percentage of sequence identity.

As used herein, the twenty conventional amino acids and their abbreviations follow conventional usage. See Immunology-A Synthesis (the 2nd edition, Eds. E. S. Golub and D. R. Gren, Sinauer Associates, Sunderland 7 Mass. (1991)). Stereoisomers (e.g., D-amino acids) of the twenty conventional amino acids, unnatural amino acids (such as α- or α-disubstituted amino acids), N-alkyl amino acids, lactic acid, and other unconventional amino acids can also be suitable components for the polypeptides of the present disclosure. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine and other similar amino acids and imino acids (e.g., 4-hydroxyproline). In the polypeptide notation used herein, the left-hand direction is the amino-terminal direction and the right-hand direction is the carboxy-terminal direction, in accordance with standard usage and convention. The conventional (natural) amino acids include alanine (three-letter symbol: Ala, one-letter symbol: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Similarly, unless otherwise stated, the left-hand end of a single-stranded polynucleotide sequence is the 5' end, and the left-hand direction of a double-stranded polynucleotide sequence is referred to as the 5' direction. The direction of 5' to 3' addition of nascent RNA transcripts is referred to as the transcription direction; sequence regions on the DNA strand which have the same sequence as the RNA and are 5' to the 5' end of the RNA transcript are referred to as "upstream sequences"; sequence regions on the DNA strand which have the same sequence as the RNA and are 3' to the 3' end of the RNA transcript are referred to as "downstream sequences". The term "substantially identical" when applied to polypeptides means that two peptide sequences, when optimally aligned, such as by the program GAP or BESTFIT using default gap weights, share at least 80% sequence identity, preferably at least 90% sequence identity, more preferably at least 95% sequence identity, and most preferably at least 99% sequence identity.

In some embodiments, residue positions that are not identical differ by conservative amino acid substitutions.

Minor variations in the amino acid sequences of antibodies or immunoglobulin molecules are contemplated by the present disclosure, provided that the identity of the amino acid sequences retains at least 75%, such as at least 80%, 90%, 95%, and as another example 99%. In some embodiments, the variations are conservative amino acid substitutions. Conservative amino acid substitutions are ones that occur within a family of amino acids that are related in their side chains. Genetically encoded amino acids are generally classified into the following categories: (1) acidic amino acids are aspartate and glutamate; (2) basic amino acids are lysine, arginine and histidine; (3) non-polar amino acids are alanine, valine, leucine, isoleucine, proline, phenylalanine, methionine, tryptophan; and (4) uncharged polar amino acids are glycine, asparagine, glutamine, cysteine, serine, threonine and tyrosine. Amino acids of the other families include (i) serine and threonine of the aliphatic-hydroxy family; (ii) asparagine and glutamine of the amide-containing family; (iii) alanine, valine, leucine and isoleucine of the aliphatic family; and (iv) phenylalanine, tryptophan and tyrosine of the aromatic family. In some embodiments, conservative amino acid substitution groups are valine-leucine-isoleucine, phenylalanine-tyrosine, lysine-arginine, alanine-valine, glutamic acid-aspartic acid, and asparagine-glutamine. For example, it is reasonable to expect that the single replacement of leucine with isoleucine or valine, aspartate with glutamate, threonine with serine, or the similar replacement of an amino acid with a structurally related amino acid, will not have a major effect on the binding or properties of the resulting molecule, particularly when the replacement does not involve an amino acid within a binding site. Whether an amino acid change results in a functional peptide can be readily determined by determining the specific activity of the polypeptide derivative. The determination is described in detail herein. Fragments or analogs of antibodies or immunoglobulin molecules can be readily prepared by those of ordinary skill in the art.

In some embodiments, the amino acid substitutions have the following effects: (1) reducing susceptibility to proteolysis, (2) reducing susceptibility to oxidation, (3) altering the binding affinity for formation of protein complexes, (4) altering binding affinity, and (5) conferring or improving other physicochemical or functional properties of such analogs. Analogs can include various muteins whose sequences differ from the naturally occurring peptide sequences. For example, single or multiple amino acid substitutions (preferably conservative amino acid substitutions) may be made in the naturally occurring sequence (preferably in a portion of the polypeptide outside the domains that form intermolecular contacts). A conservative amino acid substitution should not significantly alter the structural characteristics of the parent sequence (e.g., a replacement amino acid should not tend to disrupt a helix that occurs in the parent sequence, or disrupt other types of secondary structures that characterize the parent sequence). Examples of secondary and tertiary structures of artificially recognized polypeptides are described in Proteins, Structures and Molecular Principles (Ed. Creighton, W. H. Freeman and Company, New York (1984)); Introduction to Protein Structure (Eds. C. Branden and J. Tooze, Garland Publishing, New York, N.Y. (1991)); and Thornton et al., Nature 354: 105 (1991).

The term "agent" as used herein means a chemical compound, a mixture of chemical compounds, a biological macromolecule, or an extract made from biological material.

As used herein, the term "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or having enzymatic activity that can be detected by optical or calorimetric methods). In certain instances, the label or labels may also be therapeutic. Various methods for labeling polypeptides and glycoproteins are known in the art and can be used. Examples of labels for polypeptides include, but are not limited to: radioisotopes or radionuclides (e.g., $^{3}H$, $^{14}C$, $^{15}N$, $^{35}S$, $^{90}Y$, $^{99}Tc$, $^{111}In$, $^{125}I$ and $^{131}I$), fluorescent labels (e.g., FITC, rhodamine and lanthanide phosphor), enzymatic labels (e.g., horseradish peroxidase, β-galactosidase, luciferase and alkaline phosphatase), chemiluminescent labels, biotinyl groups and predetermined polypeptide epitopes recognized by secondary reporter genes (e.g., leucine zipper pair sequences, secondary antibody-binding sites, metal binding domains and epitope tags). In some embodiments, the labels are connected by spacer arms of various lengths to reduce potential steric hindrance.

The term "agent" or "drug" refers to a compound or composition that is capable of inducing the desired therapeutic effect when properly administered to a patient.

The term "antitumor agent" as used herein refers to an agent having the functional property of inhibiting in a human the development or progression of a tumor, particularly a malignant (cancerous) lesion, such as cancer, sarcoma, lymphoma or leukemia. Inhibition of metastasis is a property of antineoplastic drugs in many cases.

Other chemical terms herein are used according to conventional usage in the art, such as The McGraw-Hill Dictionary of Chemical Terms (Ed. Parker, S., McGraw-Hill, San Francisco (1985)).

CD47 Antibody

The antibodies disclosed herein have the ability to bind to CD47 to inhibit the binding of SIRPα to CD47, to reduce CD47-SIRPα-mediated signaling, to promote phagocytosis, and to inhibit tumor growth and/or metastasis. For example, inhibition can be determined using the cellular assay described herein in the examples.

Exemplary antibodies disclosed herein include Antibody 17, Antibody L12, Antibody 6Y-G1, Antibody 6Y-G4, etc., as well as other similar antibodies having the same or similar CDR regions.

The VH CDRs of Antibody 17 include SEQ ID NO: 14 (VH CDR1), SEQ ID NO: 17 (VH CDR2) and SEQ ID NO: 23 (VH CDR3), and the VL CDRs include SEQ ID NO: 31

(VL CDR1), SEQ ID NO: 33 (VL CDR2) and SEQ ID NO: 35 (VL CDR3). The VH CDRs are the hypervariable regions of the heavy chains and the VL CDRs are the hypervariable regions of the light chains.

In some embodiments, the present invention makes substitutions at one or more amino acid sites of VH CDR1, VH CDR2 and/or VH CDR3 based on Antibody 17. In some embodiments, the substitutable sites (parents) of VH CDR1, VH CDR2 and/or VH CDR3 and the amino acids that can be used for substitution are shown in one or more in Table 1. "Position" in Table 1 represents amino acid sites of the amino acid sequence set forth in SEQ ID NO: 11 numbered from left to right; for example, position 30 represents the 30th amino acid "D", from left to right, in the amino acid sequence set forth in SEQ ID NO: 11.

TABLE 1

Heavy chain CDR amino acid substitutions

| Structure | Position | Parent | Amino acid(s) available for substitution |
|---|---|---|---|
| VH CDR1 | 30 | D | A, G, N, S, T |
| | 31 | N | D, G, S |
| | 33 | Y | A, C, D, E, G, S, W |
| | 35 | S | H, N, R |
| VH CDR2 | 50 | Y | A, C, D, E, F, G, I, K, L, M, N, R, S, T, V, W |
| | 52 | Y | A, D, N, S, T |
| | 53 | Y | C, D, G, N, S |
| | 54 | S | D, G, N |
| | 55 | G | S |
| | 56 | N | A, D, G, S, T |
| VH CDR3 | 98 | G | A, C, D, H, P, R, S, Y |
| | 99 | G | A, C, D, F, H, L, P, R, S, V, Y |
| | 100 | R | A, C, D, F, G, H, I, L, N, P, S, T, V, Y |
| | 101 | F | A, C, D, G, H, I, L, N, P, R, S, T, V, Y |
| | 102 | L | A, C, D, F, G, H, I, N, P, R, S, T, V, Y |
| | 103 | E | A, C, D, F, G, I, K, L, M, N, R, S, T, V, W, Y |
| | 104 | R | D, G, H |

The VH CDRs of Antibody L12 and Antibody L12-6 include SEQ ID NO: 14 (VH CDR1), SEQ ID NO: 17 (VH CDR2) and SEQ ID NO: 23 (VH CDR3), and the VL CDRs include SEQ ID NO: 30 (VL CDR1), SEQ ID NO: 32 (VL CDR2) and SEQ ID NO: 34 (VL CDR3).

It has been confirmed by experiment that the VH CDR1 sequence may also be SEQ ID NO: 15 or 16. The VH CDR2 sequence may also be SEQ ID NO: 18, 19, 20, 21 or 22. The VH CDR3 sequence may also be SEQ ID NO: 24, 25, 26, 27, 28 or 29. Other CDR sequences can be achieved by amino acid substitutions as shown in Table 1. In some embodiments, 1, 2 or 3 amino acids are substituted.

In addition to changes in the CDRs, proper changes can also be made to the amino acids of framework regions. For example, L12-1-VH, L12-2-VH, L12-3-VH, L12-6-1-VH, L12-6-VH, L12-8-VH or L12-9-VH produced by making two mutations (R81K and R82aS) relative to the framework region of the heavy chain of Antibody L12 is also a suitable heavy chain variable region. In some embodiments, the heavy chain variable region of the CD47 antibody may have a K at position 81 or an S at position 82a (according to Kabat numbering). Other framework region mutations are also present in different antibody sequences. Accordingly, the present invention provides heavy chain framework regions having R81K and/or R82aS (according to Kabat numbering) mutations.

Exemplary antibodies of the present invention include ones that comprise a heavy chain variable region of a sequence selected from SEQ ID NOs: 11, 36-44, 50 and 56 and a light chain variable region of a sequence selected from SEQ ID NOs: 12-13, 45-49, 51-55 and 65. In particular, exemplary antibodies include Antibody 17, Antibody 3-3, Antibody 3-6, Antibody 3, Antibody 6, Antibody 10, Antibody 11, Antibody 16, Antibody 18, Antibody 24, Antibody 25, Antibody L1, Antibody L2, Antibody L5, Antibody L12-1-1, Antibody L12, Antibody L24, Antibody L26, Antibody L12-1, Antibody L12-2, Antibody L12-3, Antibody L12-4, Antibody L12-5, Antibody L12-6-1, Antibody L12-6, Antibody L12-7, Antibody L12-8, Antibody L12-9, Antibody L12-10 and Antibody L12-11, and also ones with suitable sequence identity to the sequences of the antibodies described above, for example, sharing at least 80% sequence identity, preferably at least 90% sequence identity, more preferably at least 95% sequence identity, and most preferably at least 99% sequence identity. In some embodiments, these sequences with identity at least do not have varied CDRs.

In some embodiments, Antibody L12 is subjected to human framework adaptation. In some embodiments, framework mutations for the VH of Antibody L12 are shown as the underlined amino acids of L12-1-VH, L12-2-VH, L12-3-VH, L12-6-1-VH, L12-6-VH, L12-8-VH or L12-9-VH in Table 3. In some embodiments, framework mutations for the VL of Antibody L12 are shown as the underlined amino acids of L12-1-1-VL, L12-1-VL, L12-2-VL, L12-3-VL, L12-4-VL, L12-5-VL, L12-6-1-VL, L12-7-VL, L12-8-VL, L12-9-VL, L12-10-VL or L12-11-VL in Table 3.

The present invention further comprises an antibody that binds to the same epitope as the anti-CD47 antibodies disclosed herein. For example, the antibodies disclosed herein specifically bind to an epitope that comprises one or more amino acid residues on human CD47 (see, e.g., GenBank accession No. Q08722.1).

Provided below is an exemplary human CD47 ECD amino acid sequence SEQ ID NO: 1 (GenBank accession No. Q08722.1 (GI: 1171879)), which is incorporated herein by reference. The signal sequence (amino acids 1-18) is underlined.

SEQ ID NO: 1

MWPLVAALLLGSACCGSAQLLFNKTKSVEFTFCNDTVVIPCFVTNMEAQN

TTEVYVKWKFKGRDIYTFDGALNKSTVPTDFSSAKIEVSQLLKGDASLKM

DKSDAVSHTGNYTCEVTELTREGETIIELKYRVVSWFSP

The ability of the antibodies disclosed herein to modulate, block, inhibit, reduce, antagonize, neutralize or otherwise interfere with CD47- and/or CD47/SIRPα-mediated signaling can be assessed using methods including measuring CD47- and/or CD47/SIRPα-mediated signaling in the presence of one or more antibodies described herein. These assays can include competitive binding assays or can measure a biological readout, for example, the ability to promote phagocytosis of CD47-expressing cells by macrophages (as described in Example 3).

The antibodies disclosed herein can be produced using various methods known in the art (e.g., Antibodies: A Laboratory Manual, Harlow E and Lane D, 1988, Cold Spring Harbor Laboratory Press, Cold Spring Harbor, N.Y., which is incorporated herein by reference). Fully human antibodies are antibody molecules in which the entire sequences (including the CDRs) of both the light and heavy chains are derived from a human gene. Such antibodies are referred to herein as "human antibodies" or "fully human antibodies". Human monoclonal antibodies can be produced by using the trioma technique, the human B-cell hybridoma technique (see Kozbor et al., 1983 Immunol Today 4:72), and the EBV hybridoma technique (see Cole et al., 1985. In: *Monoclonal Antibodies And Cancer Therapy*, Alan R. Liss, Inc., pp. 77-96) to produce human monoclonal antibodies. Human monoclonal antibodies can be utilized and can be produced by using human hybridomas (see Cote et al., 1983. Proc Natl Acad Sci USA 80:2026-2030) or by transforming human B-cells with Epstein Barr Virus in vitro (see Cole et al., 1985. In: *Monoclonal Antibodies And Cancer Therapy*, Alan R. Liss, Inc., pp. 77-96).

Antibodies can be purified by known techniques, such as affinity chromatography using protein A or protein G, which provides primarily the IgG fraction of immune serum. In addition, the specific antigen targeted by the immunoglobulin, or an epitope thereof, can be immobilized on a column to purify the immune specific antibody by immunoaffinity chromatography. For purification of immunoglobulins, reference can be made to the D. Wilkinson's article (*The Scientist*, published by the Scientist, Inc., Philadelphia Pa., Vol. 14, No. 8 (Apr. 17, 2000), pp. 25-28).

The CD47 antibodies disclosed herein can be monoclonal antibodies. Monoclonal antibodies that modulate, block, inhibit, reduce, antagonize, neutralize or otherwise interfere with CD47- and/or CD47/SIRPα-mediated cell signaling are produced, for example, by immunizing an animal with, for example, membrane-bound and/or soluble CD47 (e.g., human CD47 or an immunogenic fragment, derivative or variant thereof). Alternatively, the animal is immunized with cells transfected with a vector containing a nucleic acid molecule encoding CD47 such that CD47 is expressed and associated with the surface of the transfected cells. Alternatively, the antibodies are obtained by screening a library that contains antibody or antigen-binding domain sequences for binding to CD47. The library is prepared by expressing fusions of the proteins or peptides fused with the phage coat protein on the surface of assembled phage particles and incorporating encoding DNA sequences into the phage particles (i.e., "phage displayed library"). Screening was then performed by binding reaction with CD47.

For preparing monoclonal antibodies using, for example, hybridoma methods, see, e.g., those described by Kohler and Milstein, *Nature,* 256:495 (1975). In the hybridoma method, a mouse, a hamster or other appropriate host animal, is typically immunized with an immunizing agent to elicit lymphocytes that produce or are capable of producing antibodies that specifically bind to the immunizing agent. Alternatively, the lymphocytes can be immunized in vitro.

The immunizing agent generally includes a protein antigen, a fragment thereof or a fusion protein thereof. Generally, if a human cell is desired, a peripheral blood lymphocyte is used, or if a cell of non-human mammalian origin is desired, a spleen cell or lymph node cell is used. The lymphocyte is then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually rat or mouse myeloma cell lines. The hybridoma cell may be cultured in a suitable culture medium preferably containing one or more substances that inhibit the growth or survival of unfused immortalized cells. For example, if the parent cells lack hypoxanthine-guanine phosphoribosyltransferase (HGPRT or HPRT), the culture medium for the hybridoma generally contains hypoxanthine, aminopterin and thymine ("HAT medium"), which prevent the growth of HGPRT-deficient cells.

The monoclonal antibody can also be prepared by recombinant DNA methods, such as those described in U.S. Pat. No. 4,816,567. DNA encoding the monoclonal antibody disclosed herein can be isolated and sequenced using conventional methods (e.g., by using oligonucleotide probes that can specifically bind to genes encoding the heavy and light chains of murine antibodies). The hybridoma cell described herein serves as a preferred source of such DNA. Once isolated, the DNA can be placed into expression vectors, which are then transfected into a host cell such as a Chinese hamster ovary (CHO) cell, a human embryonic kidney (HEK) 293 cell, a simian COS cell, a PER. NS0 cell, a SP2/0 cell, a YB2/0 cell or a myeloma cell that does not otherwise produce immunoglobulins, thereby obtaining a synthetic monoclonal antibody in the recombinant host cell. The DNA can also be modified, for example, by substituting the coding sequence for human heavy and light chain constant domains for the homologous murine sequences (see U.S. Pat. No. 4,816,567; Morrison, *Nature* 368, 812-13 (1994)) or by covalently linking the immunoglobulin coding sequence to all or part of the coding sequence for a non-immunoglobulin polypeptide. Such a non-immunoglobulin polypeptide can be substituted for the constant domains of the antibodies disclosed herein, or can be substituted for the variable domains of one antigen-binding site of the antibodies disclosed herein to produce chimeric bivalent antibodies.

Antibody-producing cell lines can be selected, constructed and cultured using techniques well known to those skilled in the art. These techniques are described in various laboratory manuals and main publications, such as Recombinant DNA Technology for Production of Protein Therapeutics in Cultured Mammalian Cells, D. L. Hacker, F. M. Wurm, *Reference Module in Life Sciences,* 2017, which is incorporated by reference in its entirety, including the supplements.

In some embodiments, the DNA encoding the antibody can be designed and synthesized according to the antibody amino acid sequence described herein by conventional methods, inserted into an expression vector, and transfected into a host cell. The transfected host cell is then cultured in a medium to produce the monoclonal antibody. In some embodiments, the vector expressing the antibody comprises at least one promoter element, an antibody coding sequence, a transcription termination signal and a poly-A tail. Other elements include enhancers, Kozak sequences, and donor and recipient sites flanking the inserted sequence for RNA splicing. Efficient transcription can be obtained by early and late promoters of SV40, long terminal repeats from retroviruses such as RSV, HTLV1 and HIVI, and early promoters of cytomegalovirus, and promoters from other cells such as actin promoter can also be used. Suitable expression vectors may include pIRES1neo, pRetro-Off, pRetro-On, PLXSN, or Plncx, pcDNA3.1 (+/−), pcDNA/Zeo (+/−), pcDNA3.1/Hygro (+/−), PSVL, PMSG, pRSVcat, pSV2dhfr, pBC12MI, pCS2, etc. Commonly used mammalian cells include 293 cells, Cos1 cells, Cos7 cells, CV1 cells, murine L cells, CHO cells and the like.

In some embodiments, the inserted gene fragment should comprise a screening label, common ones of which include screening genes such as dihydrofolate reductase, glutamine synthetase, neomycin resistance and hygromycin resistance, to facilitate the screening and separation of cells that have been successfully transfected. The constructed plasmid is transfected to a host cell without the above genes, and the successfully transfected cells are cultured in large quantities in a selective culture medium to produce the desired target protein.

In some embodiments, the DNA sequences encoding the CD47 antibodies disclosed herein can be obtained using the amino acid sequences of the antibodies in combination with the conventional methods in the art. In some embodiments, the DNA sequence encoding the heavy chain of Antibody 6Y-G4 is set forth in SEQ ID NO: 57, wherein the underlined portions encode VH CDRs; the amino acid sequence encoding the heavy chain of Antibody 6Y-G4 is set forth in SEQ ID NO: 60.

SEQ ID NO: 57 is shown below:

```
caggtgcagctgcaggagtccggccctggcctggtgaagccttccgagac

cctgtccctgacctgtaccgtgagcggcggcagcctggataactattact

ggagctggatccggcagcctcctggcaagggcctggagtggatcggctac

atctactattccggcaacaccaattacaacccttccctgaagagccgggt

gaccatctccgtggacaccagcaagaaccagtttagcctgaagctgtcct

ccgtgaccgccgctgataccgccgtgtactactgtgccagggcggccgg

ttctggagagatattggggccagggtaccctcgtgaccgtgtccagcgct

agcaccaagggcccttccgtgttcccccctggccccctgtagccggtccac

ctctgagagcaccgctgctctgggctgtetggtgaaggattactttcccg

aaccggtgaccgtgtcatggaactccggggctctgacatccggtgtccac

acttttcctgcagtgctgcagtcatccggcctgtacagcctgagctctgt

ggtcacagtcccaagttcatccctgggaaccaagacatatacttgcaacg

tggatcataaacccagcaatactaaggtcgacaaacgagtggagtctaag

tacggaccaccttgcccaccatgtccagcacctgagttcctgggaggacc

aagcgtgttcctgtttcctccaaagcctaaagataccctgatgatcagtc

ggactcccgaggtcacctgcgtggtcgtggacgtgtcccaggaggaccct

gaagtccagttcaactggtacgtggacggcgtcgaagtgcacaatgctaa

gacaaaacctcgagaggaacagtttaactccacataccgtgtcgtgagcg

tcctgactgtgctgcatcaggattggctgaacggcaaggagtataagtgc

aaagtgagcaataagggactgccaagctctatcgagaaaactatttctaa

ggctaaaggacagcctagggaaccacaggtgtacaccctgcccccctagtc

aggaggaaatgactaagaaccaggtctcactgacctgtctggtgaaaggg

ttctatccttcagatattgcagtggagtgggaatccaatggtcagccaga

gaacaattacaagacaactccaccegtgctggacagcgatgggtctttct

ttctgtattctagactgaccgtggacaaaagtcgctggcaggagggtaat

gtcttttcttgtagtgtgatgcacgaagccctgcacaaccactacactca

gaaaagcctgtcactgtccctgggtaaa
```

```
SEQ ID NO: 60:
QVQLQESGPGLVKPSETLSLTCTVSGGSLDNYYWSWIRQPPGKGLEWIGY

IYYSGNTNYNPSLKSRVTISVDTSKNQFSLKLSSVTAADTAVYYCARGGR

FLERYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTCN
```

-continued

```
VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGK
```

In some embodiments, the DNA sequence encoding the light chain of Antibody 6Y-G4 is set forth in SEQ ID NO: 58, wherein the underlined portions encode VL CDRs; the amino acid sequence encoding the light chain of Antibody 6Y-G4 light chain is set forth in SEQ ID NO: 61.

SEQ ID NO: 58 is shown below:

```
gagatcgtgctgacccagtcccccctccagcctgagcgccagcgtgggaga

ccgggtgaccatcccctgccgggcttccctgtccatcggcagcttcctga

actggtatcagcagaggcctggcgaggcccctaagctgctgatctttgcc

gcttccagcctgcggagcggcgtgcctagcaggttctccggcagcggctc

cggcaccgatttcaccctgaccatcagcggcctgcagcccgaggatttcg

ccacctactactgccagcagacctacaccaccccttacacctttggccag

ggcaccaaggtggacatcaagcgtacggtggctgcaccatctgtcttcat

cttcccgccatctgatgagcagttgaaatctggaactgcctctgttgtgt

gcctgctgaataacttctatcccagagaggccaaagtacagtggaaggtg

gataacgccctccaatcgggtaactcccaggagagtgtcacagagcagga

cagcaaggacagcacctacagcctcagcagcaccctgacgctgagcaaag

cagactacgagaaacacaaagtctacgcctgcgaagtcacccatcagggc

ctgagctcgcccgtcacaaagagcttcaacaggggagagtgttga
```

```
SEQ ID NO: 61:
EIVLTQSPSSLSASVGDRVTIPCRASLSIGSFLNWYQQRPGEAPKLLIFA

ASSLRSGVPSRFSGSGSGTDFTLTISGLQPEDFATYYCQQTYTTPYTFGQ

GTKVDIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In some embodiments, the amino acid sequence of the heavy chain of Antibody 6Y-G1 is set forth in SEQ ID NO: 62.

```
SEQ ID NO: 62:
QVQLQESGPGLVKPSETLSLTCTVSGGSLDNYYWSWIRQPPGKGLEWIGY

IYYSGNTNYNPSLKSRVTISVDTSKNQFSLKLSSVTAADTAVYYCARGGR

FLERYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGOPENNYKTTPPVLDSD

GSFFLYSKLTVDKSRWQQGNVFSCSVMHEALHNHYTQKSLSLSPGK
```

In some embodiments, the amino acid sequence of the light chain of Antibody 6Y-G1 is set forth in SEQ ID NO: 61.

In some embodiments, the amino acid sequence of the heavy chain of Antibody 17 is set forth in SEQ ID NO: 63.

```
SEQ ID NO: 63:
QVQLQESGPGLVKPSETLSLTCTVSGGSLDNYYWSWIRQPPGKGLEWIGY

IYYSGNTNYNPSLKSRVTISVDTSKNQFSLRLRSVTAADTAVYYCARGGR

FLERYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK
```

In some embodiments, the amino acid sequence of the light chain of Antibody 17 is set forth in SEQ ID NO: 64.

```
SEQ ID NO: 64:
DIQMTQSPSSVSASVGDRVTISCRANQAIGTWLAWYQQKPGKAPKLLIYA

ASTLQSGVPSRFSGSGSGTEFTLTISSLQAEDVAVYYCQQYYTTPLTFGG

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In some embodiments, the amino acid sequence of the heavy chain of Antibody L12 is set forth in SEQ ID NO: 63. In some embodiments, the amino acid sequence of the light chain of Antibody L12 is set forth in SEQ ID NO: 61.

Human Antibody and Humanized Antibody

The antibodies disclosed herein include fully human antibodies or humanized antibodies. These antibodies are suitable for administration to humans without causing immune responses in humans to the administered immunoglobulins.

The CD47 antibodies are produced, for example, through phage display methods using antibodies that contain only human sequences. Such methods are well known in the art, for example, in WO92/01047 and U.S. Pat. No. 6,521,404. In this method, a natural or recombinant CD47 or a fragment thereof is used to screen a combinatorial library of phage carrying random pairs of light and heavy chains. In another approach, the CD47 antibodies can be produced through a method in which at least one step comprises immunizing a transgenic non-human animal with human CD47 protein. In such approaches, some of the endogenous heavy and/or k light chain loci of transgenic non-human animals have been disabled and are incapable of the rearrangement required to produce genes encoding immunoglobulins in response to an antigen. In addition, at least one human heavy chain locus and at least one human light chain locus have been stably transfected into the animal. Thus, in response to the administered antigen, the human loci rearrange to provide genes encoding human variable regions immunospecific for the antigen. Thus, the transgenic mouse produces, upon immunization, B cells that secrete fully human immunoglobulins.

The production of antibodies with reduced immunogenicity is also achieved via humanization techniques, chimerization techniques and display techniques using appropriate libraries. It should be understood that murine antibodies or antibodies from other species can be humanized or primatized using techniques well known in the art. See, e.g., Winter and Harris *Immunol Today* 14:43 46 (1993) and Wright et al., *Crit. Reviews in Immunol.* 12125-168 (1992). The antibodies of interest can be engineered by recombinant DNA techniques to substitute CH1, CH2, CH3, hinge domains and/or framework domains with the corresponding human sequences (see WO 92102190 and U.S. Pat. Nos. 5,530,101; 5,585,089; 5,693,761; 5,693,792; 5,714,350 and 5,777,085). The use of Ig cDNAs for the construction of chimeric immunoglobulin genes is also known in the art (Liu et al., *P.N.A.S.* 84:3439 (1987) and *J. Immunol.* 139: 3521 (1987)). mRNA is isolated from hybridomas or other cells that produce the antibody and used to produce cDNA. The cDNA of interest can be amplified by polymerase chain reaction using specific primers (U.S. Pat. Nos. 4,683,195 and 4,683,202). Alternatively, a library is constructed and screened to isolate the sequence of interest. The DNA sequences encoding the variable regions of the antibody are then fused to human constant region sequences. The sequences of the human constant region genes can be found in Kabat et al., Sequences of Proteins of immunological Interest (N.I.H. publication no. 91-3242 (1991)). The human C region genes can be readily obtained from known clones. The choice of isotype will be guided by the desired effector functions, such as activity of complement fixation or activity in antibody-dependent cellular cytotoxicity. Preferred isotypes are IgG1 and IgG2. Either of the human light chain constant regions, i.e., k or 2, can be used, and the chimeric humanized antibody is then expressed using conventional methods.

In some embodiments, antibody fragments such as Fv, F(ab')2 and Fab can be prepared by cleavage of an intact protein, e.g., by using protease or chemical cleavage, including but not limited to: (i) digesting the antibody molecule with pepsin to obtain a F(ab')2 fragment; (ii) obtaining a Fab fragment by reducing the disulfide bond of the F(ab')2 fragment; (iii) treating the antibody molecule with papain and a reducing agent to produce a Fab fragment, and (iv) a Fv fragment.

The consensus sequence J region of the heavy and light chains can be used to design oligonucleotides for use as primers to introduce useful restriction sites into the J region for subsequent linkage of V region fragments to human C region fragments. The C region cDNA can be modified by site-directed mutagenesis to place a restriction site at a similar position in the human sequence.

The CD47 antibodies disclosed herein can be expressed by vectors comprising DNA fragments encoding the antibodies described above, including plasmids, retroviruses, YAC, EBV-derived episomes and the like. A suitable vector is typically one that encodes a functionally complete human heavy chain constant region (CH) or light chain constant region (CL) immunoglobulin sequence, with appropriate restriction sites so that any VH or VL sequence can be readily inserted and expressed. In such vectors, splicing typically occurs between the splice donor site in the inserted J region and the splice acceptor site before the human C region, and also at the splice regions that occur within the human CH exons. Polyadenylation and transcription termination occur at natural chromosomal sites downstream of the coding regions. The resulting chimeric antibody can be linked to any strong promoter, including retroviral LTRs, such as the SV-40 early promoter (Okayama et al., *Mol. Cell. Bio.* 3: 280 (1983)), Rous sarcoma virus LTR (Gorman et al., *P.N.A.S.* 79: 6777 (1982)), and Moloney murine leukemia virus LTR (Grosschedl et al., *Cell* 41:885 (1985)). In addition, natural Ig promoters and the like can be used.

Fc Modification

Relevant effector functions of the antibodies disclosed herein can be modified to improve, for example, the efficacy of the antibodies in treating diseases and disorders associated with CD47 signaling. For example, one or more mutations can be introduced into the Fc region of the antibody to silence effector function, thereby reducing the likelihood of killing normal cells.

In some embodiments, the antibody described herein is of the IgG isotype. In some embodiments, a constant region of the antibody is of a human IgG1 isotype and has an amino acid sequence set forth in SEQ ID NO: 3. In some embodiments, amino acid Asn297 (Kabat numbering) on the constant region of human IgG1 is modified to avoid glycosylation of the antibody, e.g., Asn297Ala (N297A). In some embodiments, amino acid Leu235 (Kabat numbering) on the antibody constant region is modified to alter Fc receptor interactions, e.g., Leu235Glu (L235E) or Leu235Ala (L235A). In some embodiments, amino acid Leu234 (Kabat numbering) on the antibody constant region is modified to alter Fc receptor interactions, e.g., Leu234Ala (L234A). In some embodiments, amino acids 234 and 235 on the antibody constant region are modified simultaneously, e.g., Leu234Ala and Leu235Ala (L234A/L235A) (EU indexes in Kabat et al., 1991, Sequences of Proteins of Immunological Interest).

In some embodiments, a constant region of the antibody is of a human IgG4 isotype and has an amino acid sequence set forth in SEQ ID NO: 4.

In some embodiments, the hinge region within the human IgG4 constant region is modified to avoid or reduce chain exchange, e.g., Ser228Pro (S228P). In other embodiments, amino acid 235 on the human IgG4 constant region is modified to alter Fc receptor interactions, e.g., Leu235Glu (L235E). In some embodiments, the hinge region and amino acids 235 within the constant region of human IgG4 are modified, e.g., Ser228Pro and Leu235Glu (S228P/L235E). In some embodiments, amino acid Asn297 (boxed, Kabat numbering) on the constant region of human IgG4 is modified to avoid glycosylation of the antibody, e.g., Asn297Ala (N297A). In some embodiments, amino acids Ser228, Leu235 and Asn297 on the human IgG4 constant region are modified (e.g., S228P/L235E/N297A).

Use of Antibodies Against CD47

In some embodiments, CD47 antibodies including the present invention can be used to diagnose, prognose, monitor, treat, alleviate and/or prevent a disease or pathology associated with abnormal CD47 expression, activity and/or signaling in a subject. A treatment regimen can be carried out by identifying a subject (e.g., a human patient) suffering from a disease or condition associated with abnormal CD47 expression, activity and/or signaling (such as cancer or other neoplastic conditions), or at risk of developing a disease, using standard methods. In some embodiments, provided is a method for treating a disease or condition involving abnormal CD47 expression, activity and/or signaling, which comprises administering to a subject in need of treatment for the disease or condition an effective amount of an antibody disclosed herein or a formulation thereof. The administration of the antibody may eliminate or inhibit or interfere with the expression, activity and/or signaling function of the target (e.g., CD47). The administration of the antibody may eliminate or inhibit or interfere with the binding of the target (e.g., CD47) to an endogenous ligand (e.g., SIRPα) to which it naturally binds. For example, the antibody binds to the target and modulates, blocks, inhibits, reduces, antagonizes, neutralizes or interferes with CD47 expression, activity and/or signaling.

In some embodiments, the disease or condition involving abnormal CD47 expression, activity, and/or signaling includes hematologic cancer and/or a solid tumor. The hematologic cancers include, for example, leukemia, lymphoma and myeloma. In some embodiments, certain forms of leukemia include acute lymphocytic leukemia (ALL), acute myelogenous leukemia (AML), chronic lymphocytic leukemia (CLL), chronic myelogenous leukemia (CML) and myeloproliferative diseases/tumors (MPDs) and myelodysplastic syndrome. In some embodiments, certain forms of lymphoma include Hodgkin lymphoma, indolent and aggressive non-Hodgkin lymphoma, Burkitt lymphoma and follicular lymphoma (small cell and large cell). In some embodiments, certain forms of myeloma include multiple myeloma (MM), giant cell myeloma, heavy chain myeloma, and light chain or Bence-Jones myeloma. The solid tumor includes, for example, breast cancer, ovarian cancer, lung cancer, pancreatic cancer, prostate cancer, melanoma, colorectal cancer, lung cancer, head and neck cancer, bladder cancer, esophageal cancer, liver cancer and renal cancer.

Symptoms associated with cancer and other neoplastic conditions include, for example, inflammation, fever, general malaise, fever, pain, often localized to the inflamed area, loss of appetite, weight loss, edema, headache, fatigue, rash, anemia, muscle weakness, muscle fatigue and abdominal symptoms (e.g., abdominal pain, diarrhea, or constipation).

A therapeutically effective amount of the antibody disclosed herein typically relates to an amount required to achieve a therapeutic goal. The amount required for administration depends on the binding affinity of the antibody for its specific antigen, the severity of the disease, disorder or condition, the route of administration, the rate at which the antibody administered in the subject is depleted from free volume, and the like. In some embodiments, a common range of the therapeutically effective dose of the antibody or the antibody fragment disclosed herein is from about 0.1 mg/kg to about 100 mg/kg. In some embodiments, the antibody disclosed herein is administered to a subject at a dose of about 0.1 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 50 mg/kg, about 75 mg/kg, about 100 mg/kg or more, or a range between any two of these values (inclusive). The common dosing frequency ranges, for example, from once daily to once weekly.

In other embodiments, antibodies against CD47 can be used in methods known in the art related to CD47 localization and/or quantification (e.g., for determining the level of CD47 and/or both CD47 and SIRPα in a suitable physiological sample, for diagnostic methods, for protein imaging, etc.). In a given embodiment, an antibody that comprises an antigen-binding domain derived from an antibody and that is specific for CD47 or a derivative, fragment, analog or homolog thereof is used as a pharmaceutically active compound (hereinafter "therapeutic agent").

In other embodiments, CD47 polypeptides can be isolated using antibodies specific for CD47 via standard techniques such as immunoaffinity, chromatography or immunoprecipitation. Antibodies (or fragments thereof) against the CD47 protein can be used to detect the proteins in biological samples. In some embodiments, CD47 may be detected in a biological sample as part of a clinical testing procedure, e.g., to determine the efficacy of a given treatment regimen. Coupling (i.e., physically linking) the antibody to a detectable substance can facilitate detection. Examples of detectable substances include various enzymes, prosthetic groups, fluorescent materials, luminescent materials, bioluminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; one example of a luminescent material includes luminol; examples of bioluminescent materials include luciferase, luciferin and aequorin, and examples of suitable radioactive materials include $^{125}I$, $^{131}I$, $^{35}S$ or $^{3}H$.

In other embodiments, the antibodies disclosed herein can be used as agents for detecting the presence of CD47 and/or both CD47 and SIRPα proteins (or protein fragments thereof) in a sample. In some embodiments, the antibodies comprise a detectable label. The antibodies are polyclonal antibodies, or more preferably monoclonal antibodies. An intact antibody or a fragment thereof (e.g., Fab, scFv, or F(ab')2) is used. The detection method of the embodiments can be used to detect an analyte mRNA, protein or genomic DNA in a biological sample in vitro as well as in vivo. For example, in vitro detection techniques for detecting an analyte mRNA include Northern hybridization and in situ hybridization. In vitro detection techniques for detecting an analyte protein include enzyme-linked immunosorbent assays (ELISAs), Western blots, immunoprecipitations and immunofluorescence. In vitro detection techniques for detecting an analyte genomic DNA include Southern hybridization. (*ELISA: Theory and Practice: Methods in Molecular Biology*, Vol. 42, J. R. Crowther Human Press, Totowa, N. J., 1995; *Immunoassay*, E. Diamandis and T. Christopoulus, Academic Press, Inc., San Diego, Calif., 1996; *Practice and Theory of Enzyme Immunoassays*, P. Tijssen, Elsevier Science Publishers, Amsterdam, 1985). In addition, in vivo techniques for detecting an analyte protein include introducing a labeled anti-analyte protein antibody into a subject. For example, the antibody can be labeled with a radioactive marker, the presence and location of which in the subject can then be detected by standard imaging techniques.

Therapeutic Administration and Formulation of CD47 Antibody

The antibodies disclosed herein and derivatives, fragments, analogs and homologs thereof can be incorporated into pharmaceutical compositions suitable for administration. The principles and considerations involved in preparing such compositions, as well as guidelines in the choice of components, are well known in the art, see, e.g., *Remington's Pharmaceutical Sciences: The Science And Practice Of Pharmacy*, the 19th edition, Mack Pub. Co., Easton, Pa.: 1995; *Drug Absorption Enhancement: Concepts, Possibilities, Limitations, And Trends*, Harwood Academic Publishers, Langhorne, Pa., 1994; and *Peptide And Protein Drug Delivery, Advances In Parenteral Sciences*, Vol. 4, 1991, M. Dekker, New York.

Such compositions typically comprise the antibody and a pharmaceutically acceptable carrier. In some embodiments, an antibody fragment is used as the smallest inhibitory fragment that specifically binds to the binding domain of the target protein. For example, a peptide that is based on the variable region sequence of an antibody and retains the ability to bind to a target protein sequence is used.

As used herein, the term "pharmaceutically acceptable carrier" is intended to include any and all solvents, stabilizers, buffers, dispersion media, coatings, antibacterial agents, isotonic and absorption delaying agents, and the like that are compatible with pharmaceutical administration. Suitable carriers are described in the latest edition of Remington's Pharmaceutical Sciences. Such carriers or diluents can include, but are not limited to, water, saline, Ringer's solution, glucose solution and 5% human serum albumin.

The formulations to be used for in vivo administration must be sterile. This can be readily achieved by filtration through sterile filtration membranes.

The pharmaceutical compositions of the embodiments are generally compatible with their intended routes of administration. Examples of the routes of administration include parenteral administration, such as intravenous, intradermal, subcutaneous, oral (e.g., inhalational), transdermal (i.e., topical), transmucosal and rectal administration. The pharmaceutical compositions can comprise one or more of the following components: sterile diluents for injection, such as water, saline solutions, fixed oils, polyethylene glycols, glycerol, propylene glycol or other synthetic solvents; antibacterial agents, such as benzyl alcohol or methylparaben; antioxidants, such as ascorbic acid or sodium bisulfite; chelating agents, such as ethylenediamine tetraacetic acid (EDTA); buffers, such as histidine hydrochloride, acetates, citrates or phosphates; tonicity-adjusting agents, such as sodium chloride or dextrose; stabilizers, such as arginine, methionine, trehalose, sucrose or sorbitol; and surfactants, such as tween 20 or tween 80. The pH can be adjusted with acids or bases, such as hydrochloric acid or sodium hydroxide. The pharmaceutical compositions can be packaged in ampoules, disposable syringes or multiple-dose vials made of glass or plastic. In some embodiments, the pharmaceutical compositions suitable for injection include sterile aqueous solutions (herein water-soluble solutions) or dispersions and sterile powders for the instant preparation of sterile injectable solutions or dispersions. In use, the compositions must be sterile and should be fluid to the extent that easy syringability exists. The composition must be stable under the conditions of manufacture and storage and must be able to prevent the contamination of microorganisms such as bacteria and fungi. Prolonged absorption of the injectable compositions can be brought about by including in the composition an agent which delays absorption, for example, aluminum monostearate and gelatin.

For transmucosal or transdermal administration, penetrants appropriate for the barrier to be permeated are used in the formulation. Such penetrants are generally known in the art, and include, for example, detergents, bile salts and fusidic acid derivatives for transmucosal administration. Transmucosal administration can be accomplished through the use of nasal sprays or suppositories. For transdermal administration, one or more of the antibodies may be formulated into ointments, salves, gels, or creams as generally known in the art.

The pharmaceutical compositions are formulated in dosage unit form for ease of administration and uniformity of dosage. As used herein, dosage unit form refers to physically separable units that are suitable as unitary dosages for a subject to be treated; each unit contains a predetermined amount of one or more of the antibodies calculated to produce the desired therapeutic effect in association with the required pharmaceutical carrier.

The pharmaceutical compositions can be placed in a container or dispenser and packaged together with instructions for administration.

The pharmaceutical compositions disclosed herein can also comprise other active ingredients, preferably those with complementary activities that do not adversely affect each other, depending on the particular condition to be treated. In some embodiments, the compositions can comprise an agent that enhances its function, such as a cytotoxic agent, cytokine, chemotherapeutic agent or growth inhibitory agent. Such active ingredients are suitably present in combination in amounts that are effective for the intended purpose.

In one embodiment, one or more active ingredients, including the CD47 antibodies, can be administered in combination therapy, i.e., in combination with other agents, such as therapeutic agents (e.g., one or more cytokines and growth factor inhibitors, immunosuppressive agents, anti-inflammatory agents, metabolic inhibitors, enzyme inhibitors and/or cytotoxic or cytostatic agents). The term "in combination" as used herein means that the agents are administered substantially contemporaneously, simultaneously or sequentially. In some embodiments, such combination therapies may advantageously utilize lower doses of the administered therapeutic agents, thus avoiding possible toxicities or complications associated with various monotherapies.

In some embodiments, the antibodies disclosed herein are used as vaccine adjuvants against autoimmune disorders, inflammatory diseases, etc. The vaccines can be a wide variety of antigens. The antigens are derived from the targeted autoantigens, i.e., autoantigens involved in autoimmunity, such as myelin basic protein; inflammatory autoantigens, such as amyloid peptide protein or transplant antigens, such as alloantigens. The antigens may comprise peptides or polypeptides derived from proteins, as well as fragments of any of the following: sugars, proteins, polynucleotides or oligonucleotides, autoantigens, amyloid peptide proteins, transplant antigens, allergens or other macromolecular components. In some embodiments, more than one antigen is comprised in the antigenic composition.

Citation of publications and patent documents herein is not intended as an admission that any is pertinent prior art, nor does it constitutes any admission as to the contents or date of the same. Now, the present invention has been described in the written description, and it should be understood by those skilled in the art that the present invention may be practiced in various embodiments. The above specification and the examples below are intended to be illustrative rather than limiting the claims disclosed herein. All the publications, patents, and patent applications cited herein are incorporated herein by reference in their entirety for all purposes.

EXAMPLES

The materials, reagents, etc. used in the following examples can be commercially available or obtained using known methods unless otherwise stated. In the following examples, Antibody L12-6 is the same antibody as Antibody 6Y-G1.

CHO-CD47 cell construction process: a HindIII/EcoRI window was designed to introduce a polynucleic acid encoding CD47 (see Uniprot, Q08722 for the sequence) into the pcDNA3.1(+) (Invitrogen, V790-20) plasmid, and then CHO cells (ATCC #CCL-61) were transfected with the plasmid by single digestion with PvuI. Stable CHO-CD47 cell lines were obtained by screening.

The Jurkat cells were purchased from Cell Bank of Chinese Academy of Sciences, Shanghai, under catalog No. Clone E6-1.

The IgG antibodies was purchased from BioXCell, under catalog No. BE0297.

The macaque CD47-Fc was purchased from Creative BioMart, and its model number was CD47-745C.

Example 1: Preparation of CD47 Antigens

Preparation of CD47 antigens: A CD47 recombinant protein was constructed by adding a 6×HIS tag (HHHHHH, SEQ ID NO: 2) or human Fc (underlined in SEQ ID NO: 3) (referring to R&D system) to the C-terminus of the human CD47 extracellular domain (ECD) protein (SEQ ID NO: 1). The ECD region of human CD47 was genetically synthesized together with 6×HIS or Fc and subcloned into the mammalian expression vector pcDNA3.1(+) (Invitrogen, V790-20).

After transient transfection of HEK293F cells, a His-tagged human CD47-ECD protein (CD47-His) purified by nickel-based immobilized metal affinity chromatography and a secreted Fc-tagged human CD47-ECD protein (CD47-Fc) purified by immobilized metal affinity chromatography (IMAC) using a protein A column (GE Healthcare) were obtained.

Example 2: Preparation of CD47 Antibodies

Combinations of VH and VL for 30 single-chain antibodies (scFvs) are shown in Table 2. The C-terminus of VH and the N-terminus of VL were linked by a linker whose sequence is set forth in SEQ ID NO: 10 (GGGGSGGGGSGGGGS). The heavy chain variable regions of the antibodies are indicated by antibody number+"–VH", e.g., 17-VH; the light chain variable regions of the antibodies are indicated by antibody number+"–VL", e.g., 17-VL; the single-chain antibodies (scFvs) are indicated by antibody number+"–ScFv", e.g., 17-ScFv (which is obtained by linking the C-terminus of 17-VH (set forth in SED ID NO: 11) and the N-terminus of 17-VL (set forth in SED ID NO: 12) by a linker set forth in SED ID NO: 10).

Combinations of VH and VL of 30 full-length IgG1 antibodies are shown in Table 2. VH and CH constitute the heavy chains of the antibodies, and VL and CL constitute the light chains of the antibodies. The sequence of CH is set forth in SED ID NO: 3, and the sequence of CL is set forth in SED ID NO: 5. The heavy chain variable regions of the antibodies are indicated by antibody number+"–VH", e.g., 17-VH; the light chain variable regions of the antibodies are indicated by antibody number+"–VL", e.g., 17-VL; the full-length IgG1 antibodies were indicated by "antibody"+ antibody number, e.g., Antibody 17 (whose heavy chain is composed of 17-VH (set forth in SED ID NO: 11) and the CH set forth in SED ID NO: 3, and whose light chain is composed of 17-VL (set forth in SED ID NO: 12) and the CL set forth in SED ID NO: 5).

The amino acid sequence of the heavy chain of Antibody 6Y-G4 is set forth in SEQ ID NO: 60, and the amino acid sequence of the light chain is set forth in SEQ ID NO: 61.

The corresponding sequences of the VHs and VLs in Table 2 are shown in Table 3. The heavy chain CDRs are shown in Table 4 and the light chain CDRs are shown in Table 5.

Plasmid pcDNA3.1(+) (Invitrogen, V790-20) was engineered using conventional techniques to carry a DNA sequence encoding the above amino acid sequences. The plasmid was then transiently transfected into HEK293F cells, and the HEK293F cells were allowed to express antibodies of the above amino acid sequences. CD47 antibodies were obtained after purification by immobilized metal affinity chromatography (IMAC) using a protein A column (GE Healthcare), and sequencing showed that their sequences were in agreement with the expected ones. They were subjected to biological activity determination.

TABLE 2

| Variable region combinations of antibodies | | |
|---|---|---|
| Antibody number | Heavy chain variable region (VH) SEQ ID NO: | Light chain variable region (VL) SEQ ID NO: |
| 17 | 11 | 12 |
| 3-3 | 36 | 12 |
| 3-6 | 37 | 12 |
| 3 | 38 | 12 |
| 6 | 39 | 12 |
| 10 | 40 | 12 |
| 11 | 56 | 12 |
| 16 | 41 | 12 |
| 18 | 42 | 12 |
| 24 | 43 | 12 |

TABLE 2-continued

| Variable region combinations of antibodies | | |
|---|---|---|
| Antibody number | Heavy chain variable region (VH) SEQ ID NO: | Light chain variable region (VL) SEQ ID NO: |
| 25 | 44 | 12 |
| L1 | 11 | 45 |
| L2 | 11 | 46 |
| L5 | 11 | 47 |
| L12-1-1 | 11 | 13 |
| L12 | 11 | 65 |
| L24 | 11 | 48 |
| L26 | 11 | 49 |
| L12-1 | 50 | 54 |
| L12-2 | 50 | 51 |
| L12-3 | 50 | 53 |
| L12-4 | 11 | 52 |
| L12-5 | 11 | 54 |
| L12-6-1 | 50 | 13 |
| L12-6 | 50 | 65 |
| L12-7 | 11 | 53 |
| L12-8 | 50 | 52 |
| L12-9 | 50 | 55 |
| L12-10 | 11 | 51 |
| L12-11 | 11 | 55 |

TABLE 3

| Antibody variable region sequences | | |
|---|---|---|
| Name | Sequence | SEQ ID NO |
| 17-VH\LI-VH\L2-VH\L5-VH\L12-1-1-VH \L12-VH\L24-VH\L26-VH\L12-4-VH\L12-5-VH\L12-7-VH\L12-10-VH\L12-11-VH | QVQLQESGPGLVKPSETLSLTCTVSGGSLDNYYWSWIRQPPG KGLEWIGYIYYSGNTNYNPSLKSRVTISVDTSKNQFSLRLRS VTAADTAVYYCARGGRFLERYWGQGTLVTVSS | 11 |
| 3-3-VH | QVQLQESGPGLVKPSETLSLTCTVSGGSLDNYYWSWIRQPPG KGLEWIGYIYYSGNTNYNPSLKSRVTISVDTSKNQFSLRLRS VTAADTAVYYCARGGRIFGGYWGQGTLVTVSS | 36 |
| 3-6-VH | QVQLQESGPGLVKPSETLSLTCTVSGGSLDNYYWSWIRQPPG KGLEWIGYIYYSGNTNYNPSLKSRVTISVDTSKNQFSLRLRS VTAADTAVYYCARGGRIFAGYWGQGTLVTVSS | 37 |
| 3-VH | QVQLQESGPGLVKPSETLSLTCTVSGGSLDGYYWSWIRQPPG KGLEWIGRIYGNSTTNYNPSLKSRVTISVDTSKNQFSLRLRSV TAADTAVYYCARGGRIFAGYWGQGTLVTVSS | 38 |
| 6-VH | QVQLQESGPGLVKPSETLSLTCTVSGGSLNDYYWSWIRQPPG KGLEWIGRIYGNGDTNYNPSLKSRVTISVDTSKNQFSLRLRS VTAADTAVYYCARGGRILAGYWGQGTLVTVSS | 39 |
| 10-VH | QVQLQESGPGLVKPSETLSLTCTVSGGSLDNYYWSWIRQPPG KGLEWIGRIYYNGNTNYNPSLKSRVTISVDTSKNQFSLRLRS VTAADTAVYYCARGGRILAGYWGQGTLVTVSS | 40 |
| 11-VH | QVQLQESGPGLVKPSEILSLTCTVSGGSLDGYYWSWIRQPPG KGLEWIGRIYDGSGTNYNPSLKSRVTISVDTSKNQFSLRLRS VTAADTAVYYCARGGRIFGGYWGQGTLVTVSS | 56 |
| 16-VH | QVQLQESGPGLVKPSETLSLTCTVSGGSLDNYYWSWIRQPPG KGLEWIGYIYYSGNTNYNPSLKSRVTISVDTSKNQFSLRLRS VTAADTAVYYCARGGRIFSGYWGQGTLVTVSS | 41 |
| 18-VH | QVQLQESGPGLVKPSETLSLTCTVSGGSLDNYYWSWIRQPPG KGLEWIGYIYYSGNTNYNPSLKSRVTISVDTSKNQFSLRLRS VTAADTAVYYCARGRGIFGYWGQGTLVTVSS | 42 |
| 24-VH | QVQLQESGPGLVKPSETLSLTCTVSGGSLDNYYWSWIRQPPG KGLEWIGRIYGDSATNYNPSLKSRVTISVDTSKNQFSLRLRSV TAADTAVYYCARGGRIFSGYWGQGTLVTVSS | 43 |

TABLE 3-continued

Antibody variable region sequences

| Name | Sequence | SEQ ID NO |
|---|---|---|
| 25-VH | QVQLQESGPGLVKPSETLSLTCTVSGGSLDNYYWSWIRQPPG KGLEWIGYIYYSGNTNYNPSLKSRVTISVDTSKNQFSLRLRS VTAADTAVYYCARGGRIFGHWGQGTLVTVSS | 44 |
| 17-VL\3-3-VL\3-6-VL\3-VL\6-VL\10-VL\11-VL\16-VL\18-VL\24-VL\25-VL | DIQMTQSPSSVSASVGDRVTISCRANQAIGTWLAWYQQKPG KAPKLLIYAASTLQSGVPSRFSGSGSGTEFTLTISSLQAEDVAV YYCQQYYTTPLTFGGGTKLEIK | 12 |
| L1-VL | EIVLTQSPSTLSASVGDRVTIPCRASLSIGSFLNWYQQRPGEA PKLLIFAASSLRSGVPSRFSGSGSGTDFTLTISGLQPEDFATYY CQQTYTTPYTFGQGTKVEIK | 45 |
| L2-VL | DIVMTQSPSSLSASVGDRVTIPCRASLSIGSFLNWYQQRPGEA PKLLIFAASSLRSGVPSRFSGSGSGTDFTLTISGLQPEDFATYY CQQTYTTPYTFGPGTRLDIK | 46 |
| L5-VL | EIVLTQSPSSLSASVGDRVTIPCRASLSIGSFLNWYQQRPGEA PKLLIFAASSLRSGVPSRFSGSGSGTDFTLTISGLQPEDFATYY CQQTYTTPYTFGPGTRLEIK | 47 |
| L12-1-1-VL\L12-6-1-VL | EIVLTQPPSSLSASVGDRVTIPCRASLSIGSFLNWYQQRPGEA PKLLIFAASSLRSGVPSRFSGSGSGTDFTLTISGLQPEDFATYY CQQTYTTPYTFGQGTKVDIK | 13 |
| L12-VL\L12-6-VL | EIVLTQSPSSLSASVGDRVTIPCRASLSIGSFLNWYQQRPGEA PKLLIFAASSLRSGVPSRFSGSGSGTDFTLTISGLQPEDFATYY CQQTYTTPYTFGQGTKVDIK | 65 |
| L24-VL | DIQMTQSPSSLSASVGDRVTIPCRASLSIGSFLNWYQQRPGEA PKLLIFAASSLRSGVPSRFSGSGSGTDFTLTISSLQPEDFATYY CQQTYTIPYTFGQGTKVEIK | 48 |
| L26-VL | EIVLTQSPSSLSASVGDRVTIPCRASLSIGSFLNWYQQRPGEA PKLLIFAASSLRSGVPSRFSGSGSGTDFTLTISSLQPEDFATYY CQQTYTTPYTFGQGTKLEIK | 49 |
| L12-1-VH\L12-2-VH\L12-3-VH\L12-6-1-VH\L12-6-VH\L12-8-VH\L12-9-VH | QVQLQESGPGLVKPSETLSLTCTVSGGSLDNYYWSWIRQPPG KGLEWIGYIYYSONTNYNPSLKSRVTISVDTSKNQFSLKLSS VTAADTAVYYCARGGRFLERYWGQGTLVTVSS | 50 |
| L12-2-VL\L12-10-VL | EIVLTQSPSSLSASVGDRVTIPCRASLSIGSFLNWYQQRPGEA PKLLIFAASSLRSGVPSRFSGSGSGTDFTLTISSLQPEDFATYY CQQTYTTPYTFGQGTKVEIK | 51 |
| L12-4-VL\L12-8-VL | EIVLTQSPSSLSASVGDRVTIPCRASLSIGSFLNWYQQKPGKA PKLLIFAASSLRSGVPSRFSGSGSGTDFTLTISSLQPEDFATYY CQQTYTTPYTFGQGTKVEIK | 52 |
| L12-3-VL\L12-7-VL | EIVLTQSPSSLSASVGDRVTITCRASLSIGSFLNWYQQKPGKA PKLLIFAASSLRSGVPSRFSGSGSGTDFTLTISSLQPEDFATYY CQQTYTTPYTFGQGTKVEIK | 53 |
| L12-1-VL\L12-5-VL | EIVLTQSPSSLSASVGDRVTITCRASLSIGSFLNWYQQKPGKA PKLLIYAASSLRSGVPSRFSGSGSGTDFTLTISSLQPEDFATYY CQQTYTTPYTFGQGTKVEIK | 54 |
| L12-9-VL\L12-11-VL | DIQMTQSPSSLSASVGDRVTITCRASLSIGSFLNWYQQKPGK APKLLIYAASSLRSGVPSRFSGSGSGTDFTLTISSLQPEDFATY YCQQTYTTPYTFGQGTKVEIK | 55 |

TABLE 4

Antibody VH CDRs

| Name | VH CDR1 | SEQ ID NO: | VH CDR2 | SEQ ID NO: | VH CDR3 | SEQ ID NO: |
|---|---|---|---|---|---|---|
| 17-VH | DNYYWS | 14 | YIYYSGNTNYNPSLKS | 17 | GGRFLERY | 23 |
| 3-3-VH | DNYYWS | 14 | YIYYSGNTNYNPSLKS | 17 | GGRIFGGY | 24 |
| 3-6-VH | DNYYWS | 14 | YIYYSGNTNYNPSLKS | 17 | GGRIFAGY | 25 |
| 3-VH | DGYYWS | 15 | RIYGNSTTNYNPSLKS | 18 | GGRIFAGY | 25 |

TABLE 4-continued

Antibody VH CDRs

| Name | VH CDR1 | SEQ ID NO: | VH CDR2 | SEQ ID NO: | VH CDR3 | SEQ ID NO: |
|---|---|---|---|---|---|---|
| 6-VH | NDYYWS | 16 | RIYGNGDTNYNPSLKS | 19 | GGRILAGY | 26 |
| 10-VH | DNYYWS | 14 | RIYYNGNTNYNPSLKS | 20 | GGRILAGY | 26 |
| 11-VH | DGYYWS | 15 | RIYDGSGTNYNPSLKS | 22 | GGRIFGGY | 24 |
| 16-VH | DNYYWS | 14 | YIYYSGNTNYNPSLKS | 17 | GGRIFSGY | 27 |
| 18-VH | DNYYWS | 14 | YIYYSGNTNYNPSLKS | 17 | GRGIF GY | 28 |
| 24-VH | DNYYWS | 14 | RIYGDSATNYNPSLKS | 21 | GGRIFSGY | 27 |
| 25-VH | DNYYWS | 14 | YIYYSGNTNYNPSLKS | 17 | GGRIFGH | 29 |
| L1-VH | DNYYWS | 14 | YIYYSGNTNYNPSLKS | 17 | GGRFLERY | 23 |
| L2-VH | DNYYWS | 14 | YIYYSGNTNYNPSLKS | 17 | GGRFLERY | 23 |
| L5-VH | DNYYWS | 14 | YIYYSGNTNYNPSLKS | 17 | GGRFLERY | 23 |
| L12-1-1-VH | DNYYWS | 14 | YIYYSGNTNYNPSLKS | 17 | GGRFLERY | 23 |
| L12-VH | DNYYWS | 14 | YIYYSGNTNYNPSLKS | 17 | GGRFLERY | 23 |
| L24-VH | DNYYWS | 14 | YIYYSGNTNYNPSLKS | 17 | GGRFLERY | 23 |
| L26-VH | DNYYWS | 14 | YIYYSGNTNYNPSLKS | 17 | GGRFLERY | 23 |
| L12X-VH | DNYYWS | 14 | YIYYSGNTNYNPSLKS | 17 | GGRFLERY | 23 |

Note:
L12X-VH represents L12-1-VH, L12-2-VH, L12-3-VH, L12-4-VH, L12-5-VH, L12-6-1-VH, L12-6-VH, L12-7-VH, L12-8-VH, L12-9-VH, L12-10-VH or L12-11-VH.

TABLE 5

Antibody VL CDRs

| Name | VL CDR1 | SEQ ID NO: | VL CDR2 | SEQ ID NO: | VL CDR3 | SEQ ID NO: |
|---|---|---|---|---|---|---|
| 17-VL | RANQAIGTWLA | 31 | AASTLQS | 33 | QQYYTTPLT | 35 |
| X-VL | RANQAIGTWLA | 31 | AASTLQS | 33 | QQYYTTPLT | 35 |
| L1-VL | RASLSIGSFLN | 30 | AASSLRS | 32 | QQTYTTPYT | 34 |
| L2-VL | RASLSIGSFLN | 30 | AASSLRS | 32 | QQTYTTPYT | 34 |
| L5-VL | RASLSIGSFLN | 30 | AASSLRS | 32 | QQTYTTPYT | 34 |
| L12-1-1-VL | RASLSIGSFLN | 30 | AASSLRS | 32 | QQTYTTPYT | 34 |
| L12-VL | RASLSIGSFLN | 30 | AASSLRS | 32 | QQTYTTPYT | 34 |
| L24-VL | RASLSIGSFLN | 30 | AASSLRS | 32 | QQTYTTPYT | 34 |
| L26-VL | RASLSIGSFLN | 30 | AASSLRS | 32 | QQTYTTPYT | 34 |
| L12X-VL | RASLSIGSFLN | 30 | AASSLRS | 32 | QQTYTTPYT | 34 |

Note:
X-VL represents 3-3-VL, 3-6-VL, 3-VL, 6-VL, 10-VL, 11-VL, 16-VL, 18-VL, 24-VL or 25-VL; L12X-VL represents L12-1-VL, L12-2-VL, L12-3-VL, L12-4-VL, L12-5-VL, L12-6-1-VL, L12-6-VL, L12-7-VL, L12-8-VL, L12-9-VL, L12-10-VL or L12-11-VL.

In terms of clearing target cells, the primary Fc-dependent functions of an antibody (e.g., the CD47 antibody) are complement-dependent cytotoxicity (CDC) initiated by the binding of C1q to the Fc region; antibody-dependent cellular cytotoxicity (ADCC) mediated by the interaction between the Fc region and Fcγ receptors (FcγRs), primarily FcγRIIIa, on immune effector cells (e.g., NK cells and neutrophils); and antibody-dependent cellular phagocytosis (ADCP) by macrophages through the recognition of opsinized target cells via FcγRI. Antibody subclasses differ in their abilities to mediate Fc-dependent effector activities. In humans, the IgG1 and IgG3 subclasses have high potency for CDC due to binding C1q. In addition, the IgG1 subclass has the highest affinity for FcγRs and is therefore the most effective in terms of ADCC and Fc-dependent ADCP. The IgG4 subclass does not have the ability to bind to C1q and has greatly reduced FcγR binding affinity and therefore has significantly diminished effector function.

Antibody 6Y-G4 of the IgG4P subclass having mutation S228P for stabilizing the hinge region of the antibody was prepared according to Antibody 6Y-G1 (the CH of 6Y-G1 set forth in SEQ ID NO: 3 was replaced with the CH set forth in SEQ ID NO: 4, and the other sequences were unchanged), further diminishing the antibody Fc effect.

17-ScFv was prepared as an example. The method of preparing a ScFV in the present invention is described below.

A nucleotide sequence encoding 17-ScFv (set forth in SEQ ID NO: 59) was linked to the pcDNA3.1(+) plasmid vector using restriction endonuclease Hind III/EcoRI. The plasmid vector was then transiently transfected into HEK293F cells, and the HEK293F cells were allowed to express the antibody of the above amino acid sequence. Antibody 17-ScFv was obtained after purification by immobilized metal affinity chromatography (IMAC) using a protein A column, and sequencing showed that its sequence was in agreement with the expected one.

Other ScFvs were similarly prepared and purified, and sequencing showed that their sequences were in agreement with the expected ones.

The sequence of SEQ ID NO: 59 is shown below:

```
caggtgcagctgcaggagtcgggcccaggactggtgaagccttcggagac
cctgtccctcacctgcactgtctctggtggctccctcgataattactact
ggagctggatccggcagcccccagggaagggactggagtggattggatat
atctattacagtgggaacaccaactacaacccctccctcaagagtcgagt
caccatatcagtagacacgtccaagaaccagttctcgttgaggctgaggt
ctgtgaccgctgcggacacggccgtgtattactgtgcgagaggagggcga
tttttggaacgttactggggccagggaaccctggtcaccgtctcctcagg
tggaggcggttcaggcggaggtggctctggcggtggcggatcggacatcc
agatgacccagtctccatcttccgtgtctgcatctgtaggagacagagtc
accatctcttgtcgggcgaatcaggctattggcacttggttagcctggta
tcagcaaaagccaggaaaagcccctaagctcctgatctatgcggcatcca
ctttgcaaagtggggtcccatcaaggttcagcggcagtggatctgggaca
gaattcactctcaccatcagcagcctgcaggctgaagatgtggcagttta
ttactgtcagcaatattatactactcccctcactttcggcggagggacca
agctggagatcaaa
```

Example 3: Biological Activity of Anti-CD47 Antibodies

1. Determination of Binding Activity of 17-ScFv by FACS

Figure 1A:
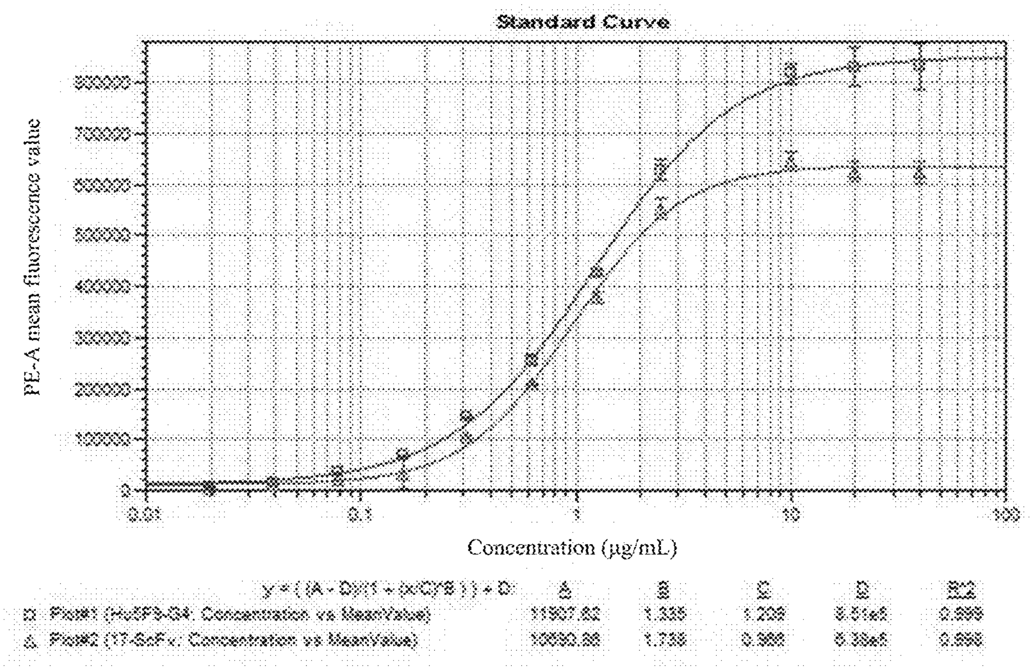
FIG. 1 is a set of graphs depicting the ability of Antibody 17-ScFv to bind to CD47 on the surfaces of CHO-CD47 cells (FIG. 1A) and Jurkat cells (FIG. 1B).
Figure 1B:
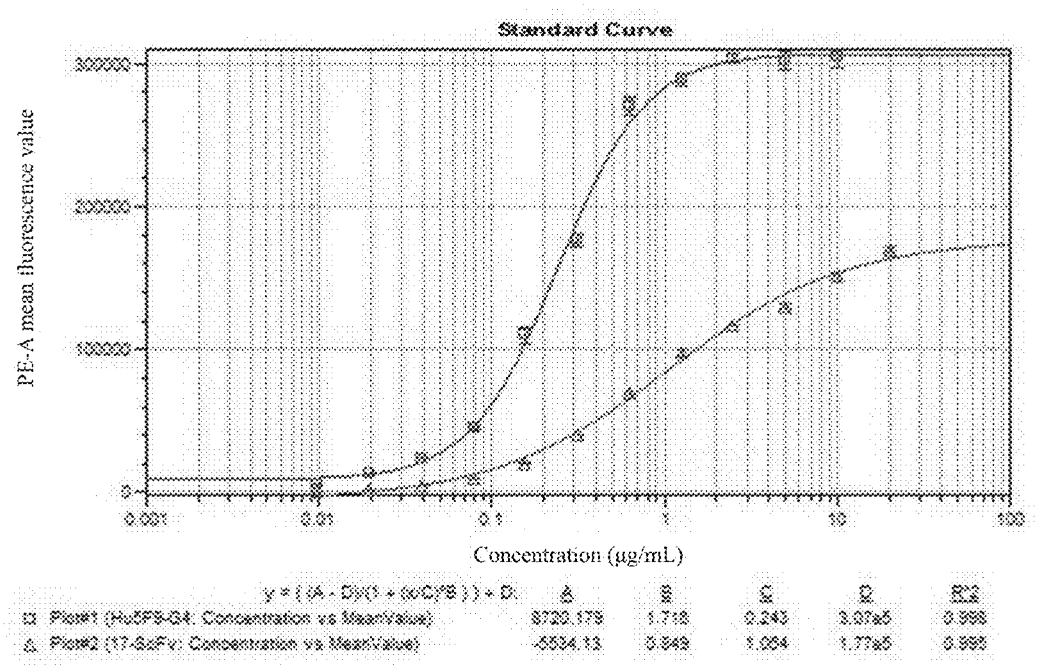

The binding activity of 17-ScFv to CHO-CD47 or Jurkat cell surface CD47 was tested (FIGS. 1A-1B). The binding activity assay was carried out as follows:

Antibodies 17-ScFv and Hu5F9-G4 (the heavy chain of Hu5F9-G4 is composed of a variable region set forth in SEQ ID NO: 8 and a constant region set forth in SEQ ID NO: 4, and the light chain is composed of a variable region set forth in SEQ ID NO: 9 and a constant region set forth in SEQ ID NO: 5) were diluted with PBS to various concentrations (20, 10, 5, 2.5, 1.25, 0.625, 0.313, 0.156, 0.078, 0.039, 0.02 and 0.01 μg/mL) and incubated with CHO-CD47 or Jurkat cell surface CD47 at 4° C. for 30 min, and the cells were washed once with PBS. Goat anti-human IgG Fc-PE (eBioscience, catalog No. 2183639) fluorescent secondary antibody was added, and the cells were incubated at 4° C. for 15 min and washed twice with PBS. The PE-A mean fluorescence signal value was measured on a flow cytometer. FIGS. 1A-1B show that 17-ScFv was able to bind to cell surface CD47 in a dose-dependent fashion.

2. SIRP-α Blocking Activity

Figure 2:
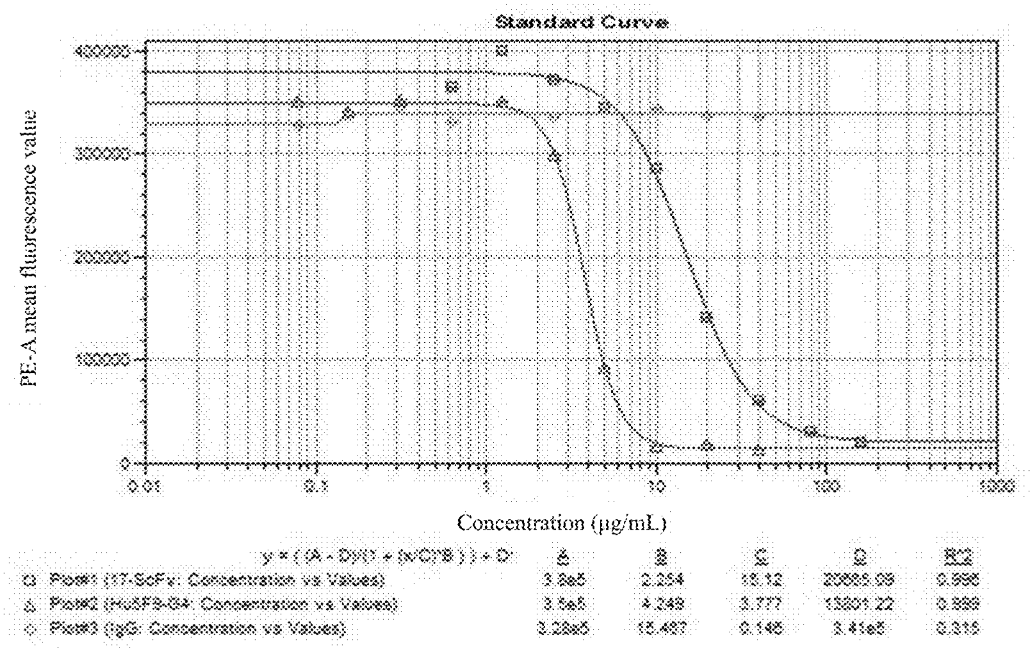
FIG. 2 shows the ability of Antibody 17-ScFv to compete with the ligand SIRPα for binding to CHO surface CD47, as determined by flow cytometry.
Figure 3A:
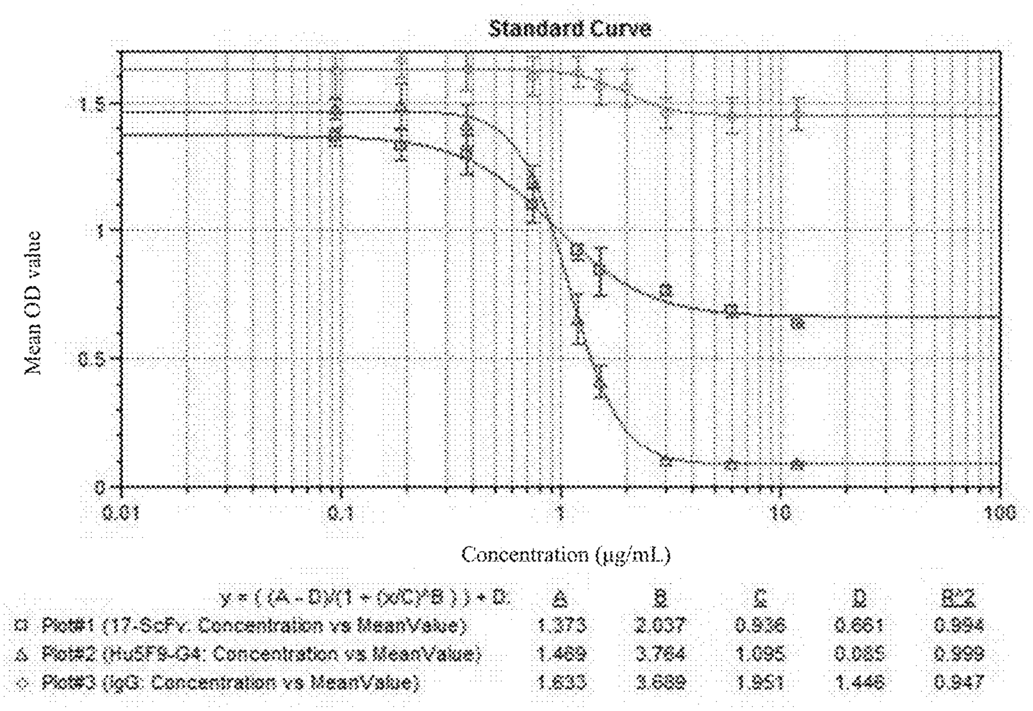
Figure 3D:
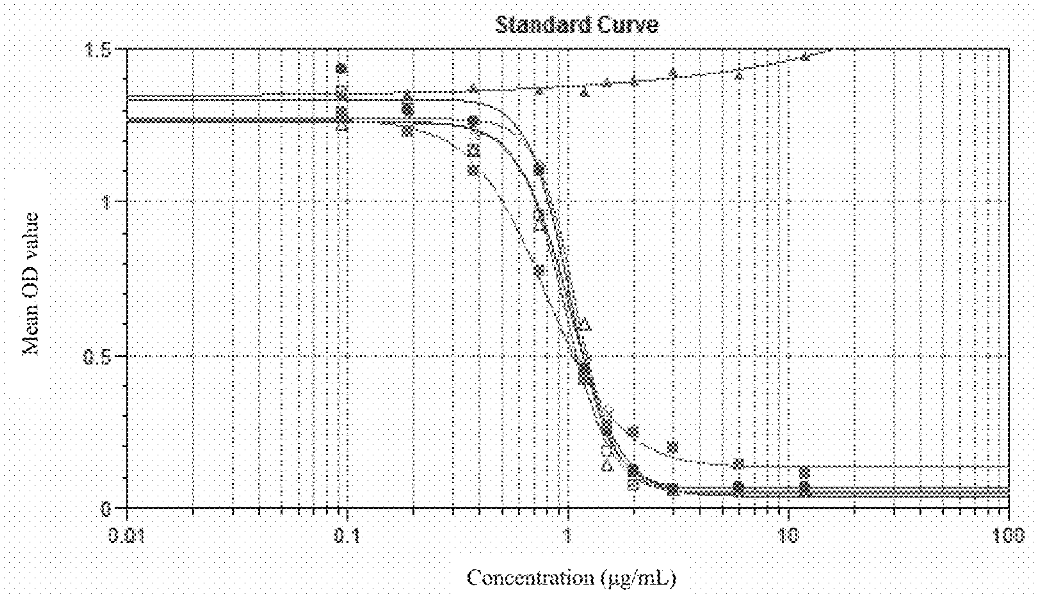
Figure 3E:
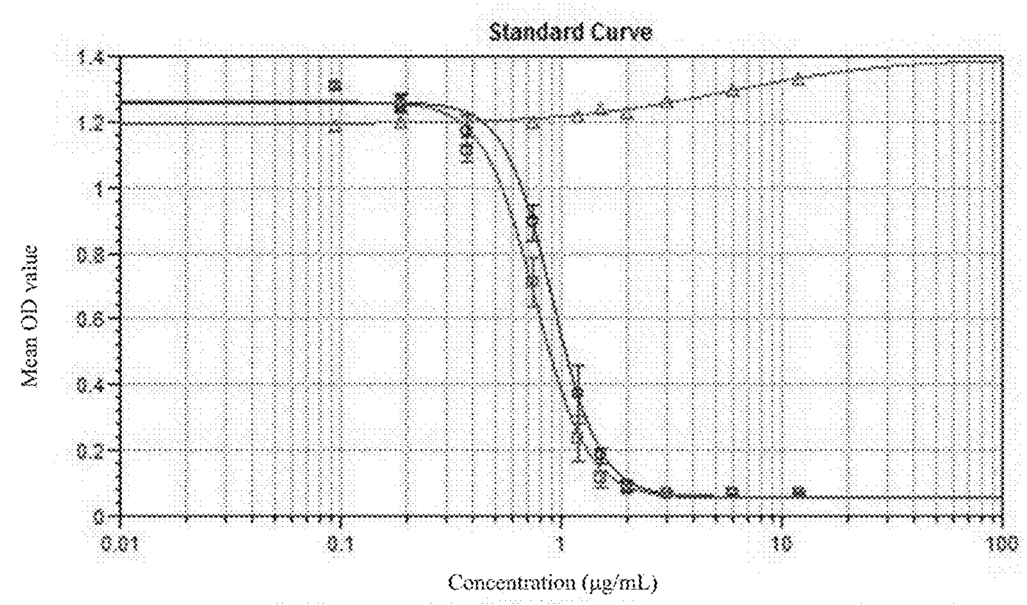
Figure 4A:
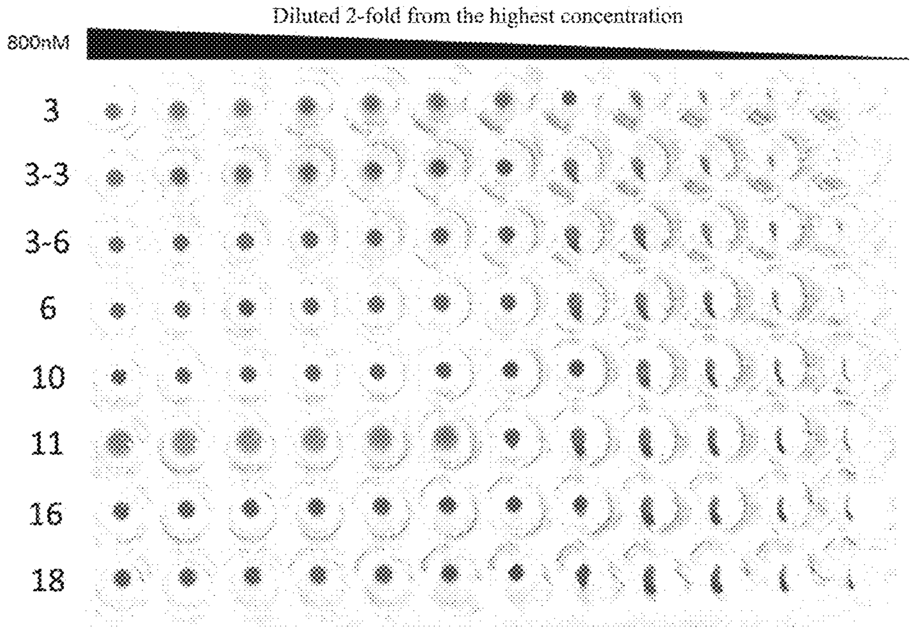
FIGS. 4A-4E show the hemagglutination of red blood cells (RBCs) caused by CD47 antibodies. Non-agglutinated RBCs appear as a flow of red blood cell masses in a line, slightly agglutinated RBCs appear as a dot, and significantly agglutinated RBCs appear as a fuzzy mass of cells in the well.
Figure 4B:
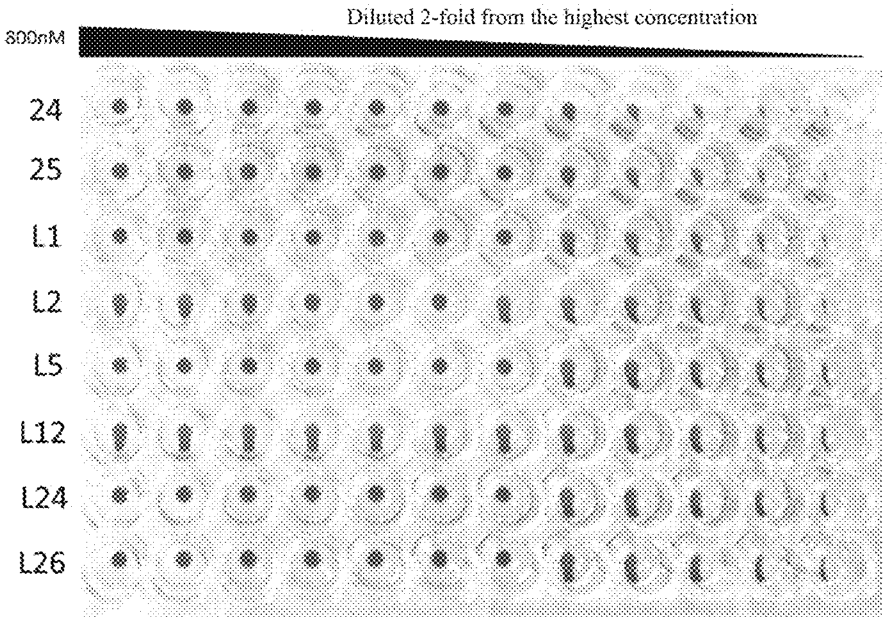
Figure 4C:
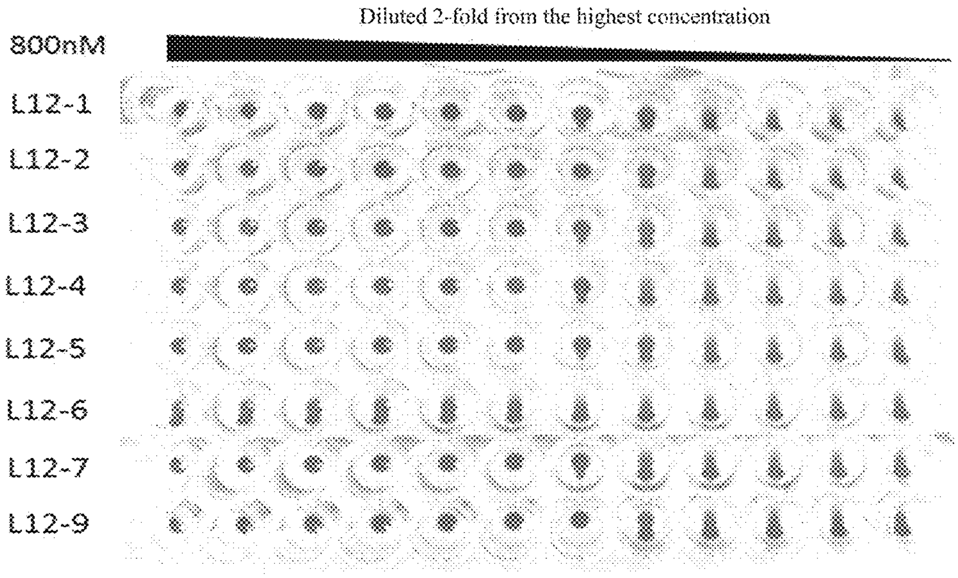
Figure 4D:
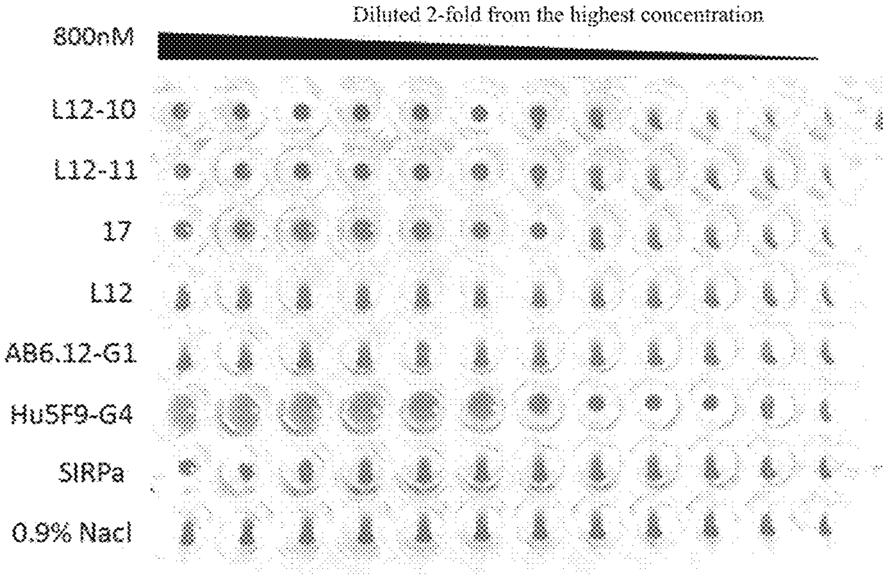
Figure 4E:
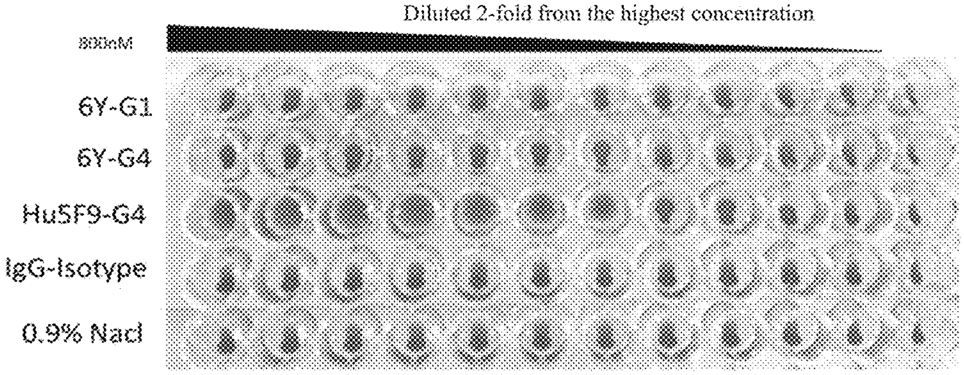

The ability of 17-ScFv to block the binding of SIRPa to CHO-CD47 cell surface CD47 was determined using the FACS technique. Antibody 17-ScFv was diluted with PBS to various concentrations (160, 80, 40, 20, 10, 5, 2.5, 1.25 and 0.625 μg/mL). Antibodies Hu5F9-G4 and IgG (diluted with PBS to various concentrations: 40, 20, 10, 5, 2.5, 1.25, 0.625, 0.313, 0.156 and 0.078 μg/mL) were incubated with CHO-CD47 cell surface CD47 at 4° C. for 30 min, and the cells were washed once with PBS. SIRPα-Fc-Bio (6.5 μg/mL) was added, and the cells were incubated at 4° C. for 15 min and washed once with PBS. Then Streptavidin PE (eBioscience, catalog No. 1992345) fluorescent secondary antibody was added, and the cells were incubated at 4° C. for 15 min and washed twice with PBS. The PE-A mean fluorescence signal value was measured on a flow cytometer. FIG. 2 shows that 17-ScFv was able to inhibit the binding of SIRPα to cell surface CD47 in a dose-dependent fashion.

Using ELISA competition method, 17-ScFv or 18 antibodies (Antibody 3, Antibody 3-3, Antibody 3-6, Antibody 6, Antibody 10, Antibody 11, Antibody 16, Antibody 18, Antibody 24, Antibody 25, Antibody L12, Antibody L1, Antibody L5, Antibody L24, Antibody L26, Antibody 17, Antibody 6Y-G1, and Antibody 6Y-G4), a positive control (Antibody Hu5F9-G4) and a negative control (antibody IgG) were diluted with PBS to various concentrations (12, 6, 3, 2, 1.5, 1.2, 0.75, 0.375, 0.188 and 0.094 μg/mL) and incubated with CD47-His (2 μg/mL) antigen coating on an ELISA plate at room temperature for 1 h, and the plate was washed four times with PBST. Then SIRPα-Fc-Bio (0.1 μg/mL) (prepared according to Thermo Scientific EZ-Link® NHS-Biotin Reagents kit) ligand was added and incubated with the CD47-His antigen at room temperature for 1 h, and the plate was washed four times with PBST. Chemiluminescence reactions of the bound SIRPα-Fc-Bio with HRP-conjugated streptavidin secondary antibody were carried out, and the OD450 values were measured using a plate reader. The $IC_{50}$ of the antibodies was calculated from the OD450 values, thereby determining the SIRPα blocking activity of the antibodies. FIGS. 3A-3E show that all the tested antibodies demonstrated dose-dependent inhibition of the binding of SIRPα to CD47 antigen.

3. Hemagglutination Assay

The CD47 antibodies were tested for hemagglutination. 5 mL of fresh blood from a healthy human donor was collected into a tube containing heparin sodium anticoagulant. The PBMCs (for other purposes) were isolated first using a lymphocyte-isolating solution, and then 1 mL of red blood cells at the bottom of the tube was collected into 6 mL of normal saline. The red blood cells were washed and centrifuged at 2000 rpm for 5 min; the wash procedure was repeated until the supernatant was not significantly red. Then the red blood cells were resuspended in normal saline to prepare a 2% red blood cell suspension. At room temperature, 50 μL of a CD47 antibody serially diluted 2-fold in PBS (the maximum concentration was 800 nM; 12 gradients in total) was mixed with 50 μL of the 2% red blood cell suspension, and the mixture was added to a 96-well U-plate and incubated for 4 h. Then the hemagglutination caused by the antibody was assessed by titling 45° the 96-well U-plate and observing the flow of masses of red blood cells; if the cells flow in a line, it means that no hemagglutination occurred. Most of the tested CD47 antibodies induced hemagglutination when at high concentrations (Antibody 17 caused significant hemagglutination) and did not cause hemagglutination when at about 6 nM. Antibody L12, Antibody 6Y-G1 (i.e., Antibody L12-6) and Antibody 6Y-G4 did not cause any hemagglutination (FIGS. 4A-4E). The positive control Antibody Hu5F9-G4 did cause hemagglutination, and AB6.12-G1 and the ligand SIRPα did not. The heavy chain of AB6.12-G1 is composed of a variable region set forth in SEQ ID NO: 6 and a constant region set forth in SEQ ID NO: 3, and the light chain is composed of a variable region set forth in SEQ ID NO: 7 and a constant region set forth in SEQ ID NO: 5. The heavy chain of Hu5F9-G4 is composed of a variable region set forth in SEQ ID NO: 8 and a constant region set forth in SEQ ID NO: 4, and the light chain is composed of a variable region set forth in SEQ ID NO: 9 and a constant region set forth in SEQ ID NO: 5. See Table 6.

TABLE 6

Sequence listing for positive antibodies

| Name | SEQ ID NO: | Sequence |
|---|---|---|
| AB6.12-G1 Heavy chain variable region | 6 | QMQLVOSGAEVKKTGSSVKVSCKASGFNIKDYYLHWVRQAPGQALEWMGWIDPDQGDTEYAQKFQDRVTITRDRSMSTAYMELSSLRSEDTAMYYCNAAYGSSSYPMDYWGQGTTVTVSS |
| AB6.12-G1 Light chain variable region | 7 | NIQMTQSPSAMSASVGDRVTITCKASQDIHRYLSWFQQKPGKVPKHLIYRANRLVSGVPSRFSGSGSGTEFTLTISSLQPEDFATYYCLQYDEFPYTFGGGTKVEIK |

TABLE 6-continued

| Sequence listing for positive antibodies | | |
|---|---|---|
| Name | SEQ ID NO: | Sequence |
| Hu5F9-G4 Heavy chain variable region | 8 | QVQLVQSGAEVKKPGASVKVSCKASGYTFTNYNMHWVRQAPGQRLEW MGTIYPGNDDTSYNQKFKDRVTITADTSASTAYMELSSLRSEDTAVYYCA RGGYRAMDYWGQGTLVTVSS |
| Hu5F9-G4 Light chain variable region | 9 | DIVMTQSPLSLPVTPGEPASISCRSSQSIVYSNGNTYLGWYLQKPGQSPQL LIYKVSNRFSGVPDRFSGSGSGTDFTLKISRVEAEDVGVYYCFQGSHVPY TFGQGTKLEIK |

Figure 5A:
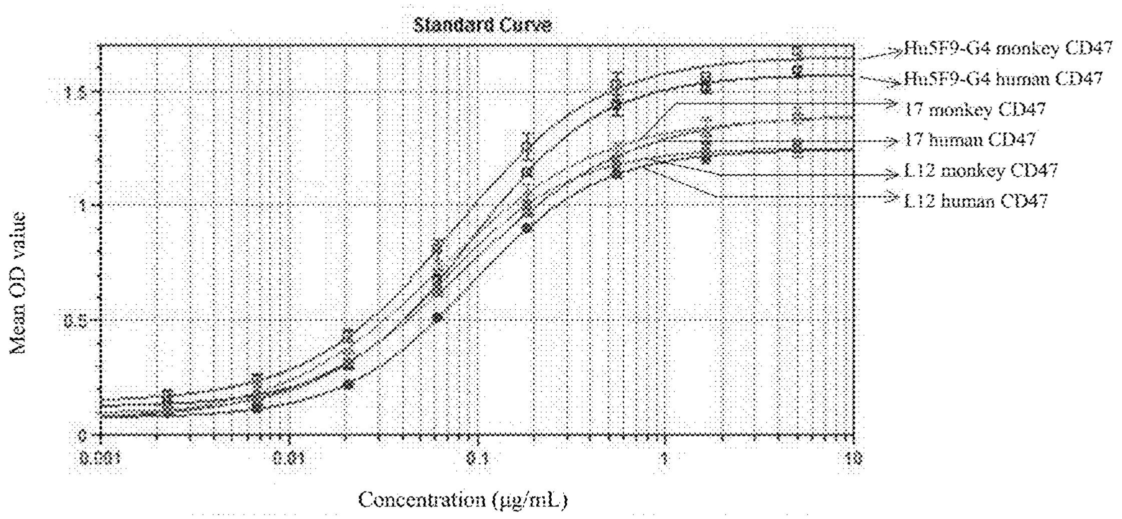
FIGS. 5A-5B show the binding of CD47 antibodies to human CD47 or macaque CD47, as assessed by ELISA.
Figure 5B:
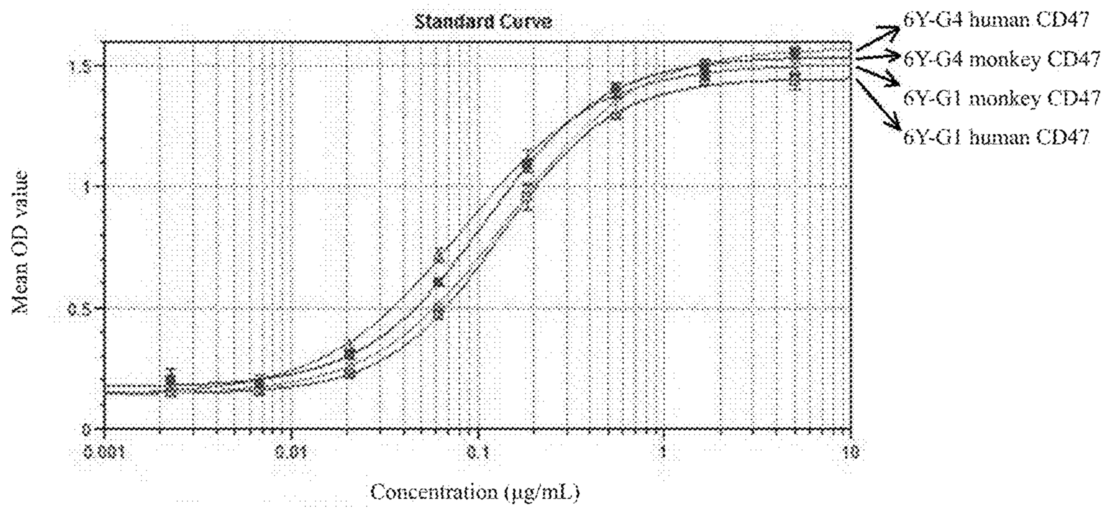

4. CD47 Binding Assay (ELISA):

The binding activity of the CD47 antibodies to human CD47 and macaque CD47 was determined by ELISA. Antibody 17, Antibody L12, Antibody 6Y-G1, Antibody 6Y-G4 and Antibody Hu5F9-G4 were diluted 3-fold with PBS from 5 μg/mL to 8 concentrations and then incubated with human or macaque CD47-Fc (2 μg/mL) antigen coating on an ELISA plate at room temperature for 1 h, and the plate was washed four times with PBST. Then HRP-anti-kappa (1:10000, sigma) secondary antibody was added and incubated with the antibodies at room temperature for 1 h, and the plate was washed four times with PBST. Chemiluminescence reactions of the bound HRP-anti-kappa with TMB substrate were carried out, and the OD450 values were measured using a plate reader. The $EC_{50}$ of the antibodies was calculated from the OD450 values, thereby determining the binding activity of the antibodies to human or macaque CD47. FIGS. 5A-5B show that all the tested antibodies demonstrated dose-dependent binding of the antibodies to CD47 antigen. The parameters are shown in Table 7.

TABLE 7

| Binding affinities of CD47 antibodies for human CD47 and macaque CD47 | | | | | | | | | | |
|---|---|---|---|---|---|---|---|---|---|---|
| Antibody | Hu5F9-G4 | | 17 | | L12 | | 6Y-G1 | | 6Y-G4 | |
| Type of CD47 | Human CD47 | Macaque CD47 | Human CD47 | Macaque CD47 | Human CD47 | Macaque CD47 | Human CD47 | Macaque CD47 | Human CD47 | Macaque CD47 |
| Affinity (μg/mL) | 0.092 | 0.075 | 0.088 | 0.064 | 0.094 | 0.066 | 0.132 | 0.083 | 0.142 | 0.11 |

5, CD47 Binding Assay (Fortebio)

The binding activity of 11 antibodies (Antibody L12-1, Antibody L12-2, Antibody L12-3, Antibody L12-4, Antibody L12-5, Antibody L12-6, Antibody L12-7, Antibody L12-9, Antibody L12-10, Antibody L12-11, and Antibody L12) and Hu5F9-G4 to human CD47 was determined by Fortebio.

A protein A sensor was pre-wetted in PBS for 10 min for later use. The test antibodies were diluted to 10 μg/mL with PBST having a pH of 6.8 and containing 0.5% BSA (hereinafter referred to as dilution buffer). The PA sensor was immobilized in the antibodies until the signal was about 1.7 nm. CD47-His antigen was diluted with the dilution buffer to 50, 25, 12.5 and 6.25 nM. The dilution buffer, the antigen dilutions at the gradient concentrations, a regeneration buffer (1 M $MgCl_2$ at pH 8.4) and a neutralization buffer (PBST) were sequentially added to the corresponding columns in a 96-well plate, and the following steps were performed: (1) Baseline: 60 seconds of baseline detection in the dilution buffer; (2) Association: 100 seconds of association in the serial dilutions of the antigen and a sample blanks (dilution buffer); (3) Dissociation: 700 seconds of dissociation in the dilution buffer; (4) Regeneration: 5 seconds of regeneration in the regeneration buffer; (5) Neutralization: 5 seconds of neutralization in the neutralization buffer; and (6) 3 Regeneration-Neutralization cycles.

The data was processed and analyzed using Data Analysis 8.2, and the sample data was fitted after reference (sample blank) signal subtraction to obtain an affinity constant (KD). The affinity results of the antibodies are summarized in Table 8. The results show that the 11 antibodies had similar binding affinities for CD47 antigen.

TABLE 8

| Antibody affinities | |
|---|---|
| Antibody number | KD (nM) |
| L12-1 | 0.152 |
| L12-2 | 0.122 |
| L12-3 | 0.144 |
| L12-4 | 0.107 |
| L12-5 | 0.138 |
| L12-6 | 0.142 |
| L12-7 | 0.149 |
| L12-9 | 0.124 |
| L12-10 | 0.195 |
| L12-11 | 0.175 |
| L12 | 0.112 |
| Hu5F9-G4 | 0.306 |

6. Phagocytosis

An in vitro phagocytosis assay was carried out to assess whether the CD47 antibodies promote phagocytosis of CD47-expressing target cells by macrophages. Briefly, in the presence of CD47 antibodies (0.7 nM), RAW264.7 macrophages ($2\times10^5$ cells/mL) (Cell Resource Center, Institute of Basic Medical Sciences, Chinese Academy of Medical Sciences, 3111C0001CCC000146) and CFSE-labeled Raji cells ($4\times10^5$ cells/mL) (Promega, JA1595) were plated to a 24-well plate in a ratio of 1:2 and incubated in the dark at 37° C. for 2 h. Upon completion of incubation, the cells were washed twice with PBS and the RAW264.7 cells were trypsinized. The digested macrophages were transferred to 1.5 mL EP tubes and centrifuged at 2000 rpm for 5 min. The supernatant was removed and 100 μL of APC-F4/80 fluorescent antibody (eBiosciences) was added to each tube. The cells were incubated in the dark at 4° C. for 30 min, centrifuged at 2000 rpm for 5 min and washed twice with PBS buffer. The cells were obtained on a BD C6 flow cytometer. The phagocytosis index was analyzed. The phagocytosis index was calculated as: phagocytosis index=number of CFSE positive macrophages (i.e. number of macrophages that phagocytosed tumor cells)/per 5000 macrophages. Antibodies 6Y-G1, 6Y-G4, 17, L12 and Hu5F9-G4 showed potent phagocytosis-enhancing abilities (FIGS. 6A-6B). FIG. 6B shows that 6Y-G4 elicited a slightly weaker phagocytic response than 6Y-G1, which indicates that the Fc effect of the IgG4 antibody was weaker.

Example 4: Effects of CD47 Antibodies on Blood Cells

Prior to the present invention, known CD47-binding molecules that block SIRPα and contain a Fc domain (e.g., CD47 antibodies and recombinant SIRPα-Fc fusion proteins) all induce red blood cell and platelet reduction to varying degrees. Therefore, the effects of the antibodies disclosed herein on blood cells were assessed in cynomolgus monkeys. A total of 8 normal cynomolgus monkeys that met the experimental requirements were selected. Half of the monkeys were female. The males weighed from 3.70 to 5.30 kg, and the females weighed from 2.75 to 3.55 kg. The monkeys were simple randomly divided into 4 groups, with 2 animals in each group (a male and a female) according to body weight. The negative control group was given normal saline. The test samples were Antibody 6Y-G1 (i.e., Antibody L12-6) and Hu5F9-G4 and AB6.12-G1. The vehicle for intravenous infusion was normal saline. The drugs were administered 5 times by intravenous infusion once a week at doses of 1→10→10→30→30 mg/kg in a volume of 10 mL/kg. After the administrations were completed, the animals were observed until day 42. FIGS. 7A-7D show that all the three antibodies resulted in hemoglobin and red blood cell reduction, and the hemoglobin and red blood cell levels decreased to a low point in two weeks and gradually returned to normal; the platelet content fluctuated before and after administration of all the three antibodies and returned to normal after administration was stopped; the reticulocyte count showed a growing tendency following administration, and 6Y-G1 caused a greater increase in the reticulocyte count following administration than the other two antibodies.

Example 5: In Vivo Antitumor Activity of Fc Variants of CD47 Antibodies

Figure 8:
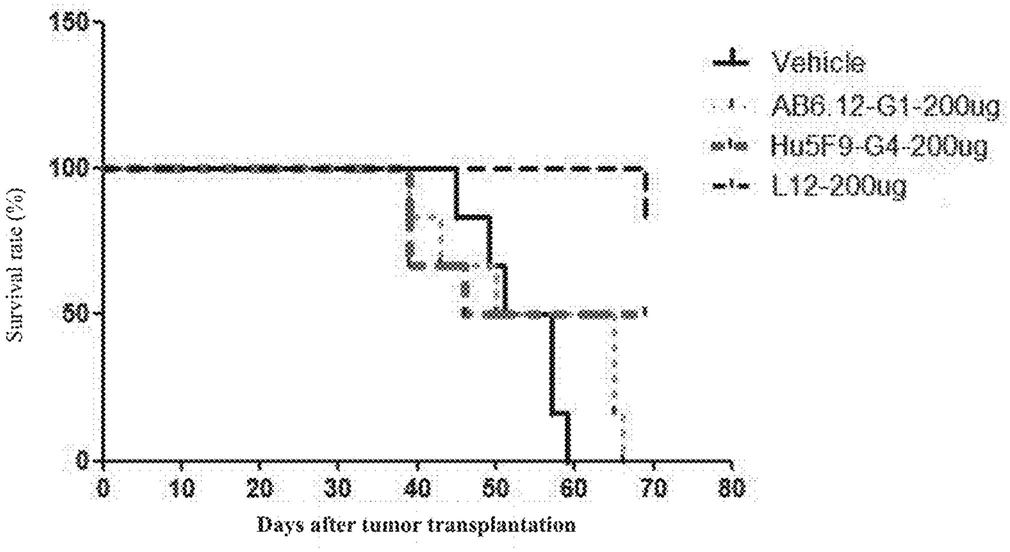
FIG. 8 shows the antitumor effect of Antibody L12 in a tumor model of the human blood tumor MV4-11 system, with antibodies AB6.12-G1 and Hu5F9-G4 as positive controls. The mice were all treated at an antibody dose of 200 μg, three times a week.

The antitumor effect of the test drug Antibody L12 in a tumor model of the human blood tumor MV4-11 system was evaluated. NOD.SCID mice (GemPharmatech Co., Ltd., weighing 18-22 g, at 6-8 weeks of age) were inoculated with MV4-11 cells (ATCC) via tail vein, and a tumor model of the human blood tumor MV4-11 system was created about 4 weeks after the inoculation. The mice were divided into groups of 6: test AB6.12-G1 0.2 mg/mouse; Hu5F9-G4 0.2 mg/mouse; Antibody L12 0.2 mg/mouse; and vehicle (normal saline) control group. The mice were intraperitoneally injected with the drugs three times a week over three weeks. The therapeutic effects were evaluated according to increase in life span (ILS). The safety was evaluated according to change in animal body weight and mortality during administration. FIG. 8 shows that the test drugs AB6.12-G1 (0.2 mg/mouse) and Hu5F9-G4 (0.2 mg/mouse) caused an increase of 7.4% and an increase of 6.5% in life span relative to the vehicle control group, which are not statistically significant differences ($p=1.000$)—they failed to produce significant antitumor effects. Antibody L12 (0.2 mg/mouse) led to a median survival of 69 days, achieving an increase of 27.8% in median survival relative to the control group, which is a statistically significant difference ($p=0.007$).

The antitumor activity of Antibody 6Y-G4 was evaluated in a Raji model of lymphoma. Raji cells were implanted subcutaneously in NOD/SCID mice, which were randomized into 3 groups (8 mice per group, day 0). Group 1: vehicle control (normal saline); Group 2: Hu5F9-G4 (positive control); Group 3: 6Y-G4. Treatment with each antibody or vehicle (buffer only) began when tumors were palpable (50 $mm^3$, day 4). The mice were sacrificed when their tumor volumes reached about 3000 mm3. Tumor volumes were measured every 3 days. Antibodies were administered intraperitoneally (IP) at 100 μg/dose 3 times a week over 3 weeks (a total of 9 doses per mouse). Treatment began on day 4 and ended on day 21. As shown in FIG. 9, the test drug 6Y-G4 and Hu5F9-G4 treatment groups demonstrated extremely significant antitumor effects at the administration concentration of 0.1 mg/mouse: tumor growth was significantly inhibited upon administration, and on day 17 of administration (PG-D17) most mice became tumor-free; the 6Y-G4 (0.1 mg/mouse) and Hu5F9-G4 (0.1 mg/mouse) treatment groups had mean tumor volumes of 4 $mm^3$ (7 of the 8 mice became tumor-free) and 7 $mm^3$ (5 of the 8 mice became tumor-free), respectively; the relative tumor growth inhibition (TGI) rates were 99.87% and 99.76%, which were statistically significant differences (both p values $<0.001$) relative to the vehicle control group.

The invention claimed is:

1. An antibody or an antigen-binding fragment, wherein the antibody or the antigen-binding fragment specifically binds to CD47 and comprises:

a VH CDR1 set forth in SEQ ID NO: 14, a VH CDR2 set forth in SEQ ID NO: 17, a VH CDR3 set forth in any one of SEQ ID NOs: 23, 24, 25, 27, 28, and 29, a VL CDR1 set forth in SEQ ID NO: 31, a VL CDR2 set forth in SEQ ID NO: 33, and a VL CDR3 set forth in SEQ ID NO: 35; or a VH CDR1 set forth in SEQ ID NO: 15, a VH CDR2 set forth in SEQ ID NO: 18, a VH CDR3 set forth SEQ ID NO: 25, a VL CDR1 set forth in SEQ ID NO: 31, a VL CDR2 set forth in SEQ ID NO: 33, and a VL CDR3 set forth in SEQ ID NO: 35; or a VH CDR1 set forth in SEQ ID NO: 16, a VH CDR2 set forth in SEQ ID NO: 19, a VH CDR3 set forth SEQ ID NO: 26, a VL CDR1 set forth in SEQ ID NO: 31, a VL CDR2 set forth in SEQ ID NO: 33, and a VL CDR3 set forth in SEQ ID NO: 35; or a VH CDR1 set forth in SEQ ID NO: 14, a VH CDR2 set forth in SEQ ID NO: 17, a VH CDR3 set forth in SEQ ID NO: 23, a VL CDR1 set forth in SEQ ID NO: 30, a VL CDR2 set forth in SEQ ID NO: 32, and a VL CDR3 set forth in SEQ ID NO: 34.

2. The antibody or the antigen-binding fragment according to claim 1, wherein the antibody or the antigen-binding fragment comprises a heavy chain variable region VH comprising the amino acid sequence selected from any one of SEQ ID NOs: 11, 36-39, 41-42, 44, and 50, or an amino acid sequence having at least 90% sequence identity to the amino acid sequence of any one of SEQ ID NOs: 11, 36-39, 41-42, 44, and 50.

3. The antibody or the antigen-binding fragment according to claim 1, wherein the antibody or the antigen-binding fragment comprises a light chain variable region VL comprising the amino acid sequence selected from any one of SEQ ID NOs: 12-13, 45-49, 51-55 and 65, or an amino acid sequence having at least 90% sequence identity to the amino acid sequence of any one of SEQ ID NOs: 12-13, 45-49, 51-55 and 65.

4. The antibody or the antigen-binding fragment according to claim 1, wherein the antibody or the antigen-binding fragment comprises a heavy chain variable region VH comprising one or more amino acid residue mutations according to Kabat numbering selected from the following group:

(a) R81K, and (b) R82aS.

5. The antibody or the antigen-binding fragment according to claim 1, wherein the antibody or the antigen-binding fragment comprises a heavy chain variable region VH comprising the amino acid sequence selected from amino acid sequences set forth in SEQ ID NOs: 11 and 50, or an amino acid sequence having at least 90% sequence identity to the amino acid sequence set forth in SEQ ID NO: 11 or 50.

6. The antibody or the antigen-binding fragment according to claim 1, wherein the antibody or the antigen-binding fragment comprises a light chain variable region VL comprising the amino acid sequence selected from any one of SEQ ID NOs: 13, 45-49, 51-55 and 65, or an amino acid sequence having at least 90% sequence identity to the amino acid sequence of any one of SEQ ID NOs: 13, 45-49, 51-55 and 65.

7. An antibody or an antigen-binding fragment, wherein the antibody or the antigen-binding fragment specifically binds to CD47 and comprises a heavy chain variable region VH and a light chain variable region VL; the VH comprises the amino acid sequence selected from SEQ ID NOs: 11 and 50, and the VL comprises the amino acid sequence selected from SEQ ID NOs: 13 and 65.

8. The antibody or the antigen-binding fragment according to claim 1, wherein the antibody comprises a heavy chain H and a light chain L; the heavy chain H comprises the amino acid sequence selected from any one of SEQ ID NOs: 60 and 62-63, and the light chain L comprises the amino acid sequence selected from amino acid sequences set forth in SEQ ID NOs: 61 and 64.

9. The antibody or the antigen-binding fragment according to claim 1, wherein the antibody or the antigen-binding fragment is of an IgG isotype selected from IgG1 subtype, IgG2 subtype, IgG3 subtype and IgG4 subtype.

10. The antibody or the antigen-binding fragment according to claim 9, wherein the antibody or the antigen-binding fragment is IgG4P.

11. A composition, wherein the composition comprises the antibody or the antigen-binding fragment according to claim 1 and a pharmaceutically acceptable carrier.

12. A biomaterial, being (i) a polynucleotide, wherein the polynucleotide encodes the antibody or the antigen-binding fragment according to claim 2; or (ii) an expression vector, wherein the expression vector comprises a polynucleotide encoding the antibody or the antigen-binding fragment according to claim 2; or (iii) a cell, wherein the cell comprises one or more polynucleotides encoding the antibody or the antigen-binding fragment according to claim 1.

13. A method for treating cancer or infection, wherein the method comprises administering to a subject an effective amount of the antibody or the antigen-binding fragment according to claim 1.

* * * * *

SEQUENCE LISTING

```
<160> NUMBER OF SEQ ID NOS: 65

<210> SEQ ID NO 1
<211> LENGTH: 139
<212> TYPE: PRT
<213> ORGANISM: Homo sapiens

<400> SEQUENCE: 1

Met Trp Pro Leu Val Ala Ala Leu Leu Leu Gly Ser Ala Cys Cys Gly
```

```
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro
    130                 135


<210> SEQ ID NO 2
<211> LENGTH: 6
<212> TYPE: PRT
<213> ORGANISM: Artificial Sequence
<220> FEATURE:
<223> OTHER INFORMATION: HIS tag

<400> SEQUENCE: 2

His His His His His His
1               5


<210> SEQ ID NO 3
<211> LENGTH: 330
<212> TYPE: PRT
<213> ORGANISM: Artificial Sequence
<220> FEATURE:
<223> OTHER INFORMATION: IgG1 heavy chain constant region sequence

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

-continued

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 4
<211> LENGTH: 327
<212> TYPE: PRT
<213> ORGANISM: Artificial Sequence
<220> FEATURE:
<223> OTHER INFORMATION: IgG4 heavy chain constant region sequence

<400> SEQUENCE: 4

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 5
<211> LENGTH: 107
<212> TYPE: PRT
<213> ORGANISM: Artificial Sequence
<220> FEATURE:
<223> OTHER INFORMATION: Light chain constant region sequence

<400> SEQUENCE: 5

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 6
<211> LENGTH: 120
<212> TYPE: PRT
<213> ORGANISM: Artificial Sequence
<220> FEATURE:
<223> OTHER INFORMATION: AB6.12-G1 Heavy chain variable region

<400> SEQUENCE: 6

Gln Met Gln Leu Val Gln Ser Gly Ala Glu Val Lys Lys Thr Gly Ser
1 5 10 15

Ser Val Lys Val Ser Cys Lys Ala Ser Gly Phe Asn Ile Lys Asp Tyr
20 25 30

Tyr Leu His Trp Val Arg Gln Ala Pro Gly Gln Ala Leu Glu Trp Met
35 40 45

Gly Trp Ile Asp Pro Asp Gln Gly Asp Thr Glu Tyr Ala Gln Lys Phe
50 55 60

```
Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val Ser Ser
        115                 120


<210> SEQ ID NO 7
<211> LENGTH: 107
<212> TYPE: PRT
<213> ORGANISM: Artificial Sequence
<220> FEATURE:
<223> OTHER INFORMATION: AB6.12-G1 Light chain variable region

<400> SEQUENCE: 7

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105


<210> SEQ ID NO 8
<211> LENGTH: 117
<212> TYPE: PRT
<213> ORGANISM: Artificial Sequence
<220> FEATURE:
<223> OTHER INFORMATION: Hu5F9-G4 Heavy chain variable region

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115
```

-continued

<210> SEQ ID NO 9
<211> LENGTH: 112
<212> TYPE: PRT
<213> ORGANISM: Artificial Sequence
<220> FEATURE:
<223> OTHER INFORMATION: Hu5F9-G4 Light chain variable region

<400> SEQUENCE: 9

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Ile Val Tyr Ser
20 25 30

Asn Gly Asn Thr Tyr Leu Gly Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Tyr Thr Phe Gly Gln Gly Thr Lys Leu Glu Ile Lys
100 105 110

<210> SEQ ID NO 10
<211> LENGTH: 15
<212> TYPE: PRT
<213> ORGANISM: Artificial Sequence
<220> FEATURE:
<223> OTHER INFORMATION: Synthetic linker

<400> SEQUENCE: 10

Gly Gly Gly Gly Ser Gly Gly Gly Gly Ser Gly Gly Gly Gly Ser
1 5 10 15

<210> SEQ ID NO 11
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 11

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Leu Asp Asn Tyr
20 25 30

Tyr Trp Ser Trp Ile Arg Gln Pro Pro Gly Lys Gly Leu Glu Trp Ile
35 40 45

Gly Tyr Ile Tyr Tyr Ser Gly Asn Thr Asn Tyr Asn Pro Ser Leu Lys
50 55 60

Ser Arg Val Thr Ile Ser Val Asp Thr Ser Lys Asn Gln Phe Ser Leu
65 70 75 80

Arg Leu Arg Ser Val Thr Ala Ala Asp Thr Ala Val Tyr Tyr Cys Ala
85 90 95

Arg Gly Gly Arg Phe Leu Glu Arg Tyr Trp Gly Gln Gly Thr Leu Val
100 105 110

Thr Val Ser Ser
115

<210> SEQ ID NO 12

<211> LENGTH: 107
<212> TYPE: PRT
<213> ORGANISM: Artificial Sequence
<220> FEATURE:
<223> OTHER INFORMATION: Light chain variable region

<400> SEQUENCE: 12

Asp Ile Gln Met Thr Gln Ser Pro Ser Ser Val Ser Ala Ser Val Gly
1 5 10 15

Asp Arg Val Thr Ile Ser Cys Arg Ala Asn Gln Ala Ile Gly Thr Trp
20 25 30

Leu Ala Trp Tyr Gln Gln Lys Pro Gly Lys Ala Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Glu Phe Thr Leu Thr Ile Ser Ser Leu Gln Ala
65 70 75 80

Glu Asp Val Ala Val Tyr Tyr Cys Gln Gln Tyr Tyr Thr Thr Pro Leu
85 90 95

Thr Phe Gly Gly Gly Thr Lys Leu Glu Ile Lys
100 105

<210> SEQ ID NO 13
<211> LENGTH: 107
<212> TYPE: PRT
<213> ORGANISM: Artificial Sequence
<220> FEATURE:
<223> OTHER INFORMATION: Light chain variable region

<400> SEQUENCE: 13

Glu Ile Val Leu Thr Gln Pro Pro Ser Ser Leu Ser Ala Ser Val Gly
1 5 10 15

Asp Arg Val Thr Ile Pro Cys Arg Ala Ser Leu Ser Ile Gly Ser Phe
20 25 30

Leu Asn Trp Tyr Gln Gln Arg Pro Gly Glu Ala Pro Lys Leu Leu Ile
35 40 45

Phe Ala Ala Ser Ser Leu Arg Ser Gly Val Pro Ser Arg Phe Ser Gly
50 55 60

Ser Gly Ser Gly Thr Asp Phe Thr Leu Thr Ile Ser Gly Leu Gln Pro
65 70 75 80

Glu Asp Phe Ala Thr Tyr Tyr Cys Gln Gln Thr Tyr Thr Thr Pro Tyr
85 90 95

Thr Phe Gly Gln Gly Thr Lys Val Asp Ile Lys
100 105

<210> SEQ ID NO 14
<211> LENGTH: 6
<212> TYPE: PRT
<213> ORGANISM: Artificial Sequence
<220> FEATURE:
<223> OTHER INFORMATION: VH CDR1

<400> SEQUENCE: 14

Asp Asn Tyr Tyr Trp Ser
1 5

<210> SEQ ID NO 15
<211> LENGTH: 6
<212> TYPE: PRT
<213> ORGANISM: Artificial Sequence
<220> FEATURE:

<223> OTHER INFORMATION: VH CDR1

<400> SEQUENCE: 15

Asp Gly Tyr Tyr Trp Ser
1 5

<210> SEQ ID NO 16
<211> LENGTH: 6
<212> TYPE: PRT
<213> ORGANISM: Artificial Sequence
<220> FEATURE:
<223> OTHER INFORMATION: VH CDR1

<400> SEQUENCE: 16

Asn Asp Tyr Tyr Trp Ser
1 5

<210> SEQ ID NO 17
<211> LENGTH: 16
<212> TYPE: PRT
<213> ORGANISM: Artificial Sequence
<220> FEATURE:
<223> OTHER INFORMATION: VH CDR2

<400> SEQUENCE: 17

Tyr Ile Tyr Tyr Ser Gly Asn Thr Asn Tyr Asn Pro Ser Leu Lys Ser
1 5 10 15

<210> SEQ ID NO 18
<211> LENGTH: 16
<212> TYPE: PRT
<213> ORGANISM: Artificial Sequence
<220> FEATURE:
<223> OTHER INFORMATION: VH CDR2

<400> SEQUENCE: 18

Arg Ile Tyr Gly Asn Ser Thr Thr Asn Tyr Asn Pro Ser Leu Lys Ser
1 5 10 15

<210> SEQ ID NO 19
<211> LENGTH: 16
<212> TYPE: PRT
<213> ORGANISM: Artificial Sequence
<220> FEATURE:
<223> OTHER INFORMATION: VH CDR2

<400> SEQUENCE: 19

Arg Ile Tyr Gly Asn Gly Asp Thr Asn Tyr Asn Pro Ser Leu Lys Ser
1 5 10 15

<210> SEQ ID NO 20
<211> LENGTH: 16
<212> TYPE: PRT
<213> ORGANISM: Artificial Sequence
<220> FEATURE:
<223> OTHER INFORMATION: VH CDR2

<400> SEQUENCE: 20

Arg Ile Tyr Tyr Asn Gly Asn Thr Asn Tyr Asn Pro Ser Leu Lys Ser
1 5 10 15

<210> SEQ ID NO 21
<211> LENGTH: 16
<212> TYPE: PRT
<213> ORGANISM: Artificial Sequence
<220> FEATURE:
<223> OTHER INFORMATION: VH CDR2

<400> SEQUENCE: 21

Arg Ile Tyr Gly Asp Ser Ala Thr Asn Tyr Asn Pro Ser Leu Lys Ser
1 5 10 15

<210> SEQ ID NO 22
<211> LENGTH: 16
<212> TYPE: PRT
<213> ORGANISM: Artificial Sequence
<220> FEATURE:
<223> OTHER INFORMATION: VH CDR2

<400> SEQUENCE: 22

Arg Ile Tyr Asp Gly Ser Gly Thr Asn Tyr Asn Pro Ser Leu Lys Ser
1 5 10 15

<210> SEQ ID NO 23
<211> LENGTH: 8
<212> TYPE: PRT
<213> ORGANISM: Artificial Sequence
<220> FEATURE:
<223> OTHER INFORMATION: VH CDR3

<400> SEQUENCE: 23

Gly Gly Arg Phe Leu Glu Arg Tyr
1 5

<210> SEQ ID NO 24
<211> LENGTH: 8
<212> TYPE: PRT
<213> ORGANISM: Artificial Sequence
<220> FEATURE:
<223> OTHER INFORMATION: VH CDR3

<400> SEQUENCE: 24

Gly Gly Arg Ile Phe Gly Gly Tyr
1 5

<210> SEQ ID NO 25
<211> LENGTH: 8
<212> TYPE: PRT
<213> ORGANISM: Artificial Sequence
<220> FEATURE:
<223> OTHER INFORMATION: VH CDR3

<400> SEQUENCE: 25

Gly Gly Arg Ile Phe Ala Gly Tyr
1 5

<210> SEQ ID NO 26
<211> LENGTH: 8
<212> TYPE: PRT
<213> ORGANISM: Artificial Sequence
<220> FEATURE:
<223> OTHER INFORMATION: VH CDR3

<400> SEQUENCE: 26

Gly Gly Arg Ile Leu Ala Gly Tyr
1 5

<210> SEQ ID NO 27
<211> LENGTH: 8
<212> TYPE: PRT
<213> ORGANISM: Artificial Sequence
<220> FEATURE:
<223> OTHER INFORMATION: VH CDR3

<400> SEQUENCE: 27

Gly Gly Arg Ile Phe Ser Gly Tyr
1 5

<210> SEQ ID NO 28
<211> LENGTH: 7
<212> TYPE: PRT
<213> ORGANISM: Artificial Sequence
<220> FEATURE:
<223> OTHER INFORMATION: VH CDR3

<400> SEQUENCE: 28

Gly Arg Gly Ile Phe Gly Tyr
1 5

<210> SEQ ID NO 29
<211> LENGTH: 7
<212> TYPE: PRT
<213> ORGANISM: Artificial Sequence
<220> FEATURE:
<223> OTHER INFORMATION: VH CDR3

<400> SEQUENCE: 29

Gly Gly Arg Ile Phe Gly His
1 5

<210> SEQ ID NO 30
<211> LENGTH: 11
<212> TYPE: PRT
<213> ORGANISM: Artificial Sequence
<220> FEATURE:
<223> OTHER INFORMATION: VL CDR1

<400> SEQUENCE: 30

Arg Ala Ser Leu Ser Ile Gly Ser Phe Leu Asn
1 5 10

<210> SEQ ID NO 31
<211> LENGTH: 11
<212> TYPE: PRT
<213> ORGANISM: Artificial Sequence
<220> FEATURE:
<223> OTHER INFORMATION: VL CDR1

<400> SEQUENCE: 31

Arg Ala Asn Gln Ala Ile Gly Thr Trp Leu Ala
1 5 10

<210> SEQ ID NO 32
<211> LENGTH: 7
<212> TYPE: PRT
<213> ORGANISM: Artificial Sequence
<220> FEATURE:
<223> OTHER INFORMATION: VL CDR2

<400> SEQUENCE: 32

Ala Ala Ser Ser Leu Arg Ser
1 5

<210> SEQ ID NO 33
<211> LENGTH: 7
<212> TYPE: PRT
<213> ORGANISM: Artificial Sequence
<220> FEATURE:
<223> OTHER INFORMATION: VL CDR2

<400> SEQUENCE: 33

```
Ala Ala Ser Thr Leu Gln Ser
1               5


<210> SEQ ID NO 34
<211> LENGTH: 9
<212> TYPE: PRT
<213> ORGANISM: Artificial Sequence
<220> FEATURE:
<223> OTHER INFORMATION: VL CDR3

<400> SEQUENCE: 34

Gln Gln Thr Tyr Thr Thr Pro Tyr Thr
1               5


<210> SEQ ID NO 35
<211> LENGTH: 9
<212> TYPE: PRT
<213> ORGANISM: Artificial Sequence
<220> FEATURE:
<223> OTHER INFORMATION: VL CDR3

<400> SEQUENCE: 35

Gln Gln Tyr Tyr Thr Thr Pro Leu Thr
1               5


<210> SEQ ID NO 36
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Ile Phe Gly Gly Tyr Trp Gly Gln Gly Thr Leu Val
            100                 105                 110

Thr Val Ser Ser
        115


<210> SEQ ID NO 37
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
            20                  25                  30
```

```
Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Ile Phe Ala Gly Tyr Trp Gly Gln Gly Thr Leu Val
            100                 105                 110

Thr Val Ser Ser
        115


<210> SEQ ID NO 38
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Gly Tyr
            20                  25                  30

Tyr Trp Ser Trp Ile Arg Gln Pro Pro Gly Lys Gly Leu Glu Trp Ile
        35                  40                  45

Gly Arg Ile Tyr Gly Asn Ser Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Ile Phe Ala Gly Tyr Trp Gly Gln Gly Thr Leu Val
            100                 105                 110

Thr Val Ser Ser
        115


<210> SEQ ID NO 39
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asn Asp Tyr
            20                  25                  30

Tyr Trp Ser Trp Ile Arg Gln Pro Pro Gly Lys Gly Leu Glu Trp Ile
        35                  40                  45

Gly Arg Ile Tyr Gly Asn Gly Asp Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
```

```
                85                  90                  95

Arg Gly Gly Arg Ile Leu Ala Gly Tyr Trp Gly Gln Gly Thr Leu Val
            100                 105                 110

Thr Val Ser Ser
        115


<210> SEQ ID NO 40
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
            20                  25                  30

Tyr Trp Ser Trp Ile Arg Gln Pro Pro Gly Lys Gly Leu Glu Trp Ile
        35                  40                  45

Gly Arg Ile Tyr Tyr Asn Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Ile Leu Ala Gly Tyr Trp Gly Gln Gly Thr Leu Val
            100                 105                 110

Thr Val Ser Ser
        115


<210> SEQ ID NO 41
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Ile Phe Ser Gly Tyr Trp Gly Gln Gly Thr Leu Val
            100                 105                 110

Thr Val Ser Ser
        115


<210> SEQ ID NO 42
<211> LENGTH: 115
```

<212> TYPE: PRT
<213> ORGANISM: Artificial Sequence
<220> FEATURE:
<223> OTHER INFORMATION: Heavy chain variable region

<400> SEQUENCE: 42

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Arg Gly Ile Phe Gly Tyr Trp Gly Gln Gly Thr Leu Val Thr
            100                 105                 110

Val Ser Ser
        115
```

<210> SEQ ID NO 43
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 43

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
            20                  25                  30

Tyr Trp Ser Trp Ile Arg Gln Pro Pro Gly Lys Gly Leu Glu Trp Ile
        35                  40                  45

Gly Arg Ile Tyr Gly Asp Ser Ala Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Ile Phe Ser Gly Tyr Trp Gly Gln Gly Thr Leu Val
            100                 105                 110

Thr Val Ser Ser
        115
```

<210> SEQ ID NO 44
<211> LENGTH: 115
<212> TYPE: PRT
<213> ORGANISM: Artificial Sequence
<220> FEATURE:
<223> OTHER INFORMATION: Heavy chain variable region

<400> SEQUENCE: 44

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
```

```
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Ile Phe Gly His Trp Gly Gln Gly Thr Leu Val Thr
            100                 105                 110

Val Ser Ser
        115


<210> SEQ ID NO 45
<211> LENGTH: 107
<212> TYPE: PRT
<213> ORGANISM: Artificial Sequence
<220> FEATURE:
<223> OTHER INFORMATION: Light chain variable region

<400> SEQUENCE: 45

Glu Ile Val Leu Thr Gln Ser Pro Ser Thr Leu Ser Ala Ser Val Gly
1               5                   10                  15

Asp Arg Val Thr Ile Pro Cys Arg Ala Ser Leu Ser Ile Gly Ser Phe
            20                  25                  30

Leu Asn Trp Tyr Gln Gln Arg Pro Gly Glu Ala Pro Lys Leu Leu Ile
        35                  40                  45

Phe Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Tyr Thr Thr Pro Tyr
                85                  90                  95

Thr Phe Gly Gln Gly Thr Lys Val Glu Ile Lys
            100                 105


<210> SEQ ID NO 46
<211> LENGTH: 107
<212> TYPE: PRT
<213> ORGANISM: Artificial Sequence
<220> FEATURE:
<223> OTHER INFORMATION: Light chain variable region

<400> SEQUENCE: 46

Asp Ile Val Met Thr Gln Ser Pro Ser Ser Leu Ser Ala Ser Val Gly
1               5                   10                  15

Asp Arg Val Thr Ile Pro Cys Arg Ala Ser Leu Ser Ile Gly Ser Phe
            20                  25                  30

Leu Asn Trp Tyr Gln Gln Arg Pro Gly Glu Ala Pro Lys Leu Leu Ile
        35                  40                  45

Phe Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Tyr Thr Thr Pro Tyr
                85                  90                  95
```

```
Thr Phe Gly Pro Gly Thr Arg Leu Asp Ile Lys
            100                 105


<210> SEQ ID NO 47
<211> LENGTH: 107
<212> TYPE: PRT
<213> ORGANISM: Artificial Sequence
<220> FEATURE:
<223> OTHER INFORMATION: Light chain variable region

<400> SEQUENCE: 47

Glu Ile Val Leu Thr Gln Ser Pro Ser Ser Leu Ser Ala Ser Val Gly
1               5                   10                  15

Asp Arg Val Thr Ile Pro Cys Arg Ala Ser Leu Ser Ile Gly Ser Phe
            20                  25                  30

Leu Asn Trp Tyr Gln Gln Arg Pro Gly Glu Ala Pro Lys Leu Leu Ile
        35                  40                  45

Phe Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Tyr Thr Thr Pro Tyr
                85                  90                  95

Thr Phe Gly Pro Gly Thr Arg Leu Glu Ile Lys
            100                 105


<210> SEQ ID NO 48
<211> LENGTH: 107
<212> TYPE: PRT
<213> ORGANISM: Artificial Sequence
<220> FEATURE:
<223> OTHER INFORMATION: Light chain variable region

<400> SEQUENCE: 48

Asp Ile Gln Met Thr Gln Ser Pro Ser Ser Leu Ser Ala Ser Val Gly
1               5                   10                  15

Asp Arg Val Thr Ile Pro Cys Arg Ala Ser Leu Ser Ile Gly Ser Phe
            20                  25                  30

Leu Asn Trp Tyr Gln Gln Arg Pro Gly Glu Ala Pro Lys Leu Leu Ile
        35                  40                  45

Phe Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Thr Pro Tyr
                85                  90                  95

Thr Phe Gly Gln Gly Thr Lys Val Glu Ile Lys
            100                 105


<210> SEQ ID NO 49
<211> LENGTH: 107
<212> TYPE: PRT
<213> ORGANISM: Artificial Sequence
<220> FEATURE:
<223> OTHER INFORMATION: Light chain variable region

<400> SEQUENCE: 49

Glu Ile Val Leu Thr Gln Ser Pro Ser Ser Leu Ser Ala Ser Val Gly
1               5                   10                  15

Asp Arg Val Thr Ile Pro Cys Arg Ala Ser Leu Ser Ile Gly Ser Phe
```

```
            20                  25                  30

Leu Asn Trp Tyr Gln Gln Arg Pro Gly Glu Ala Pro Lys Leu Leu Ile
        35                  40                  45

Phe Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Thr Pro Tyr
                85                  90                  95

Thr Phe Gly Gln Gly Thr Lys Leu Glu Ile Lys
            100                 105


<210> SEQ ID NO 50
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Arg Phe Leu Glu Arg Tyr Trp Gly Gln Gly Thr Leu Val
            100                 105                 110

Thr Val Ser Ser
        115


<210> SEQ ID NO 51
<211> LENGTH: 107
<212> TYPE: PRT
<213> ORGANISM: Artificial Sequence
<220> FEATURE:
<223> OTHER INFORMATION: Light chain variable region

<400> SEQUENCE: 51

Glu Ile Val Leu Thr Gln Ser Pro Ser Ser Leu Ser Ala Ser Val Gly
1               5                   10                  15

Asp Arg Val Thr Ile Pro Cys Arg Ala Ser Leu Ser Ile Gly Ser Phe
            20                  25                  30

Leu Asn Trp Tyr Gln Gln Arg Pro Gly Glu Ala Pro Lys Leu Leu Ile
        35                  40                  45

Phe Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Thr Pro Tyr
                85                  90                  95
```

Thr Phe Gly Gln Gly Thr Lys Val Glu Ile Lys
100 105

<210> SEQ ID NO 52
<211> LENGTH: 107
<212> TYPE: PRT
<213> ORGANISM: Artificial Sequence
<220> FEATURE:
<223> OTHER INFORMATION: Light chain variable region

<400> SEQUENCE: 52

Glu Ile Val Leu Thr Gln Ser Pro Ser Ser Leu Ser Ala Ser Val Gly
1 5 10 15

Asp Arg Val Thr Ile Pro Cys Arg Ala Ser Leu Ser Ile Gly Ser Phe
20 25 30

Leu Asn Trp Tyr Gln Gln Lys Pro Gly Lys Ala Pro Lys Leu Leu Ile
35 40 45

Phe Ala Ala Ser Ser Leu Arg Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Tyr Thr Thr Pro Tyr
85 90 95

Thr Phe Gly Gln Gly Thr Lys Val Glu Ile Lys
100 105

<210> SEQ ID NO 53
<211> LENGTH: 107
<212> TYPE: PRT
<213> ORGANISM: Artificial Sequence
<220> FEATURE:
<223> OTHER INFORMATION: Light chain variable region

<400> SEQUENCE: 53

Glu Ile Val Leu Thr Gln Ser Pro Ser Ser Leu Ser Ala Ser Val Gly
1 5 10 15

Asp Arg Val Thr Ile Thr Cys Arg Ala Ser Leu Ser Ile Gly Ser Phe
20 25 30

Leu Asn Trp Tyr Gln Gln Lys Pro Gly Lys Ala Pro Lys Leu Leu Ile
35 40 45

Phe Ala Ala Ser Ser Leu Arg Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Tyr Thr Thr Pro Tyr
85 90 95

Thr Phe Gly Gln Gly Thr Lys Val Glu Ile Lys
100 105

<210> SEQ ID NO 54
<211> LENGTH: 107
<212> TYPE: PRT
<213> ORGANISM: Artificial Sequence
<220> FEATURE:
<223> OTHER INFORMATION: Light chain variable region

<400> SEQUENCE: 54

Glu Ile Val Leu Thr Gln Ser Pro Ser Ser Leu Ser Ala Ser Val Gly
1 5 10 15

Asp Arg Val Thr Ile Thr Cys Arg Ala Ser Leu Ser Ile Gly Ser Phe

```
            20                  25                  30

Leu Asn Trp Tyr Gln Gln Lys Pro Gly Lys Ala Pro Lys Leu Leu Ile
        35                  40                  45

Tyr Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Thr Pro Tyr
                85                  90                  95

Thr Phe Gly Gln Gly Thr Lys Val Glu Ile Lys
            100                 105


<210> SEQ ID NO 55
<211> LENGTH: 107
<212> TYPE: PRT
<213> ORGANISM: Artificial Sequence
<220> FEATURE:
<223> OTHER INFORMATION: Light chain variable region

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Leu Ser Ile Gly Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Thr Pro Tyr
                85                  90                  95

Thr Phe Gly Gln Gly Thr Lys Val Glu Ile Lys
            100                 105


<210> SEQ ID NO 56
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Gly Tyr
            20                  25                  30

Tyr Trp Ser Trp Ile Arg Gln Pro Pro Gly Lys Gly Leu Glu Trp Ile
        35                  40                  45

Gly Arg Ile Tyr Asp Gly Ser Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Ile Phe Gly Gly Tyr Trp Gly Gln Gly Thr Leu Val
            100                 105                 110
```

```
Thr Val Ser Ser
        115


<210> SEQ ID NO 57
<211> LENGTH: 1329
<212> TYPE: DNA
<213> ORGANISM: Artificial Sequence
<220> FEATURE:
<223> OTHER INFORMATION: encoding the heavy chain of Antibody 6Y-G4

<400> SEQUENCE: 57

caggtgcagc tgcaggagtc cggccctggc ctggtgaagc cttccgagac cctgtccctg     60

acctgtaccg tgagcggcgg cagcctggat aactattact ggagctggat ccggcagcct    120

cctggcaagg gcctggagtg gatcggctac atctactatt ccggcaacac caattacaac    180

ccttccctga agagccgggt gaccatctcc gtggacacca gcaagaacca gtttagcctg    240

aagctgtcct ccgtgaccgc cgctgatacc gccgtgtact actgtgccag gggcggccgg    300

ttcctggaga gatattgggg ccagggtacc ctcgtgaccg tgtccagcgc tagcaccaag    360

ggcccttccg tgttcccccct ggcccccctgt agccggtcca cctctgagag caccgctgct    420

ctgggctgtc tggtgaagga ttactttccc gaaccggtga ccgtgtcatg gaactccggg    480

gctctgacat ccggtgtcca cacttttcct gcagtgctgc agtcatccgg cctgtacagc    540

ctgagctctg tggtcacagt cccaagttca tccctgggaa ccaagacata tacttgcaac    600

gtggatcata aacccagcaa tactaaggtc gacaaacgag tggagtctaa gtacggacca    660

ccttgcccac catgtccagc acctgagttc ctgggaggac caagcgtgtt cctgtttcct    720

ccaaagccta aagataccct gatgatcagt cggactcccg aggtcacctg cgtggtcgtg    780

gacgtgtccc aggaggaccc tgaagtccag ttcaactggt acgtggacgg cgtcgaagtg    840

cacaatgcta agacaaaacc tcgagaggaa cagtttaact ccacataccg tgtcgtgagc    900

gtcctgactg tgctgcatca ggattggctg aacggcaagg agtataagtg caaagtgagc    960

aataagggac tgccaagctc tatcgagaaa actatttcta aggctaaagg acagcctagg   1020

gaaccacagg tgtacaccct gcccccctagt caggaggaaa tgactaagaa ccaggtctca   1080

ctgacctgtc tggtgaaagg gttctatcct tcagatattg cagtggagtg ggaatccaat   1140

ggtcagccag agaacaatta caagacaact ccacccgtgc tggacagcga tgggtctttc   1200

tttctgtatt ctagactgac cgtggacaaa agtcgctggc aggagggtaa tgtcttttct   1260

tgtagtgtga tgcacgaagc cctgcacaac cactacactc agaaaagcct gtcactgtcc   1320

ctgggtaaa                                                          1329


<210> SEQ ID NO 58
<211> LENGTH: 645
<212> TYPE: DNA
<213> ORGANISM: Artificial Sequence
<220> FEATURE:
<223> OTHER INFORMATION: encoding the light chain of Antibody 6Y-G4

<400> SEQUENCE: 58

gagatcgtgc tgacccagtc cccctccagc ctgagcgcca gcgtgggaga ccgggtgacc     60

atcccctgcc gggcttccct gtccatcggc agcttcctga actggtatca gcagaggcct    120

ggcgaggccc ctaagctgct gatctttgcc gcttccagcc tgcggagcgg cgtgcctagc    180

aggttctccg gcagcggctc cggcaccgat ttcaccctga ccatcagcgg cctgcagccc    240

gaggatttcg ccacctacta ctgccagcag acctacacca cccccttacac ctttggccag    300
```

ggcaccaagg tggacatcaa gcgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttga 645

<210> SEQ ID NO 59
<211> LENGTH: 714
<212> TYPE: DNA
<213> ORGANISM: Artificial Sequence
<220> FEATURE:
<223> OTHER INFORMATION: encoding 17-ScFv

<400> SEQUENCE: 59
caggtgcagc tgcaggagtc gggcccagga ctggtgaagc cttcggagac cctgtccctc 60
acctgcactg tctctggtgg ctccctcgat aattactact ggagctggat ccggcagccc 120
ccagggaagg gactggagtg gattggatat atctattaca gtgggaacac caactacaac 180
ccctccctca agagtcgagt caccatatca gtagacacgt ccaagaacca gttctcgttg 240
aggctgaggt ctgtgaccgc tgcggacacg gccgtgtatt actgtgcgag aggagggcga 300
tttttggaac gttactgggg ccagggaacc ctggtcaccg tctcctcagg tggaggcggt 360
tcaggcggag gtggctctgg cggtggcgga tcggacatcc agatgaccca gtctccatct 420
tccgtgtctg catctgtagg agacagagtc accatctctt gtcgggcgaa tcaggctatt 480
ggcacttggt tagcctggta tcagcaaaag ccaggaaaag cccctaagct cctgatctat 540
gcggcatcca ctttgcaaag tggggtccca tcaaggttca gcggcagtgg atctgggaca 600
gaattcactc tcaccatcag cagcctgcag gctgaagatg tggcagttta ttactgtcag 660
caatattata ctactcccct cactttcggc ggagggacca agctggagat caaa 714

<210> SEQ ID NO 60
<211> LENGTH: 443
<212> TYPE: PRT
<213> ORGANISM: Artificial Sequence
<220> FEATURE:
<223> OTHER INFORMATION: heavy chain of Antibody 6Y-G4

<400> SEQUENCE: 60

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Leu Asp Asn Tyr
20 25 30

Tyr Trp Ser Trp Ile Arg Gln Pro Pro Gly Lys Gly Leu Glu Trp Ile
35 40 45

Gly Tyr Ile Tyr Tyr Ser Gly Asn Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Gly Arg Phe Leu Glu Arg Tyr Trp Gly Gln Gly Thr Leu Val
100 105 110

Thr Val Ser Ser Ala Ser Thr Lys Gly Pro Ser Val Phe Pro Leu Ala
115 120 125

```
Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440


<210> SEQ ID NO 61
<211> LENGTH: 214
<212> TYPE: PRT
<213> ORGANISM: Artificial Sequence
<220> FEATURE:
<223> OTHER INFORMATION: light chain of Antibody 6Y-G4

<400> SEQUENCE: 61

Glu Ile Val Leu Thr Gln Ser Pro Ser Ser Leu Ser Ala Ser Val Gly
1               5                   10                  15

Asp Arg Val Thr Ile Pro Cys Arg Ala Ser Leu Ser Ile Gly Ser Phe
            20                  25                  30

Leu Asn Trp Tyr Gln Gln Arg Pro Gly Glu Ala Pro Lys Leu Leu Ile
        35                  40                  45
```

Phe Ala Ala Ser Ser Leu Arg Ser Gly Val Pro Ser Arg Phe Ser Gly
50 55 60

Ser Gly Ser Gly Thr Asp Phe Thr Leu Thr Ile Ser Gly Leu Gln Pro
65 70 75 80

Glu Asp Phe Ala Thr Tyr Tyr Cys Gln Gln Thr Tyr Thr Thr Pro Tyr
85 90 95

Thr Phe Gly Gln Gly Thr Lys Val Asp Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 62
<211> LENGTH: 446
<212> TYPE: PRT
<213> ORGANISM: Artificial Sequence
<220> FEATURE:
<223> OTHER INFORMATION: heavy chain of Antibody 6Y-G1

<400> SEQUENCE: 62

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Leu Asp Asn Tyr
20 25 30

Tyr Trp Ser Trp Ile Arg Gln Pro Pro Gly Lys Gly Leu Glu Trp Ile
35 40 45

Gly Tyr Ile Tyr Tyr Ser Gly Asn Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Gly Arg Phe Leu Glu Arg Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

```
Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 63
<211> LENGTH: 446
<212> TYPE: PRT
<213> ORGANISM: Artificial Sequence
<220> FEATURE:
<223> OTHER INFORMATION: heavy chain of Antibody 17

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Asp Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Gly Gly Arg Phe Leu Glu Arg Tyr Trp Gly Gln Gly Thr Leu Val
            100                 105                 110
```

```
Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 64
<211> LENGTH: 214
<212> TYPE: PRT
<213> ORGANISM: Artificial Sequence
<220> FEATURE:
<223> OTHER INFORMATION: light chain of Antibody 17

<400> SEQUENCE: 64

```
Asp Ile Gln Met Thr Gln Ser Pro Ser Ser Val Ser Ala Ser Val Gly
1               5                   10                  15

Asp Arg Val Thr Ile Ser Cys Arg Ala Asn Gln Ala Ile Gly Thr Trp
            20                  25                  30
```

```
Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Ala
65                  70                  75                  80

Glu Asp Val Ala Val Tyr Tyr Cys Gln Gln Tyr Tyr Thr Thr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 65
<211> LENGTH: 107
<212> TYPE: PRT
<213> ORGANISM: Artificial Sequence
<220> FEATURE:
<223> OTHER INFORMATION: Light chain variable region

<400> SEQUENCE: 65

```
Glu Ile Val Leu Thr Gln Ser Pro Ser Ser Leu Ser Ala Ser Val Gly
1               5                   10                  15

Asp Arg Val Thr Ile Pro Cys Arg Ala Ser Leu Ser Ile Gly Ser Phe
            20                  25                  30

Leu Asn Trp Tyr Gln Gln Arg Pro Gly Glu Ala Pro Lys Leu Leu Ile
        35                  40                  45

Phe Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Thr Tyr Thr Thr Pro Tyr
                85                  90                  95

Thr Phe Gly Gln Gly Thr Lys Val Asp Ile Lys
            100                 105
```